US010479996B2

(12) United States Patent
Iversen et al.

(10) Patent No.: US 10,479,996 B2
(45) **Date of Patent: *Nov. 19, 2019**

(54) ANTISENSE ANTIVIRAL COMPOUND AND METHOD FOR TREATING SS/RNA VIRAL INFECTION

(71) Applicant: Sarepta Therapeutics, Inc., Corvallis, OR (US)

(72) Inventors: Patrick L. Iversen, Corvallis, OR (US); David A. Stein, Corvallis, OR (US); Dwight D. Weller, Corvallis, OR (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,092

(22) Filed: Nov. 6, 2014

(65) Prior Publication Data

US 2015/0267202 A1 Sep. 24, 2015

Related U.S. Application Data

(63) Continuation of application No. 13/335,450, filed on Dec. 22, 2011, now Pat. No. 8,906,872, which is a continuation of application No. 11/432,031, filed on May 10, 2006, now Pat. No. 8,084,433, which is a continuation-in-part of application No. 11/226,995, filed on Sep. 14, 2005, now Pat. No. 8,129,352.

(60) Provisional application No. 60/611,063, filed on Sep. 16, 2004.

(51) Int. Cl.

| | |
|---|---|
| ***C12N 15/113*** | (2010.01) |
| ***C07K 19/00*** | (2006.01) |
| ***C12N 15/11*** | (2006.01) |

(52) U.S. Cl.

CPC .......... *C12N 15/1131* (2013.01); *C07K 19/00* (2013.01); *C12N 15/111* (2013.01); *C12N 2310/11* (2013.01); *C12N 2310/314* (2013.01); *C12N 2310/3233* (2013.01); *C12N 2310/3513* (2013.01); *C12N 2310/531* (2013.01); *C12N 2320/11* (2013.01); *C12N 2770/00011* (2013.01); *C12N 2770/10011* (2013.01); *C12N 2770/12011* (2013.01); *C12N 2770/16011* (2013.01); *C12N 2770/20011* (2013.01); *C12N 2770/24011* (2013.01); *C12N 2770/28011* (2013.01); *C12N 2770/32011* (2013.01); *C12N 2770/36011* (2013.01)

(58) Field of Classification Search

CPC .............. C12N 15/111; C12N 15/1131; C12N 2310/11; C12N 2310/531; C12N 2310/3233

USPC ............................ 514/44; 530/322; 536/24.5

See application file for complete search history.

(56) References Cited

U.S. PATENT DOCUMENTS

| | | | | |
|---|---|---|---|---|
| 5,034,506 | A | | 7/1991 | Summerton et al. |
| 5,142,047 | A | | 8/1992 | Summerton et al. |
| 5,166,315 | A | * | 11/1992 | Summerton ..... A61K 47/48023 528/403 |
| 5,185,444 | A | | 2/1993 | Summerton et al. |
| 5,194,428 | A | | 3/1993 | Agrawal et al. |
| 5,217,866 | A | | 6/1993 | Summerton et al. |
| 5,495,006 | A | | 2/1996 | Climie et al. |
| 5,506,337 | A | | 4/1996 | Summerton et al. |
| 5,521,063 | A | | 5/1996 | Summerton et al. |
| 5,576,302 | A | | 11/1996 | Cook et al. |
| 5,580,767 | A | | 12/1996 | Cowsert et al. |
| 5,698,685 | A | * | 12/1997 | Summerton ..... A61K 47/48061 435/6.14 |
| 5,702,891 | A | | 12/1997 | Kolberg et al. |
| 5,734,039 | A | | 3/1998 | Calabretta et al. |
| 5,738,985 | A | | 4/1998 | Miles et al. |
| 5,801,154 | A | | 9/1998 | Baracchini et al. |
| 5,892,023 | A | * | 4/1999 | Pirotzky ............ C12N 15/1138 435/6.16 |
| 5,955,318 | A | | 9/1999 | Simons et al. |
| 5,989,904 | A | | 11/1999 | Das et al. |
| 6,060,456 | A | | 5/2000 | Arnold et al. |
| 6,133,246 | A | | 10/2000 | McKay et al. |

(Continued)

FOREIGN PATENT DOCUMENTS

| | | |
|---|---|---|
| JP | 2001-226400 A | 8/2001 |
| WO | 98/12312 A1 | 3/1998 |

(Continued)

OTHER PUBLICATIONS

Hudziak et al, Antisense & Nucleic Acid Drug Development, 1996, 6, 267-272.*

Agrawal et al, Proc. Natl. Acad. Sci. USA 1988, 85, 7079-7083.*

Adelman et al., "RNA Silencing of Dengue Virus Type 2 Replication in Transformed C6/36 Mosquito Cells Transcribing an Inverted-Repeat RNA Derived from the Virus Genome" *Journal of Virology* 76(24):12925-12933, 2002.

Agrawal et al., "Oligodeoxynucleoside Phosphoramidates and Phosphorothioates as Inhibitors of Human Immunodeficiency Virus," *Proc. Nat'l. Acad. Sci. USA* 85(19):7079-7083, 1988.

(Continued)

*Primary Examiner* — Ganapathy Krishnan

(74) *Attorney, Agent, or Firm* — Seed Intellectual Property Law Group LLP

(57) ABSTRACT

The invention provides antisense antiviral compounds and methods of their use and production in inhibition of growth of viruses of the Flaviviridae, Picornaviridae, Caliciviridae, Togaviridae, Arteriviridae, Coronaviridae, Astroviridae and Hepeviridae families in the treatment of a viral infection. The antisense antiviral compounds are substantially uncharged morpholino oligonucleotides having a sequence of 12-40 subunits, including at least 12 subunits having a targeting sequence that is complementary to a region associated with stem-loop secondary structure within the 5'-terminal end 40 bases of the positive-sense RNA strand of the virus.

9 Claims, 14 Drawing Sheets

Specification includes a Sequence Listing.

(56) References Cited

U.S. PATENT DOCUMENTS

| | | | | |
|---|---|---|---|---|
| 6,174,868 | B1 | 1/2001 | Anderson et al. | |
| 6,214,555 | B1 | 4/2001 | Leushner et al. | |
| 6,228,579 | B1 | 5/2001 | Zyskind et al. | |
| 6,239,265 | B1 | 5/2001 | Cook | |
| 6,258,570 | B1 | 7/2001 | Glustein et al. | |
| 6,306,993 | B1 | 10/2001 | Rothbard et al. | |
| 6,365,351 | B1 | 4/2002 | Iversen | |
| 6,365,577 | B1 | 4/2002 | Iversen | |
| 6,391,542 | B1 | 5/2002 | Anderson et al. | |
| 6,495,663 | B1 | 12/2002 | Rothbard | |
| 6,669,951 | B2 | 12/2003 | Rothbard et al. | |
| 6,677,153 | B2 | 1/2004 | Iversen | |
| 6,784,291 | B2 | 8/2004 | Iversen et al. | |
| 6,828,105 | B2 | 12/2004 | Stein et al. | |
| 6,841,542 | B2 | 1/2005 | Bartelmez et al. | |
| 6,841,675 | B1 | 1/2005 | Schmidt et al. | |
| 6,881,825 | B1 | 4/2005 | Robbins et al. | |
| 7,049,431 | B2 | 5/2006 | Iversen et al. | |
| 7,094,765 | B1 | 8/2006 | Iversen et al. | |
| 7,115,374 | B2 | 10/2006 | Linnen et al. | |
| 7,468,418 | B2 | 12/2008 | Iversen et al. | |
| 7,507,196 | B2 | 3/2009 | Stein et al. | |
| 7,524,829 | B2 | 4/2009 | Stein et al. | |
| 7,582,615 | B2 | 9/2009 | Neuman et al. | |
| 8,129,352 | B2 | 3/2012 | Iversen et al. | |
| 8,906,872 | B2 | 12/2014 | Iversen et al. | |
| 9,249,243 | B2 * | 2/2016 | Weller | A61K 48/00 |
| 2003/0166588 | A1 | 9/2003 | Iversen et al. | |
| 2003/0171311 | A1 | 9/2003 | Blatt et al. | |
| 2003/0171335 | A1 | 9/2003 | Stein et al. | |
| 2003/0224353 | A1 * | 12/2003 | Stein | C12N 15/1131 435/5 |
| 2004/0072239 | A1 | 4/2004 | Renaud et al. | |
| 2004/0259108 | A1 | 12/2004 | Linnen et al. | |
| 2004/0265879 | A1 | 12/2004 | Iversen et al. | |
| 2005/0171044 | A1 | 8/2005 | Stein et al. | |
| 2005/0176661 | A1 | 8/2005 | Vaillant et al. | |
| 2006/0063150 | A1 | 3/2006 | Iversen et al. | |
| 2006/0148747 | A1 | 7/2006 | Stein et al. | |
| 2006/0149046 | A1 | 7/2006 | Arar | |
| 2006/0269911 | A1 | 11/2006 | Iversen et al. | |
| 2007/0004661 | A1 | 1/2007 | Stein et al. | |
| 2007/0066556 | A1 | 3/2007 | Stein et al. | |
| 2007/0129323 | A1 | 6/2007 | Stein et al. | |
| 2007/0265214 | A1 | 11/2007 | Stein et al. | |
| 2009/0012280 | A1 | 1/2009 | Stein et al. | |
| 2009/0082547 | A1 | 3/2009 | Iversen et al. | |
| 2009/0088562 | A1 | 4/2009 | Weller et al. | |
| 2009/0099066 | A1 | 4/2009 | Moulton et al. | |
| 2009/0186847 | A1 | 7/2009 | Stein et al. | |
| 2009/0186848 | A1 | 7/2009 | Stein et al. | |
| 2009/0186849 | A1 | 7/2009 | Stein et al. | |
| 2010/0063133 | A1 | 3/2010 | Neuman et al. | |

FOREIGN PATENT DOCUMENTS

| | | | |
|---|---|---|---|
| WO | 98/33904 | A2 | 8/1998 |
| WO | 99/29350 | A1 | 6/1999 |
| WO | 01/049775 | A2 | 7/2001 |
| WO | 02/026968 | A2 | 4/2002 |
| WO | 02/068637 | A2 | 9/2002 |
| WO | 02/081495 | A1 | 10/2002 |
| WO | 03/033657 | A2 | 4/2003 |
| WO | 2005/007805 | A2 | 1/2005 |
| WO | 2005/013905 | A2 | 2/2005 |
| WO | 2005/030800 | A2 | 4/2005 |
| WO | 2005/065268 | A2 | 7/2005 |
| WO | 2006/047683 | A2 | 5/2006 |
| WO | 2006/050414 | A2 | 5/2006 |
| WO | 2007/030576 | A2 | 3/2007 |
| WO | 2007/030691 | A2 | 3/2007 |
| WO | 2007/103529 | A2 | 9/2007 |

OTHER PUBLICATIONS

Agrawal et al., "Site-Specific Excision from RNA by RNase H and Mixed-Phosphate-Backbone Oligodeoxynucleotides," *Proc. Nat'l. Acad Sci. USA* 87(4):1401-1405, 1990.

Agrawal et al., "Antisense Therapeutics: Is it as Simple as Complementary Base Recognition?" *Molecular Medicine Today* 6:72-81, 2000.

Alt et al., "Specific Inhibition of Hepatitis C Viral Gene Expression by Antisense Phosphorothioate Oligodeoxynucleotides" *Hepatology* 22(3):707-717, 1995. (Abstract Only).

Arora et al., "Redirection of Drug Metabolism Using Antisense Technology," *Curr. Opin. Mol. Ther.* 3(3):249-257, 2001.

Bailey et al., "Cationic Oligonucleotides Can Mediate Specific Inhibition of Gene Expression in Xenopus Oocytes," *Nucleic Acids Res.* 26(21):4860-4867, 1998.

Banerjee and Dasgupta, "Interaction of Picornavirus 2C Polypeptide with the Viral Negative-Strand RNA," *J. Gen. Virol.* 82(Pt 11):2621-2627, 2001.

Banerjee and Dasgupta, "Specific Interaction of Hepatitis C Virus Protease/Helicase NS3 with the 3' Terminal Sequences of Viral Positive- and Negative-Strand RNA," *J. Virol.* 75(4):1708-1721, 2001.

Banerjee et al., "Poliovirus-Encoded 2C Polypeptide Specifically Binds to the 3'-Terminal Sequences of Viral Negative-Strand RNA," *J. Virol.* 71(12):9570-9508, 1997.

Banerjee et al., "Interaction of Poliovirus-Encoded 2C/2BC Polypeptides with the 3' Terminus Negative-Strand Cloverleaf Requires an Intact Stem-Loop B," *Virology* 280(1):41-51, 2001.

Barawkar et al., "Synthesis, BioPhysical Properties, and Nuclease Resistance Properties of Mixed Backbone Oligodeoxynucleotides Containing Cationic Internucleoside Guanidinium Linkages: Deoxynucleic Guanidine/DNA Chimeras," *Proc. Natl. Acad. Sci. USA* 95(19):11047-11052, 1998.

Basler et al., "The Ebola Virus VP35 Protein Functions as a Type I IFN Antagonist," *Proc. Natl. Acad. Sci. USA* 97(22):12289-12294, 2000.

Blommers et al., "An Approach to the Structure Determination of Nucleic Acid Analogues Hybridized to RNA. NMR Studies of a Duplex between 2'-OMe RNA and an Oligonucleotide Containing a Single Amide Backbone Modification," *Nucleic Acids Res.* 22(20):4187-4194, 1994.

Bonham et al., "An Assessment of Antisense Properties of RNase H-Competent and Steric-Blocking Oligomers," *Nucleic Acids Res.* 23(7):1197-1203, 1995.

Borio et al., "Hemorrhagic Fever Viruses as Biological Weapons: Medical and Public Health Management," *J. Amer. Med. Assn.* 287(18):2391-2405, 2002.

Boudvillain et al., "Transplatin-Modified Oligo(2'O-methyl ribonucleotide)s: A New Tool for Selective Modulation of Gene Expression," *Biochemistry* 36(10):2925-2931, 1997.

Branch, "A Good Antisense Molecule is Hard to Find," *TIBS* 23:45-50, 1998.

Brasey et al., "The Leader of Human Immunodeficiency Virus Type 1 Genomic RNA Harbors an Internal Ribosome Entry Segment that is Active During the G2/M Phase of the Cell Cycle," *J. Virology* 77(7):3939-3949, 2003.

Bray et al., "A Mouse Model for Evaluation of Prophylaxis and Therapy of Ebola Hemorrhagic Fever," *J. Infectious Diseases* 178(3):651-661, 1998.

Brinton, "The Molecular Biology of West Nile Virus: A New Invader of the Western Hemisphere," *Annual. Rev. Microbiol.* 56:371-402, 2002.

Burnett et al., "The Evolving Field of Biodefence: Therapeutic Developments and Diagnostics," *Natural Review Drug Discovery* 4:281-297, 2005.

Callahan et al., "Molecular Cloning and Complete Sequence Determination of RNA Genome of Human Rhinovirus Type 14," *Proc. Natl. Acad. Sci. USA* 82(3):732-736, 1985.

Chirilla et al., "The Use of Synthetic Polymers for Delivery of Therapeutic Antisense Oligodeoxynucleotides," *Biomaterials* 23(2):321-342, 2002.

Chu et al., "Genetic Relatedness among Structural Protein Genes of Dengue 1 Virus Strains," *J. Gen. Virol.* 70:1701-1712, 1989.

(56) References Cited

OTHER PUBLICATIONS

Clarke et al., "Organization and Expression of Calcivirus Genes," *J. Infect. Diseases* 181:S309-S316, 2000.
Communication Pursuant to Article 94(3) EPC for Corresponding Application No. 05796604.6, dated May 8, 2009, 4 pages.
Connolly et al., "Pathogenesis of Experimental Ebola Virus Infection in Guinea Pigs," *J. Infectious Diseases* 179(suppl. 1):S203-S217, 1999.
Corey et al., "Morpholino Antisense Oligonucleotides: Tools for Investigating Vertebrate Development," *Genome Biology* 2(5):1015.1-1015.3, 2001.
Corver et al., "Fine Mapping of a cis-Acting Sequence Element in Yellow Fever Virus RNA That is Required for RNA Replication and Cyclization," *J. Virology* 77(3):2265-2270, 2003.
Cox and Subbaro, "Global Epidemiology of Influenza: Past and Present," *Annual Rev. Med.* 51:407-421, 2000.
Cox et al., "Influenza," *The Lancet* 354(9186):1277-1282, 1999.
Crooke et al., "In Vitro Toxicological Evaluation of ISIS 1082, a Phosphorothioate Oligonucleotide Inhibitor of Herpes Simplex Virus," *Antimicrobial Agents and Chemotherapy* 36(3):527-532, 1992.
Crooke, "Chapter 1: Basic Principles of Antisense Therapeutics," Antisense Drug Technology: Principles, Strategies, and Applications, New York, Marcel Dekker, S. Crooke, Ed Springer, pp. 1-50, 1999.
Cross et al., "Solution Structure of an RNA × DNA Hybrid Duplex Containing a 3'-Thioformacetal Linker and an RNA A-Tract," *Biochemistry* 36(14):4096-4107, 1997.
Dagle et al., "Targeted Elimination of Zygotic Messages in Xenopus Leavis Embryos by Modified Oligonucleotides Possessing Terminal Cationic Linkages," *Nucleic Acids Res.* 28(10):2153-2157, 2000.
Database Geneseq Online "WNV DNAzyme Seq ID No. 20601" Retrieved from EBI Database Accession No. ACN20585 Abstract, 2004.
Database Geneseq Online "WNV DNAzyme Seq ID No. 21825" Database Accession No. ACN21809 Abstract, 2004.
Database Geneseq Online "WNV Minus Starand DNAzyme Seq ID No. 32671" Database Accession No. ACN32665 Abstract, 2004.
Database Geneseq Online "WNV Minus Starand DNAzyme Seq ID No. 333989" Database Accession No. ACN33973 Abstract, 2004.
Deas et al., "Inhibition of Flavivirus Infections by Antisense Oligomers Specifically Suppressing Viral Translation and RNA Replication," *J. Virology* 79(8):4599-4609, 2005.
Ding et al., "An Oligodeoxyribonucleotide N3'-P5' Phosphoramidate Duplex Forms an A-Type Helix in Solution," *Nucleic Acids Res.* 24(2):354-360, 1996.
Egholm et al., "PNA Hybridizes to Complementary Oligonucleotides Obeying the Watson-Crick Hydrogen-Bonding Rules," *Nature* 365(6446):566-568, 1993.
Enserink, "Infectious Disease: West Nile's Surprisingly Swift Continental Sweep" *Science* 297(5589):1988-1989, 2002.
European Search Report for Corresponding Application No. 05796604.6, dated Jan. 13, 2009, 7 pages.
Faria et al., "Phosphoramidate Oligonucleotides as Potent Antisense Molecules in Cells and in vivo," *Nature Biotechnology* 19(1):40-44, 2001.
Feigner et al., "Lipofection: A Highly Efficient, Lipid-Mediated DNA-Transfection Procedure," *Proc. Natl. Acad. Sci. USA* 84(21):7413-7417, 1987.
Feldman et al., "Molecular Biology and Evolution of Filoviruses," *Arch. Virol.* 7(suppl.):81-100, 1993.
Feldmann et al., "Classification, Structure, and Replication of Filoviruses," *Current Topics in Microbiology and Immunology* 235:1-21, 1999.
Feldmann et al. "Ebola Virus: from Discovery to Vaccine," *Nature Rev. Immun.* 3(8):677-685, 2003.
Fischer, "Cellular Uptake Mechanisms and Potential Therapeutic Utility of Peptidic Cell Delivery Vectors: Progress 2001-2006," Published online 2006 in Wiley Interscience, www.interscience.wiley.com, pp. 1-41, 2006.
Freier, "Methods of Selecting Sites in RNA for Antisense Targeting," Chapter 5 in *Antisense Drug Technology: Principles, Strategies and Applications*, CRC Press, pp. 107-118, Sep. 14, 2001.
Gait et al., "Synthetic-Analogues of Polynucleotides XII. Synthesis of Thymidine Derivatives Containing an Oxyacetamido- or an Oxyformamido-Linkage Instead of a Phosphodiester Group," *J. Chem. Soc.* (14):1684-1686, 1974.
Gee et al., "Assessment of High Affinity Hybridization, RNase H Cleavage, and Covalent Linkage in Translation Arrest by Antisense Oligonucleotides," *Antisense Nucleic Acid Drug Dev.* 8(2):103-111, 1998.
Geisbert et al., "Treatment of Ebola Virus Infection with a Recombinant Inhibitor of Factor VIIa/Tissue Factor: a Study in Rhesus Monkeys," *The Lancet* 362(9400):1953-1958, 2003.
Geisbert et al., "Ebola Virus: New Insights into Disease Aetiopathology and Possible Therapeutic Interventions," *Expert Reviews in Mol. Med.* 6(20):1-24, 2004.
Geller et al., "Antisense Antibacterial Method and Compound," Office Action mailed Sep. 29, 2010, U.S. Appl. No. 11/173,847, 25 pages.
Genbank Accession No. AF304460.
Ghosh et al., "Intracellular Delivery Strategies for Antisense Phosphorodiamidate Morpholino Oligomers," *Antisense & Nucleic Acid Drug Development* 10:263-274, 2000.
Gilbert et al., "Sieve Analysis: Methods for Assessing from Vaccine Trial Data How Vaccine Efficacy Varies with Genotypic and Phenotypic Pathogen Variation," *J. Clin. Epidemiology* 54(2001):68-85, 2001.
Green et al., "Antisense Oligonucleotides:an Evolving Technology for the Modulation of Gene Expression in Human Disease," *J. Am. Coll. Surg.* 191:93-105, 2000.
Gritsun et al., "Tick-borne Encephalitis," *Antiviral Research* 57(1-2):129-146, 2003.
Hahn et al., "Conserved Elements in the 3' Untranslated Region of Flavivrus RNAs and Potential Cyclization Sequences," *J. Mol. Biol.* 198(1):33-41, 1987.
Hanecak et al., "Antisense Oligonucleotide Inhibition of Hepatitis C Virus Gene Expression in Transformed Hepatocytes," *J. Virology* 70:5203-5212, 1996.
Hayes et al., "Dengue and Dengue Hemorrhagic Fever," *Pediatr. Infect. Dis. J.* 11(4):311-317, 1992.
Holland et al., *Emerging Viruses*, edited by Steven S. Morse, Oxford Univ. Press, New York, Chapter 19, Replication Error, Quasispecies, Populations and Extreme Evolution Rates of RNA Viruses:203-218, 1993.
Hudziak et al., "Resistance of Morpholino Phosphorodiamidate Oligomers to Enzymatic Degradation," *Antisense & Nucleic Acid Drug Dev.* 6:267-272, 1996.
International Search Report for Application No. PCT/US2002/032868, dated Nov. 25, 2003, 6 pages.
International Search Report for Application No. PCT/US2004/025335, dated Apr. 27, 2005, 7 pages.
International Search Report for Application No. PCT/US2004/043341, dated Nov. 18, 2005, 4 pages.
International Search Report for Application No. PCT/US2005/038780, dated Jul. 12, 2006, 5 pages.
International Search Report for Application No. PCT/US2005/039607, dated Aug. 29, 2007, 4 pages.
International Search Report for Application No. PCT/US2006/034786, dated Apr. 24, 2007, 2 pages.
International Search Report for Application No. PCT/US2006/034986, dated Apr. 24, 2007, 2 pages.
International Search Report for Application No. PCT/US2007/005977, dated Oct. 23, 2007, 2 pages.
International Search Report and Written Opinion for Application No. PCT/US2007/011435, dated Sep. 29, 2008, 10 pages.
Iversen, "Phosphorodiamidate Morpholino Oligomers: Favorable Properties for Sequence-Specific Gene Inactivation," *Current Opinion in Molecular Therapeutics* 3(3):235-238, 2001.
Iversen et al., "Antisense Antiviral Compounds and Methods for Treating a Filovirus Infection," U.S. Appl. No. 12/853,180, filed Aug. 9, 2010, 99 pages.

(56) References Cited

OTHER PUBLICATIONS

Iversen, "Antisense Antiviral Compound and Method for Treating Influenza Viral Infection," U.S. Appl. No. 61/261,278, filed Nov. 13, 2009, 105 pages.
Iversen, "Antisense Antiviral Compound and Method for Treating Influenza Viral Infection," U.S. Appl. No. 61/292,056, filed Jan. 4, 2010, 115 pages.
Iversen et al., "Splice-Region Antisense Composition and Method," Office Action dated Apr. 23, 2010, 11/433,214, 17 pages.
Jaeger et al., "Improved Predictions of Secondary Structures for RNA," *Proc. Natl. Acad. Sci.* USA 86:7706-7710, 1989.
Jahrling et al., "Evaluation of Immune Globulin and Recombinant Interferon-Alpha2b for Treatment of Experimental Ebola Virus Infections," *J. Infectious Diseases* 179(suppl. 1):S224-S234, 1999.
Jen et al., "Suppression of Gene Expression by Targeted Disruption of Messenger RNA: Available Options and Current Strategies," *Stem Cells* 18:307-319, 2000.
Johannes et al., "Identification of Eukaryotic mRNAs that are Translated at Reduced Cap Binding Complex eIF4F Concentrations Using a cDNA Microarray," *Proc. Natl. Acad. Sci. USA* 96(23):13118-13123, 1999.
Jubin et al., "Hepatitis C Virus Internal Ribosome Entry Site (IRES) Stem Loop IIId Contains a Phylogenetically Conserved GGG Triplet Essential for Translation and IRES Folding," *J. Virology* 74(22):10430-10437, 2000.
Khromykh et al., "Essential Role of Cyclization Sequences in Flavivirus RNA Replication," *J. Virology* 75(14):6719-6728, 2001.
Khromykh et al., "Significance in Replication of the Terminal Nucleotides of the *Flavivirus* Genome," *Journal of Virology* 77(19):10623-10629, Oct. 2003.
Kinney et al., "Inhibition of Dengue Virus Serotypes 1 to 4 in Vero Cell Cultures with Morpholino Oligomers," *J. Virology* 79:5116-5128, 2005.
Lee et al., "Complete Sequence of the RNA Genome of Human Rhinovirus 16, a Clinically Useful Common Cold Virus Belonging to the ICAM-1 Receptor Group," *Virus Genes* 9:177-181, 1994.
Lesnikowski et al., "Octa(thymidine methanephosphonates) of Partially Defined Stereochemistry: Synthesis and Effect of Chirality at Phosphorus on Binding to Pentadecadeoxyriboadenylic Acid," *Nucleic Acids Res.* 18(8): 2109-2115, 1990.
Leyssen et al., "Perspectives for the Treatment of Infections with *Flaviviridae," Clinical Microbiology Reviews* 13(1):67-82, 2000.
Li et al., "Cell Proteins TIA-1 and TIAR Interact with the 3' Stem-Loop of the West Nile Virus Complementary Minus-Strand RNA and Facilitate Virus Replication," *Journal of Virology* 76(23):11989-12000, 2002.
Linkletter and Brulce, "Solid-Phase Synthesis of Positively Charged Deoxynucleic Guanidine (DNG) Modified Oligonucleotides Containing Neutral Urea Linkages: Effect of Charge Deletions on Binding and Fidelity," *Bioorg. Med. Chem.* 8(11):1893-1901, 2000.
Liu et al., "Structural and Functional Analysis of the 5' Untranslated Region of Coxsackievirus B3 RNA: in vivoTranslational and Infectivity Studies of Full-Length Mutants," *Virology* 265:206-217, 1999.
Lopez de Quinto et al., "Involvement of the aphthovirus RNA region located between the two functional AUGs in start codon selection," *Virology* 255(2):324-336, 1999.
Markoff, "5'- and 3'-Noncoding Regions in Flavivirus RNA," *Adv. Virus Res.* 59:177-228, 2003.
McCaffrey et al., "A Potent and Specific Morpholino Antisense Inhibitor of Hepatitis C Translation in Mice," *Hepatology* 38(2):503-508, 2003.
Mertes et al., "Synthesis of Carbonate Analogs of Dinucleosides. 3'-thymidinyl 5'-thymidinyl carbonate, 3'-thymidinal 5'-(5-fluoro-2'-deoxyuridinyl) carbonate, and 3'-(5'-fluoro-2'-deoxyuridinyl) 5'-thymidinayl carbonate," *J. Med. Chem.* 12(1):154-157, 1969.
Micklefield, "Backbone Modification of Nucleic Acids: Synthesis, Structure and Therapeutic Applications," Curr. Med. Chem. 8(10):1157-1179, 2001.
Miranda et al., "Differential Activation of Apoptosis Regulatory Pathways During Monocytic vs Granulocytic Differentiation: a Requirement for Bcl-X(L) and XIAP in the Prolonged Survival of Monocytic Cells," *J. Leuk. Soc. Amer.* 17(2): 1175-1179, 2001.
Mizuta et al., "Antisense Oligonucleotides Directed against the Viral RNA Polymerase Gene Enhance Survival of Mice Infected with Influenza A," *Nature Biotech.* 17(6):583-587, 1999.
Mongkolsapaya et al., "Original Antigenic Sin and Apoptosis in the Pathogenesis of Dengue Hemorrhagic Fever," *Nature Medicine* 9(7):921-927, 2003.
Money et al., "Identification of active antiviral compounds against a New York Isolate of West Nile virus," *Antiviral Research* 55(1):107-116, 2002.
Moulton et al., Abstracts of Papers Amer. Chem. Soc. Nat'l Meeting 226 (1-2); Biol. 75, Sep. 7-11, 2003.
Moulton et al., "HIV Tat Peptide Enhances Cellular Delivery of Antisense Morpholino Oligomers," *Antisense & Nucleic Acid Drug Dev.* 13:31-43, 2003.
Moulton et al., "Cellular Uptake of Antisense Morpholino Oligomers Conjugated to Arginine-Rich Peptides," *Bioconjugate Chem.* 15(2):290-299, 2004.
NCBI Genbank Nucleotide Accession No. AF091736, VESV-like calicivirus strain Pan-1, complete genome, 1998, 5 pages.
NCBI Genbank Nucleotide Accession No. AF169005, Hepatitis C virus subtype 2a isolate NDM59, complete genome, 1999, 5 pages.
National Center for Biotechnology Information Report No. AF029248 from NCBI Genome Database, 2000.
National Center for Biotechnology Information Report No. NC002645 from NCBI Genome Database, 2001.
National Center for Biotechnology Information Report No. AY274119 from NCBI Genome Database, 2003.
Nelson et al., "Arignine-Rich Peptide Conjugation to Morpholino Oligomers: Effects on Antisense Activity and Specificity," *Bioconjug. Chem.* 16(4):959-966, 2005.
Neuman et al., "Antisense Morpholino-Oligomers Directed against the 5' end of the Genome Inhibit Coronavirus Proliferation and Growth," *J. Virology* 78(11):5891-5899, 2004.
O'Ryan, *Clinical Virology Manual*, S. Spector and G. Lancz. New York, Elsevier Science, pp. 361-396, 1992.
Orr et al., "Patent Review: Therapeutic Applications for Antisense Oligonucleotides 1999-2000," Current Opinion in Molecular Therapeutics: *Current Drugs* 2(3):325-331, 2000.
Palù et al., "In Pursuit of New Developments for Gene Therapy of Human Diseases," *J. Biotech.* 68:1-13, 1999.
Pardigon and Strauss, "Cellular Proteins Bind to the 3' End of Sindbis Virus Minus-Strand RNA," *J. Virol.* 66(2):1007-115, 1992.
Pardigon et al., "Multiple Binding Sites for Cellular Proteins in the 3' End of Sindbis Alphavirus Minus-Sense RNA," *J. Virol.* 67(8):5003-5011, 1993.
Partridge et al., "A Simple Method for Delivering Morpholino Antisense Oligos into the Cytoplasm of Cells," *Antisense Nucleic Acid Drug Dev.* 6(3):169-175, 1996.
Paul, "Possible Unifying Mechanism of Picornavirus Genome Replication," *Molecular Biology of Picornaviruses*, B.L. Semier and E. Wimmer, Washington, DC, ASM Press:227-246, 2002.
Patzel et al., "A theoretical approach to select effective antisense oligodeoxyribonucleotides at high statistical probability," *Nucleic Acids Research* 27(22):4328-4334, 1999.
Peters et al., "An Introduction to Ebola: the Virus and the Disease," *J. Infectious Diseases* 179(suppl 1):ix-xvi, 1999.
Proutski et al., "Secondary Structures of the 3' Untranslated Region of Flaviviruses Similarities and Differences," *Nucleic Acids Research* 25(6):1194-1202, 1997.
Raviprakash et al., "Inhibition of Dengue Virus by Novel, Modified Antisense Oligonucleotides," *J. Virology* 69(1):69-74, 1995.
Robaczewska et al., "Inhibition of Hepadnaviral Replication by Polyethylenimine-Based Intravenous Delivery of Antisense Phosphodiester Oligodeoxynucleotides to the Liver," *Gene Therapy* 8:874-881, 2001.
Roehl et al., "Poliovirus Infection Enhances the Formation of Two Ribonucleoprotein Complexes at the 3' End of Viral Negative-Strand RNA," *J. Virol.* 69(5):2954-2961, 1995.
Roehl et al., "Processing of a Cellular Polypeptide by 3CD Proteinase is Required for Poliovirus Ribonucleoprotein Complex Formation," *J. Virol.* 71(1):578-585, 1997.

(56) References Cited

OTHER PUBLICATIONS

Rothbard et al., "Arginine-Rich Molecular Transporters for Drug Delivery: Role of Backbone Spacing in Cellular Uptake," *J. Med. Chem.* 45:3612-3618, 2002.
Sanchez et al, "Sequence Analysis of the Ebola Virus Genome: Organization, Genetic Elements, and Comparison with the Genome of Marburg Virus," *Virus Res.* 29(3):215-240, 1993.
Sankar et al., "Antisense Oligonucleotide Inhibition of Encephalomyocarditis Virus RNA Translation," *European Journal of Biochem.* 184(1):39-45, 1989.
Scanlon, "Anti-Genes: siRNA, Ribozymes and Antisense," *Current Pharmaceutical Biotechnology* 5(5):415-420, 2004.
Scherret et al., "The Relationships between West Nile and Kunjin Viruses," *Emerging Infectious Diseases* 7(4):697-705, 2001.
Schuster et al., "Secondary Structure of the 3' Terminus of Hepatitis C Virus Minus-Strand RNA," *Journal of Virology* 76(16):8058-8068, 2002.
Shabbits et al., "Tumor Chemosensitization Strategies Based on Apoptosis Manipulations," *Mol. Cancer Ther.* 2(8):805-813, 2003.
Shengqi et al., "Synthesis of Antisense Phosphothioate Oligodeoxynucleotides of Dengue Fever Virus and Their Anti-Viral Activity," *Prog. Biochem. and Biophys.* 24:64-88 (English Translation), 1997.
Shi, "Strategies for the Identification of Inhibitors of West Nile Virus and Other Flaviviruses," *Current Opinion in Investigational Drugs* 3(11):1567-1573, 2002.
Siprashvili et al., "Gene Transfer via Reversible Condensation with Cysteine-Flanked, Internally Spaced Arginine-Rich Peptides," *Human Gene Therapy* 14:1225-1233, 2003.
Smith et al., "Calcivirus Emergence from Ocean Reservoirs: Zoonotic and Interspecies Movements," *Emerg. Infect. Dis.* 4(1):13-20, 1998.
Smith et al., "Antisense Treatment of *Caliciviridae*: An Emerging Disease Agent of Animals and Humans," *Cur. Opinion Mol. Ther.* 4(2):177-184, 2002.
Smith and Wu. "Secondary Structure and Hybridization Accessibility of the Hepatitis C Virus Negative Strand RNA 5'-Terminus," *J. Viral Hepatitis* 11:115-123, 2004.
Sosnovtsev and Green, "RNA Transcripts Derived from a Cloned Full-Length Copy of the Feline Calicivirus Genome do not Require VpG for Infectivity," *Virology* 210:383-390, 1995.
Stein et al., "Inhibition of Vesivirus Infections in Mammalian Tissue Culture with Antisense Morpholino Oligomers," *Antisense & Nucleic Acid Drug. Dev.* 11(5):317-325, 2001.
Stein et al., "A Specificity Comparison of Four Antisense Types: Morpholino, 2'-O-Methyl RNA, DNA, and Phosphorothioate DNA," *Antisense & Nucleic Acid Drug Dev.* 7:151-157, 1997.
Stein et al., "Oligonucleotide Compound and Method for Treating Nidovirus Infections," U.S. Appl. No. 11/432,155, filed May 10, 2006, 71 pages.
Stein et al., "Antisense Antiviral Agent and Method for Treating ssRNA Viral Infection," Office Action dated Feb. 17, 2010, U.S. Appl. No. 11/431,968, 19 pages.
Summerton, "Morpholino, siRNA, and S-DNA Compared: Impact of Structure and Mechanism of Action on Off-Target Effects and Sequence Specificity," *Current Topics in Medicinal Chemistry* 7:651-660, 2007.
Summerton et al., "Morpholino and Phosphorothioate Antisense Oligomers Compared in Cell-Free and In-Cell Systems," *Antisense & Nucleic Acid Drug Dev.* 7:63-70, 1997.
Summerton et al., "Morpholino Antisense Oligomers: Design, Preparation, and Properties," *Antisense & Nucleic Acid Drug Dev.* 7(3):187-195, 1997.
Summerton et al. "Morpholino Antisense Oligomers: The Case for an RNase H-Independent Structural Type," *Biochim et Biophys. ACTA* 1489:141-158, 1999.
Taylor et al., "Antisense Oligonucleotides: A Systematic High-Throughput Approach to Target Validation and Gene Function Determination," *Drug Disc. Today* 4:562-567, 1999.
Ternovoi et al., "Tick-Borne Encephalitis with Hemorrhagic Syndrome, Novosibirsk Region, Russia, 1999" *Emerging Infectious Diseases* 9(6):743-746, 2003.
Thiel et al., "Infectious DNA Transcribed in vitro from a cDNA Copy of the Human Coronavirus Genome Cloned in Vaccinia Virus" *J. Gen. Virology* 82:1273-1281, 2001.
Toulme et al., "Targeting RNA Structures by Antisense Oligonucleotides," *Biochimie* 78(7):663-673, 1996.
Uhlmann et al., "Antisense Oligonucleotides: A New Therapeutic Principle," *Chemical Reviews* 90(4):544-584, 1990.
Vickers et al., "Effects of RNA Secondary Structure on Cellular Antisense Activity," *Nucleic Acids Res.* 28(6):1340-1347, 2000.
Vlasov et al., "Inhibition of the Influenza Virus M Protein mRNA Translation in vitro with Complementary Oligonucleotides," *Nucleosides and Nucleotides* 10(1-3):649-650, 1991.
Wages et al., "Affinity Purification of RNA: Sequence-Specific Capture by Nonionic Morpholino Probes," *Biotechniques* 23:1116-1121, 1997.
Wakita et al., "Antiviral Effects of Antisense Rna on Hepatitis C Virus RNA Translation and Expression," *Journal of Medical Virology* 57:217-222, 1999.
Wang et al., "Specific Inhibition of Coxsackievirus B3 Translation and Replication by Phosphorothioate Antisense Oligodeoxynucelotides," *Antimicrobial Agents and Chemotherapy* 45(4):1043-1052, 2001.
Warfield et al., "Role of Natural Killer Cells in Innate Protection Against Lethal Ebola Virus Infection," *J. Exper. Med.* 200(2):169-179, 2004.
Wei et al., "Human Immunodeficiency Virus Type-1 Reverse Transcription Can be Inhibited in vitro by Oligonucleotides that Target Both Natural and Synthetic tRNA Primers," *Nucleic Acids Res.* 28:3065-3074, 2000.
Weller et al., "Oligonucleotide Analogs Having Cationic Intersubunit Linkages," Office Action dated Aug. 18, 2010, U.S. Appl. No. 11/801,885, 6 pages.
Weller et al., "Oligonucleotide Analogs Having Cationic Intersubunit Linkages," Advisory Action dated Oct. 28, 2010, U.S. Appl. No. 11/801,885, 6 pages.
Williams et al., "A Single Intra-Articular Injection of Liposomally Conjugated Methotrexate Suppresses Joint Inflammation in Rat Antigen-Induced Arthritis," *British J. Rheum.* 35(8):719-724,1996.
Wilson et al., "Naturally Occurring Dicistronic Cricket Paralysis Virus RNA is Regulated by Two Internal Ribosome Entry Sites," *Mol. Cell. Biol.* 20(14):4990-4999, 2000.
Wu et al., "Receptor-Mediated in vitro Gene Transformation by a Soluble DNA Carrier System," *J. Biol. Chem.* 262(10):4429-4432, 1987.
Wu et al., "Specific Inhibition of Hepatitis B Viral Gene Expression in vitro by Targeted Antisense Oligonucleotides," *J. Biol. Chem.* 267:12436-12439, 1992.
Xu et al., "Viral Haemorrhagic Disease of Rabbits in the People's Republic of China: Epidemiology and Virus Characterisation," *Rev. Sci. Tech.* 10(2):393-408, 1991.
You et al., "In Vitro RNA Synthesis from Exogenous Dengue Viral RNA Templates Requires Long Range Interactions between 5'- and 3'-Terminal Regions That Influence RNA Structure," *The Journal of Biological Chemistry* 276(19): 15581-15591, 2001.
Yuan et al., "A Phosphorothioate Antisense Oligodeoxynucleotide Specifically Inhibits Coxsackievirus B3 Replication in Cardiomyocytes and Mouse Hearts," *Lab. Investigation* 84:703-714, 2004.
Zeng et al., "Identification of Specific Nucleotide Sequences within the Conserved 3'-SL in the Dengue Type 2 Virus Genome Required for Replication," *J. Virology* 72(9):7510-7522, 1998.
Zhang et al., "Antisense Oligonucleotide Inhibition of Hepatitis C Virus (HCV) Gene Expression in Livers of Mice Infected with an HCV-Vaccinia Virus Recombinant," *Antimicrobial Agents Chemotherapy* 43(2):347-353, 1999.
Zollinger et al., "Meningococcal Vaccines—Present and Future," *Transactions of Royal Soc. of Tropical Med. and Hygiene* 85(Supp. 1):37-43, 1991.
Zuker, "Mfold Web Server for Nucleic Acid Folding and Hybridization Prediction," *Nucleic Acids Res.* 31(13):3406-3415, 2003.

* cited by examiner

ANTISENSE ANTIVIRAL COMPOUND AND METHOD FOR TREATING SS/RNA VIRAL INFECTION

CROSS REFERENCE TO RELATED APPLICATIONS

This application is a continuation of U.S. application Ser. No. 13/335,450, filed on Dec. 22, 2011, now issued as U.S. Pat. No. 8,906,872; which is a continuation of U.S. application Ser. No. 11/432,031, filed on May 10, 2006, now issued as U.S. Pat. No. 8,084,433; which is a continuation-in-part of U.S. application Ser. No. 11/226,995, filed Sep. 14, 2005, now issued as U.S. Pat. No. 8,129,352, which claims the benefit of priority of U.S. Application No. 60/611,063, filed Sep. 16, 2004, each of which is incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing 120178_434C3_SEQUENCE_LISTING. The text file is about 34 KB, was created on Apr. 26, 2015, and is being submitted electronically via EFS-Web.

FIELD OF THE INVENTION

This invention relates to antisense oligonucleotide compounds for use in treating a *Flavivirus, Hepacivirus, Enterovirus, Rhinovirus, Hepatovirus, Aphthovirus, Hepevirus, Coronavirus, Arterivirus, Vesivirus, Norovirus, Mamastrovirus, Alphavirus*, and *Rubivirus* infection and antiviral treatment methods employing the compounds.

REFERENCES

The following references are related to the background of the invention.

Banerjee, R. and A. Dasgupta (2001). “Interaction of picornavirus 2C polypeptide with the viral negative-strand RNA.” *J Gen Virol* 82(Pt 11): 2621-7.

Banerjee, R. and A. Dasgupta (2001). “Specific interaction of hepatitis C virus protease/helicase NS3 with the 3'-terminal sequences of viral positive- and negative-strand RNA.” *J Virol* 75(4): 1708-21.

Banerjee, R., A. Echeverri, et al. (1997). “Poliovirus-encoded 2C polypeptide specifically binds to the 3'-terminal sequences of viral negative-strand RNA.” *J* Virol 71(12): 9570-8.

Banerjee, R., W. Tsai, et al. (2001). “Interaction of poliovirus-encoded 2C/2BC polypeptides with the 3' terminus negative-strand cloverleaf requires an intact stem-loop b.” *Virology* 280(1): 41-51.

Blommers, M. J., U. Pieles, et al. (1994). “An approach to the structure determination of nucleic acid analogues hybridized to RNA. NMR studies of a duplex between 2'-OMe RNA and an oligonucleotide containing a single amide backbone modification.” *Nucleic Acids Res* 22(20): 4187-94.

Gait, M. J., A. S. Jones, et al. (1974). “Synthetic-analogues of polynucleotides XII. Synthesis of thymidine derivatives containing an oxyacetamido- or an oxyformamido-linkage instead of a phosphodiester group.” *J Chem Soc* [*Perkin* 1] 0(14): 1684-6.

Holland, J. (1993). *Emerging Virus*. S. S. Morse. N.Y. and Oxford, Oxford University Press: 203-218.

Lesnikowski, Z. J., M. Jaworska, et al. (1990). “Octa(thymidine methanephosphonates) of partially defined stereochemistry: synthesis and effect of chirality at phosphorus on binding to pentadecadeoxyriboadenylic acid.” *Nucleic Acids Res* 18(8): 2109-15.

Markoff, L. (2003). “5'- and 3'-noncoding regions in flavivirus RNA.” *Adv Virus Res* 59: 177-228.

Mertes, M. P. and E. A. Coats (1969). “Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate.” *J Med Chem* 12(1): 154-7.

Moulton, H. M., M. H. Nelson, et al. (2004). “Cellular uptake of antisense morpholino oligomers conjugated to arginine-rich peptides.” *Bioconjug Chem* 15(2): 290-9.

Murray, R. et al. (1998). Medical Microbiology. St. Louis, Mo., Mosby Press: 542-543.

Neuman, B. W., D. A. Stein, et al. (2004). “Antisense Morpholino-Oligomers Directed against the 5' End of the Genome Inhibit *Coronavirus* Proliferation and Growth{dagger}.” *J. Virol.* 78(11): 5891-5899.

O’Ryan, M. (1992). *Clinical Virology Manual*. S. Spector and G. Lancz. N.Y., Elsevier Science: 361-196.

Pardigon, N., E. Lenches, et al. (1993). “Multiple binding sites for cellular proteins in the 3' end of Sindbis alphavirus minus-sense RNA.” *J Virol* 67(8): 5003-11.

Pardigon, N. and J. H. Strauss (1992). “Cellular proteins bind to the 3' end of Sindbis virus minus-strand RNA.” *J Virol* 66(2): 1007-15.

Paul, A. V. (2002). Possible unifying mechanism of picornavirus genome replication. *Molecular Biology of Picornaviruses*. B. L. Semler and E. Wimmer. Washington, D.C., ASM Press: 227-246.

Roehl, H. H., T. B. Parsley, et al. (1997). “Processing of a cellular polypeptide by 3CD proteinase is required for poliovirus ribonucleoprotein complex formation.” *J Virol* 71(1): 578-85.

Roehl, H. H. and B. L. Semler (1995). “Poliovirus infection enhances the formation of two ribonucleoprotein complexes at the 3' end of viral negative-strand RNA.” *J Virol* 69(5): 2954-61.

Smith, A. W., D. E. Skilling, et al. (1998). “Calicivirus emergence from ocean reservoirs: zoonotic and interspecies movements.” *Emerg Infect Dis* 4(1): 13-20.

Summerton, J. and D. Weller (1997). “Morpholino antisense oligomers: design, preparation, and properties.” *Antisense Nucleic Acid Drug Dev* 7(3): 187-95.

Xu, W. Y. (1991). “Viral haemorrhagic disease of rabbits in the People’s Republic of China: epidemiology and virus characterisation.” *Rev Sci Tech* 10(2): 393-408.

Zuker, M. (2003). “Mfold web server for nucleic acid folding and hybridization prediction.” *Nucleic Acids Res* 31(13): 3406-15.

BACKGROUND OF THE INVENTION

Single-stranded RNA (ssRNA) viruses cause many diseases in wildlife, domestic animals and humans. These viruses are genetically and antigenically diverse, exhibiting broad tissue tropisms and a wide pathogenic potential. The incubation periods of some of the most pathogenic viruses, e.g. the caliciviruses, are very short. Viral replication and expression of virulence factors may overwhelm early defense mechanisms (Xu 1991) and cause acute and severe symptoms.

There are no specific treatment regimens for many viral infections. The infection may be serotype specific and natural immunity is often brief or absent (Murray et al. 1998). Immunization against these virulent viruses is impractical because of the diverse serotypes. RNA virus replicative processes lack effective genetic repair mechanisms, and current estimates of RNA virus replicative error rates are such that each genomic replication can be expected to produce one to ten errors, thus generating a high number of variants (Holland 1993). Often, the serotypes show no cross protection such that infection with any one serotype does not protect against infection with another. For example, vaccines against the vesivirus genus of the caliciviruses would have to provide protection against over 40 different neutralizing serotypes (Smith, Skilling et al. 1998) and vaccines for the other genera of the Caliciviridae are expected to have the same limitations.

Thus, there remains a need for an effective antiviral therapy in several virus families, including small, single-stranded, positive-sense RNA viruses in the Flaviviridae, Picornaviridae, Caliciviridae, Togaviridae, Arteriviridae, Coronaviridae, Astroviridae or Hepeviridae families.

SUMMARY OF THE INVENTION

The invention includes, in one aspect, a method of producing an anti-viral compound effective in inhibiting replication within a host cell of an RNA virus having a single-stranded, positive-sense genome and selected from one of the Flaviviridae, Picornaviridae, Caliciviridae, Togaviridae, Arteriviridae, Coronaviridae, Astroviridae or Hepeviridae families. The method includes first identifying as a viral target sequence, a region within the 5'-terminal 40 bases of the positive strand of the infecting virus whose sequence is capable of forming internal stem-loop secondary structure. There is then constructed, by step-wise solid-phase synthesis, an oligonucleotide analog compound characterized by:

(i) a nuclease-resistant backbone, (ii) capable of uptake by mammalian host cells, (iii) containing between 12-40 nucleotide bases, and (iv) having a targeting sequence of at least 12 subunits that is complementary to the virus-genome region capable of forming internal duplex structure, and (v) an ability to form with the viral target sequence, a heteroduplex structure (i) composed of the positive sense strand of the virus and the oligonucleotide compound, and (ii) characterized by a Tm of dissociation of at least 45° C. and disruption of such stem-loop structure.

The target sequence may be identified by obtaining analyzing the 5'-terminal sequences, e.g., the 5'-terminal 40 bases by a computer program capable of performing secondary structure predictions based on a search for the minimal free energy state of the input RNA sequence.

The invention includes, in another aspect, a method of inhibiting in a mammalian host cell, replication of an infecting RNA virus having a single-stranded, positive-sense genome and selected from one of the Flaviviridae, Picornaviridae, Caliciviridae, Togaviridae, Arteriviridae, Coronaviridae, Astroviridae or Hepeviridae families. The method includes administering to the infected host cells, a virus-inhibitory amount of an oligonucleotide analog compound characterized by:

(i) a nuclease-resistant backbone, (ii) capable of uptake by mammalian host cells, (iii) containing between 12-40 nucleotide bases, and (iv) having a targeting sequence of at least 12 subunits that is complementary to a region within the 5'-terminal 40 bases of the positive-strand viral genome that is capable of forming internal stem-loop secondary structure. The compound is effective, when administered to the host cells, to form a heteroduplex structure (i) composed of the positive sense strand of the virus and the oligonucleotide compound, and (ii) characterized by a Tm of dissociation of at least 45° C. and disruption of such stem-loop secondary structure. The compound may be administered to a mammalian subject infected with the virus, or at risk of infection with the virus.

The compound may be composed of morpholino subunits linked by uncharged, phosphorus-containing intersubunit linkages, joining a morpholino nitrogen of one subunit to a 5' exocyclic carbon of an adjacent subunit. In one embodiment, the intersubunit linkages are phosphorodiamidate linkages, such as those having the structure:

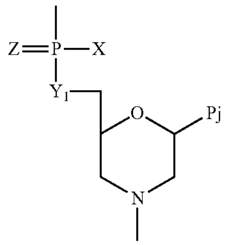

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino, e.g., wherein X=$NR_2$, where each R is independently hydrogen or methyl.

The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The compound may also be a covalent conjugate of an oligonucleotide analog moiety capable of forming such a heteroduplex structure with the positive sense strand of the virus, and an arginine-rich polypeptide effective to enhance the uptake of the compound into host cells.

In a related aspect, the invention includes a heteroduplex complex formed between:

(a) a region within the 5'-terminal 40 bases of the positive strand RNA of an RNA virus having a single-stranded, positive-sense RNA genome and selected from one of the Flaviviridae, Picornaviridae, Caliciviridae, Togaviridae, Arteriviridae, Coronaviridae, Astroviridae or Hepeviridae families, which region is capable of forming internal stem-loop secondary structure, and (b) an oligonucleotide analog compound characterized by:

(i) a nuclease-resistant backbone, (ii) capable of uptake by mammalian host cells, (iii) containing between 12-40 nucleotide bases, (iv) having a targeting sequence of at least 12 subunits that is complementary to a region associated with such stem-loop secondary structure within the 5'-terminal end 40 bases of the positive-sense RNA strand of the virus, where said heteroduplex complex has a Tm of dissociation of at least 45° C. and disruption of such stem-loop secondary structure.

An exemplary compound is composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

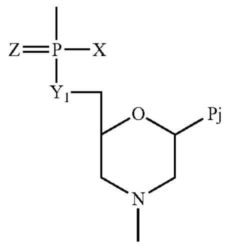

where $Y_1$═O, Z═O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X═$NR_2$, where each R is independently hydrogen or methyl. The compound may be the oligonucleotide analog alone or a conjugate of the analog and an arginine-rich polypeptide capable of enhancing the uptake of the compound into host cells.

The invention is also directed to a method for detecting the presence of a viral infection by an RNA virus having a single-stranded, positive-sense RNA genome and selected from one of the Flaviviridae, Picornaviridae, Caliciviridae, Togaviridae, Arteriviridae, Coronaviridae, Astroviridae or Hepeviridae families a in a mammalian subject, or for confirming the presence of an effective interaction between such a virus infecting a mammalian subject and an antisense oligonucleotide analog compound directed against the virus. In practicing the method, the subject is administered an oligonucleotide analog compound having (a) a sequence of 12-40 subunits, including a targeting sequence of at least 12 subunits that is complementary to a region associated with stem-loop secondary structure within the 5'-terminal end 40 bases of the positive-sense RNA strand of the virus, (b) morpholino subunits linked by uncharged, phosphorus-containing intersubunit linkages, each linkage joining a morpholino nitrogen of one subunit to a 5' exocyclic carbon of an adjacent subunit, and (c) capable of forming with the positive-strand viral ssRNA genome, a heteroduplex structure characterized by a Tm of dissociation of at least 45° C. and disruption of the stem-loop secondary structure.

At a selected time after the compound is administered, a sample of a body fluid is obtained from the subject; and assayed for the presence of a nuclease-resistant heteroduplex comprising the antisense oligonucleotide complexed with a complementary-sequence 5'-end region of the positive-strand RNA of the virus.

In still another aspect, the invention includes an oligonucleotide analog compound for use in inhibiting replication in mammalian host cells of an RNA virus having a single-stranded, positive-sense RNA genome and selected from the Flaviviridae, Picornaviridae, Caliciviridae, Togaviridae, or Coronaviridae families and hepatitis E virus. The compound is characterized by:

(i) a nuclease-resistant backbone, (ii) capable of uptake by mammalian host cells, (iii) containing between 12-40 nucleotide bases, (iv) having a targeting sequence of at least 12 subunits that is complementary to a region associated with stem-loop secondary structure within the 5'-terminal end 40 bases of the positive-sense RNA strand of the virus, and (v) capable of forming with the positive-strand viral ssRNA genome, a heteroduplex structure having a Tm of dissociation of at least 45° C. and disruption of such stem-loop secondary structure.

An exemplary compound is composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

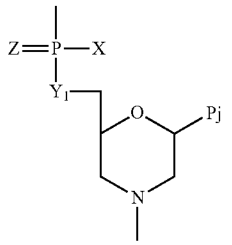

where $Y_1$═O, Z═O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X═$NR_2$, where each R is independently hydrogen or methyl. The compound may be the oligonucleotide analog alone or a conjugate of the analog and an arginine-rich polypeptide capable of enhancing the uptake of the compound into host cells.

For treatment of a *Flavivirus* or *Hepacivirus* as given below, the targeting sequence is complementary to a region associated with stem-loop secondary structure within one of the following sequences:

(i) SEQ ID NO. 1, for St Louis encephalitis virus;

(ii) SEQ ID NO. 2, for Japanese encephalitis virus;

(iii) SEQ ID NO. 3, for a Murray Valley encephalitis virus;

(iv) SEQ ID NO. 4, for a West Nile fever virus;

(v) SEQ ID NO. 5, for a Yellow fever virus (vi) SEQ ID NO. 6, for a Dengue Type-2 virus;

(vii) SEQ ID NO. 7, for a Hepatitis C virus;

(viii) SEQ ID NO. 8, for a tick-borne encephalitis virus;

(ix) SEQ ID NO. 9, for Omsk hemorrhagic fever virus; and (x) SEQ ID NO. 10, for Powassan virus.

Exemplary targeting sequences for these viruses include the following sequences, or portions of these sequences that overlap with one or more regions of duplex secondary structure in the associated target sequence:

(i) SEQ ID NOS. 41 and 42, for St Louis encephalitis virus;

(ii) SEQ ID NOS. 43 and 44, for Japanese encephalitis virus;

(iii) SEQ ID NOS. 45 and 46, for a Murray Valley encephalitis virus;

(iv) SEQ ID NOS. 47 and 48, for a West Nile fever virus;

(v) SEQ ID NOS. 49 and 50, for a Yellow fever virus (vi) SEQ ID NOS. 51, 52, for a Dengue virus;

(vii) SEQ ID NOS. 53 and 54, for a Hepatitis C virus;

(viii) SEQ ID NOS. 55 and 56, for a tick-borne encephalitis virus;

(ix) SEQ ID NOS. 57 and 58, for Omsk hemorrhagic fever virus; and (x) SEQ ID NOS. 59 and 60, for Powassan virus.

For treatment of an *Enterovirus, Rhinovirus, Hepatovirus* or *Aphthovirus* the targeting sequence is complementary to a region associated with stem-loop secondary structure within one of the following sequences:

(i) SEQ ID NO. 11, for a polio virus of the Mahoney and Sabin strains;

(ii) SEQ ID NO. 12, for a Human *Enterovirus* A;

(iii) SEQ ID NO. 13, for a Human *Enterovirus* B;

(iv) SEQ ID NO. 14, for a Human *Enterovirus* C;

(v) SEQ ID NO. 15, for a Human *Enterovirus* D;

(vi) SEQ ID NO. 16, for a Human *Enterovirus* E;

(vii) SEQ ID NO. 17, for a Bovine *Enterovirus;*

(viii) SEQ ID NO. 18, for Human *Rhinovirus* 89;

(ix) SEQ ID NO. 19, for Human *Rhinovirus* B;

(x) SEQ ID NO. 20, for Foot-and-mouth disease virus; and (xi) SEQ ID NO. 21, for a hepatitis A virus.

Exemplary targeting sequences for these viruses include the following sequences, or portions of these sequences that overlap with one or more regions of duplex secondary structure in the associated target sequence:

(i) SEQ ID NOS. 61 and 62, for a polio virus of the Mahoney and Sabin strains;

(ii) SEQ ID NOS. 63 and 64, for a Human *Enterovirus* A;

(iii) SEQ ID NOS. 65 and 66, for a Human *Enterovirus* B;

(iv) SEQ ID NOS. 67 and 68, for a Human *Enterovirus* C;

(v) SEQ ID NOS. 69 and 70, for a Human *Enterovirus* D;

(vi) SEQ ID NOS. 71 and 72, for a Human *Enterovirus* E;

(vii) SEQ ID NOS. 73 and 74, for a Bovine *Enterovirus;*

(viii) SEQ ID NOS. 75 and 76, for Human *Rhinovirus* 89;

(ix) SEQ ID NOS. 77 and 78, for Human *Rhinovirus* B;

(x) SEQ ID NOS. 79 and 80, for Foot-and-mouth disease virus; and (xi) SEQ ID NOS. 81 and 82, for a hepatitis A virus.

For treatment of a Calicivirus or *Norovirus* the targeting sequence is complementary to a region associated with stem-loop secondary structure within one of the following sequences:

(i) SEQ ID NO. 22, for a Feline Calicivirus;

(ii) SEQ ID NO. 23, for a Canine Calicivirus;

(iii) SEQ ID NO. 24, for a Porcine enteric calicivirus;

(iv) SEQ ID NO. 25, for Calicivirus strain NB; and (v) SEQ ID NO. 26, for a Norwalk virus.

Exemplary targeting sequences for these viruses include the following sequences, or portions of these sequences that overlap with one or more regions of duplex secondary structure in the associated target sequence:

(i) SEQ ID NOS. 83 and 84, for a Feline Calicivirus;

(ii) SEQ ID NOS. 85 and 86, for a Canine Calicivirus;

(iii) SEQ ID NOS. 87 and 88, for a Porcine enteric calicivirus;

(iv) SEQ ID NOS. 89 and 90, for Calicivirus strain NB; and (v) SEQ ID NOS. 91 and 92, for a Norwalk virus.

For treatment of the *Hepevirus*, Hepatitis E virus, the targeting sequence is complementary to a region associated with stem-loop secondary structure within the sequence identified as SEQ ID NO: 27. Exemplary targeting sequences include SEQ ID NOS: 93 and 94, or portions thereof that overlap with one or more regions of secondary structure in the associated target sequence.

For treatment of a *Rubivirus* or *Alphavirus* the targeting sequence is complementary to a region associated with stem-loop secondary structure within one of the following sequences:

(i) SEQ ID NO. 28, for Rubella virus;

(ii) SEQ ID NO. 38, for Eastern equine encephalitis virus;

(iii) SEQ ID NO. 39, for Western equine encephalitis virus; and (iv) SEQ ID NO. 40, for Venezuelan equine encephalitis virus.

Exemplary targeting sequences for each of these viruses are identified by the following sequence ID numbers, or portions of these sequences that overlap with one or more regions of duplex secondary structure in the associated target sequence:

(i) SEQ ID NOS. 95 and 96, for Rubella virus;

(ii) SEQ ID NOS. 115 and 116, for Eastern equine encephalitis virus;

(iii) SEQ ID NOS. 117 and 118, for Western equine encephalitis virus; and (iv) SEQ ID NOS. 119 and 120, for Venezuelan equine encephalitis virus For treatment of a *Coronavirus* or *Arterivirus* the targeting sequence is complementary to a region associated with stem-loop secondary structure within one of the following sequences:

(i) SEQ ID NO. 29, for SARS *Coronavirus* TOR2;

(ii) SEQ ID NO. 30, for Porcine epidemic diarrhea virus;

(iii) SEQ ID NO. 31, for Transmissible gastroenteritis virus;

(iv) SEQ ID NO. 32, for Bovine *Coronavirus;*

(v) SEQ ID NO. 33, for Human *Coronavirus* 229E;

(vi) SEQ ID NO. 34, for Murine hepatitis virus; and (vii) SEQ ID NO. 35, for Porcine reproductive and respiratory syndrome virus.

Exemplary targeting sequences for each of these viruses are identified by the following sequence ID numbers, or portions of these sequences that overlap with one or more regions of duplex secondary structure in the associated target sequence:

(i) SEQ ID NOS. 97 and 98, for SARS *Coronavirus* TOR2;

(ii) SEQ ID NOS. 99 and 100, for Porcine epidemic diarrhea virus;

(iii) SEQ ID NOS. 101 and 102, for Transmissible gastroenteritis virus;

(iv) SEQ ID NOS. 103 and 104, for Bovine *Coronavirus;*

(v) SEQ ID NOS. 105 and 106, for Human *Coronavirus* 229E;

(vi) SEQ ID NOS. 107 and 108, for Murine hepatitis virus; and (vii) SEQ ID NOS. 109 and 110, for Porcine reproductive and respiratory syndrome virus.

For treatment of a *Mamastrovirus*, Human astrovirus, the targeting sequence is complementary to a region associated with stem-loop secondary structure within the sequence identified as SEQ ID NO: 37. Exemplary targeting sequences are SEQ ID NOS. 113 and 114, or portions of these sequences that overlap with one or more regions of duplex secondary structure in the associated target sequence.

For treatment of an Equine arteritis virus, the targeting sequence is complementary to a region associated with stem-loop secondary structure within the sequence identified as SEQ ID NO: 36. Exemplary targeting sequences are SEQ ID NOS. 111, 112, or portions of these sequences that overlap with one or more regions of duplex secondary structure in the associated target sequence.

These and other objects and features of the invention will be more fully appreciated when the following detailed description of the invention is read in conjunction with the accompanying figures.

BRIEF DESCRIPTION OF THE DRAWINGS

FIG. 2F shows one preferred cationic backbone linkage.

DETAILED DESCRIPTION OF THE INVENTION

I. Definitions

The terms below, as used herein, have the following meanings, unless indicated otherwise:

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 2A-2D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 1A:
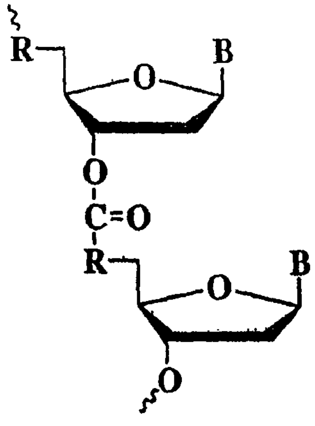
FIGS. 1A-1G show the backbone structures of various oligonucleotide analogs with uncharged backbones.
Figure 1B:
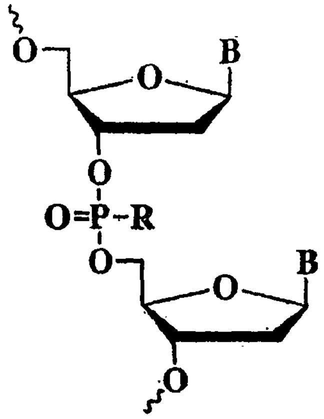
Figure 1C:
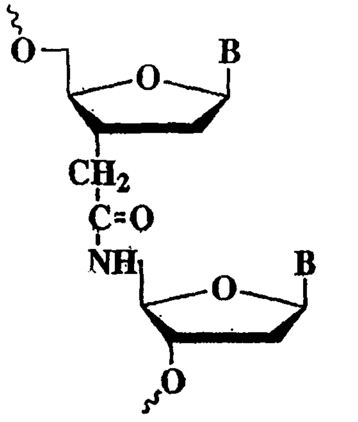
Figure 1D:
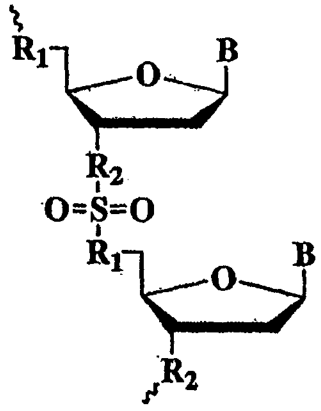
Figure 1E:
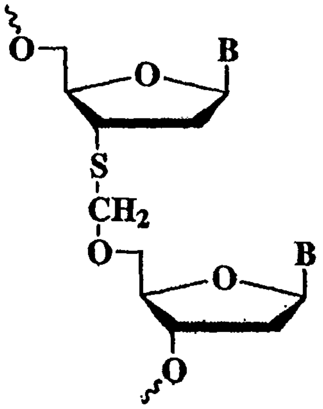
Figure 1F:
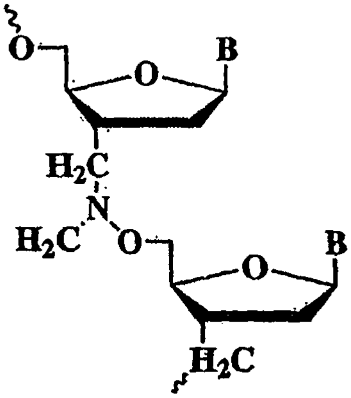
Figure 1G:
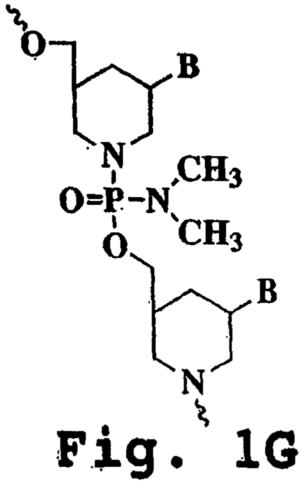
Figure 2A:
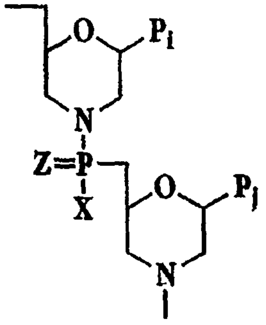
FIGS. 2A-2D show the repeating subunit segment of exemplary morpholino oligonucleotides.
Figure 2B:
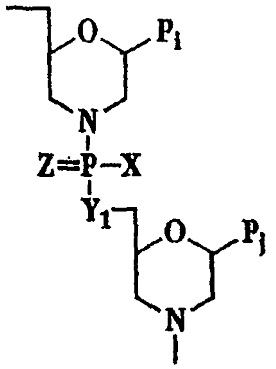
Figure 3A:
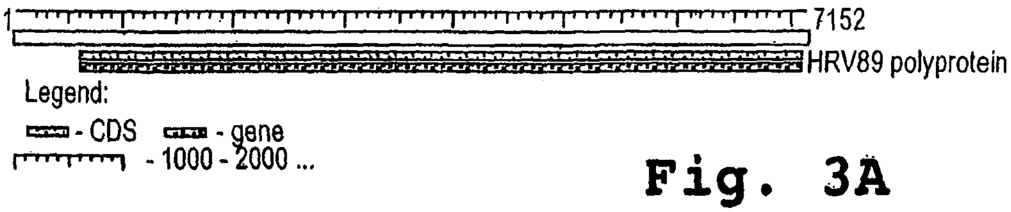
FIGS. 3A-3E are schematic diagrams of genomes of exemplary viruses and viral target sites.
Figure 3B:
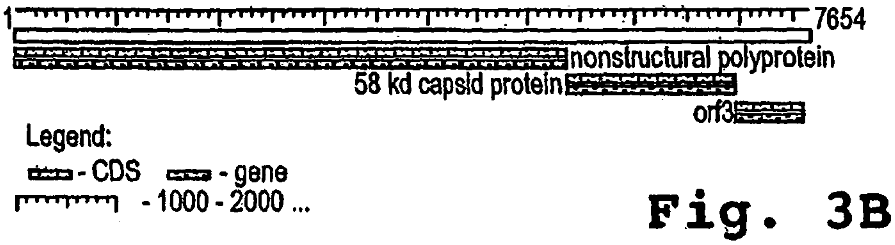

The subunit and linkage shown in FIG. 2B are used for six-atom repeating-unit backbones, as shown in FIG. 3B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_i$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 2B, where $X{=}NH_2$, NHR, or $NR_2$ (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2E. Also preferred are morpholino oligomers where the phosphorodiamidate linkages are uncharged linkages as shown in FIG. 2E interspersed with cationic linkages as shown in FIG. 2F where, in FIG. 2B, X=1-piperazino. In another FIG. 2B embodiment, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to a viral genomic RNA, and specifically, to a region associated with stem-loop secondary structure within the 5'-terminal end 40 bases of the positive-sense RNA strand of a single-stranded RNA (ssRNA) virus described herein.

The term "target sequence" refers to a portion of the target RNA against which the oligonucleotide analog is directed, that is, the sequence to which the oligonucleotide analog will hybridize by Watson-Crick base pairing of a complementary sequence. As will be seen, the target sequence may be a contiguous region of the viral positive-strand RNA, or may be composed of complementary fragments of both the 5' and 3' sequences involved in secondary structure.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. As will be seen, the target and targeting sequences are selected such that binding of the analog to a region within the 5'-terminal end 40 bases of the positive-sense RNA strand of the virus acts to disrupt secondary structure, particularly, the most 3' stem loop structure, in this region.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting ssRNA virus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g., an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, or polyarginine, to facilitate transport into the target host cell as described (Moulton, Nelson et al. 2004). Exemplary arginine-rich peptides useful in practicing the present invention as listed as SEQ ID NOS:121-126 in the Sequence Listing table.

A sequence is "capable of forming internal stem-loop secondary structure" if it can spontaneously, under physiological conditions, form one or more regions of double-stranded (duplex) RNA separated by one or more regions of single-stranded RNA. The stem and loop in this structure refers to the duplex RNA region (stem) terminating in a looped single-stranded region. The stem-loop structure of the 5'-terminal regions of several of the viruses encompassed by the invention are seen in FIGS. 4A-4E. As seen for the West Nile virus (WNV) or HCV, for example (FIG. 4A), the stem-loop structure may comprise a single stem, a single loop, and non-duplexed end regions. In other cases, e.g., Yellow fever virus (YFV) or Dengue-2 virus (FIG. 4A), the stem-loop secondary structure can include two or more double-stranded "stem" regions interspersed by non-duplexed regions and including a single loop.

By "disruption of such stem-loop structure" is meant disruption of any portion of the stem-loop structure in the 5' terminal region of the RNA viral positive-strand genome, by interfering with duplex RNA formation within this region by forming a stable heteroduplex complex between the oligonucleotide analog compound of the invention and duplex-forming sequences within the 5' terminal region of the virus genome. Rules for the selection of targeting sequences capable of disrupting secondary stem-loop structure in the 5'-terminal region of a viral genome are discussed below.

II. Targeted Viruses

The present invention is based on the discovery that effective of single-stranded, positive-sense RNA viruses can be achieved by exposing cells infected with the virus to antisense oligonucleotide analog compounds (i) targeted against the 5' end terminal sequences of the positive-strand viral RNA strand, and in particular, against target sequences that contribute to stem-loop secondary structure in this region, (ii) having physical and pharmacokinetic features which allow effective interaction between the antisense compound and the virus within host cells. In one aspect, the oligomers can be used in treating a mammalian subject infected with the virus.

The invention targets RNA viruses having genomes that are: (i) single stranded, (ii) positive polarity, and (iii) less than 32 kb. The targeted viruses also synthesize a genomic RNA strand with negative polarity, the minus-strand or negative-sense RNA, as the first step in viral RNA replication. In particular, targeted viral families include Flaviviridae, Picornaviridae, Caliciviridae, Togaviridae, Arteriviridae, Coronaviridae, Astroviridae and Hepeviridae families. Targeted viruses organized by family, genus and species are listed in Table 1. Various physical, morphological, and biological characteristics of each of these eight families, and members therein, can be found, for example, in Textbook of Human Virology, R. Belshe, ed., 2nd Edition, Mosby, 1991 and at the Universal Virus Database of the International Committee on Taxonomy of Viruses (www.ncbi.nlm.nih.gov/ICTVdb/index.htm). Some of the key biological characteristics of each family are summarized below.

A. Flaviviridae.

Members of this family include several serious human pathogens, among them mosquito-borne members of the genus *Flavivirus* including yellow fever virus (YFV), West Nile virus (WNV), Japanese encephalitis virus (JEV), St. Louis encephalitis virus (SLEV), Murray Valley encephalitis, Kunjin virus, and the four serotypes of dengue virus (DEN1-4).

Tick-borne members of the *Flavivirus* genus include tick-borne encephalitis virus (TBEV) and related viruses including Omsk hemorrhagic fever virus (OHFV), Louping ill virus, Powassan virus, Kyasanur Forest disease virus and Alkhurma virus.

The Flaviviridae also includes Hepatitis C virus, a member of the genus *Hepacivirus*.

B. Picornaviridae.

This medically important family, whose members infect both humans and animals, can cause severe paralysis (paralytic poliomyelitis), aseptic meningitis, hepatitis, pleurodynia, myocarditis, skin rashes, and colds; unapparent infection is common. Several medically important genera are members of this family; *Enterovirus* including poliovirus (PV) and human Enteroviruses (e.g. coxsackie viruses); *Hepatovirus* which includes hepatitis A virus (HAV); Rhinoviruses; and Aphthoviruses which include the foot- and mouth disease virus (FMDV).

Rhinoviruses such as human rhinovirus 89 (HRV-89) and human rhinovirus B (HRV-B) are recognized as the principle cause of the common cold in humans. Serotypes are designated from 1A to 100. Transmission is primarily by the aerosol route and the virus replicates in the nose.

Like all positive-sense RNA viruses, the genomic RNA of Picornaviruses is infectious; that is, the genomic RNA is able to direct the synthesis of viral proteins directly, without host transcription events.

C. Caliciviridae.

Members of the Caliciviridae infect both humans and animals. The genus *Vesivirus* produces disease manifestations in mammals that include epithelial blistering and are suspected of being the cause of animal abortion storms and some forms of human hepatitis (non A through E) (Smith et al., 1998). Other genera of the Caliciviridae include the Norwalk-like and Sapporo-like viruses, which together comprise the human caliciviruses, and the Lagoviruses, which include rabbit hemorrhagic disease virus, a particularly rapid and deadly virus.

The human caliciviruses are the most common cause of viral diarrhea outbreaks worldwide in adults, as well as being significant pathogens of infants (O'Ryan 1992). There are at least five types of human caliciviruses that inhabit the gastrointestinal tract. The Norwalk virus is a widespread human agent causing acute epidemic gastroenteritis and causes approximately 10% of all outbreaks of gastroenteritis in man (Murray and al. 1998).

Vesiviruses are now emerging from being regarded as somewhat obscure and host specific to being recognized as one of the more versatile groups of viral pathogens known. For example, a single serotype has been shown to infect a diverse group of 16 different species of animals that include a saltwater fish (opal eye), sea lion, swine, and man.

D. Togaviridae.

Members of this family include the mosquito-borne viruses which infect both humans and animals. The family includes the genera *Alphavirus* and *Rubivirus* (rubella). Representative Alphaviruses include Sindbis, Western equine encephalomyelitis virus (WEEV), Eastern equine encephalitis virus (EEEV) and Venezuelan equine encephalitis virus (VEEV).

E. Hepatitis E-Like Viruses.

Hepatitis E virus (HEV) was initially described in 1987 and first reported in the U.S. in 1991. The virus was initially described as a member of the Caliciviridae based on the small, single-stranded RNA character. Some still classify HEV as belonging to the Caliciviridae, but it has also been recently classified as the only member of the Hepeviridae family. Infection appears to be much like hepatitis A viral infection. The disease is an acute viral hepatitis which is apparent about 20 days after initial infection, and the virus may be observed for about 20 days in the serum. Transmission occurs through contaminated water and geographically the virus is restricted to less developed countries.

F. Coronaviridae, Arteriviridae and Astroviridae.

Members of the Coronaviridae include the human coronaviruses that cause 10 to 30% of common colds and other respiratory infections, and murine hepatitis virus. More recently, the viral cause of severe acute respiratory syndrome (SARS) has been identified as a coronavirus. The Arteriviridae include two important animal viruses, Equine arteritis virus (EAV) and porcine reproductive and respiratory syndrome virus (PRRSV). The Astroviridae includes the human astrovirus (HAstV).

Table 1, below, lists the targeted viruses of the invention organized by family and genus.

| Family | Genus | Virus |
|---|---|---|
| Flaviviridae | *Flavivirus* | St. Louis encephalitis (SLEV) |
| | | Japanese encephalitis (JEV) |
| | | Murray Valley encephalitis (MVEV) |
| | | West Nile (WNV) |
| | | Yellow fever (YFV) |
| | | Dengue Types 1-4 (DEN1-4) |
| | | Tick-borne encephalitis (TBEV) |
| | | Omsk hemorrhagic fever (OHFV) |
| | | Powassan |
| | *Hepacivirus* | Hepatitis C (HCV) |
| Picornaviridae | *Enterovirus* | Poliovirus (PV) |
| | | Human enterovirus A (HEV-A) |
| | | Human enterovirus B (HEV-B) |
| | | Human enterovirus C (HEV-C) |
| | | Human enterovirus D (HEV-D) |
| | | Human enterovirus E (HEV-E) |
| | | Bovine enterovirus (BEV) |
| | *Rhinovirus* | Human Rhinovirus B (HRV-B) |
| | | Human Rhinovirus 89 (HRV-89) |
| | *Apthovirus* | Foot and mouth disease (FMDV) |
| | *Hepatovirus* | Hepatitis A (HAV) |
| Caliciviridae | *Vesivirus* | Feline calicivirus (FCV) |
| | | Canine calicivirus (CaCV) |
| | | Porcine enteric calcivirus (PoCV) |
| | | Calicivirus strain NB (CVNB) |
| | *Norovirus* | Norwalk(NV) |
| Hepeviridae | *Hepevirus* | Hepatitis E (HEV) |
| Togaviridae | *Rubivirus* | Rubella (RUBV) |
| | *Alphavirus* | Eastern equine encephalitis (EEEV) |
| | | Western equine encephalitis (WEEV) |
| | | Venezuelan equine encephalitis (VEEV) |
| Coronaviridae | *Coronavirus* | Porcine epidemic diarrhea (PEDV) |
| | | Transmissible gastroenteritis (TGEV) |
| | | SARS coronavirus (SARS-CoV) |
| | | Bovine coronavirus (BCoV) |
| | | Human coronavirus 229E (HCoV-229E) |
| | | Murine hepatitis (MHV) |
| Arteriviridae | *Arterivirus* | Equine arteritis (EAV) |
| | | Porcine respiratory and reproductive syndrome (PRRSV) |
| Astroviridae | *Mamastrovirus* | Human astrovirus (HAstV) |

III. Viral Target Regions

Single-stranded, positive-sense RNA viruses, like all RNA viruses, are unique in their ability to synthesize RNA on an RNA template. To achieve this task they encode and induce the synthesis of a unique RNA-dependent RNA polymerases (RdRp) and possibly other proteins which bind specifically to the 3' and 5' end terminal untranslated regions (UTRs) of viral RNA. Since viral RNAs are linear molecules, RdRps have to employ unique strategies to initiate de novo RNA replication while retaining the integrity of the 5' end of their genomes. It is generally accepted that positive-strand (+strand) viral RNA replication proceeds via the following pathway:

+strand RNA→−strand RNA synthesis→RF 4→+strand RNA synthesis where "−strand RNA" is negative-sense or minus-strand RNA complementary to the "+strand RNA" and "RF" (replicative form) is double-stranded RNA. The minus-strand RNA is used as a template for replication of multiple copies of positive-strand RNA which is destined for either translation into viral proteins or incorporation into newly formed virions. The ratio of positive to minus-strand RNA in poliovirus-infected cells is approximately 50:1 in Hepatitis C-infected cells indicating each minus-strand RNA serves as a template for the synthesis of many positive-strand RNA molecules.

The present invention is based on the discovery that several classes of positive-strand RNA viruses can be effectively inhibited by exposing the viruses to an antisense compound capable of binding to a sequence within the 5' UTR of the virus positive strand, and in particular, to a sequence designed to disrupt one or more of the cis-acting elements (stem-loop structures) within the 5' UTR.

Figure 4A:
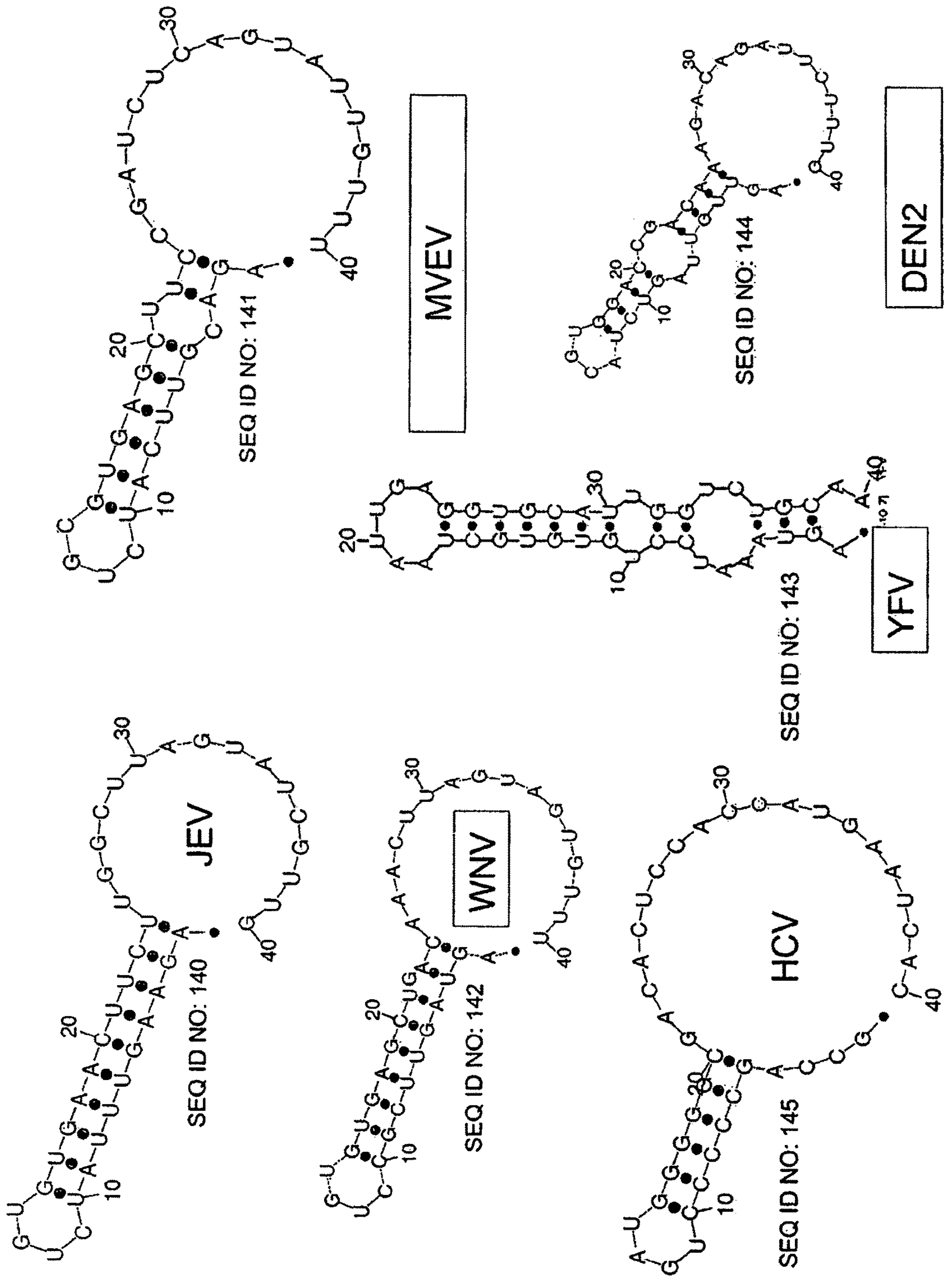
FIGS. 4A-4E show examples of predicted secondary structures of 5' end terminal positive-strand regions for exemplary viruses.
Figure 4B:
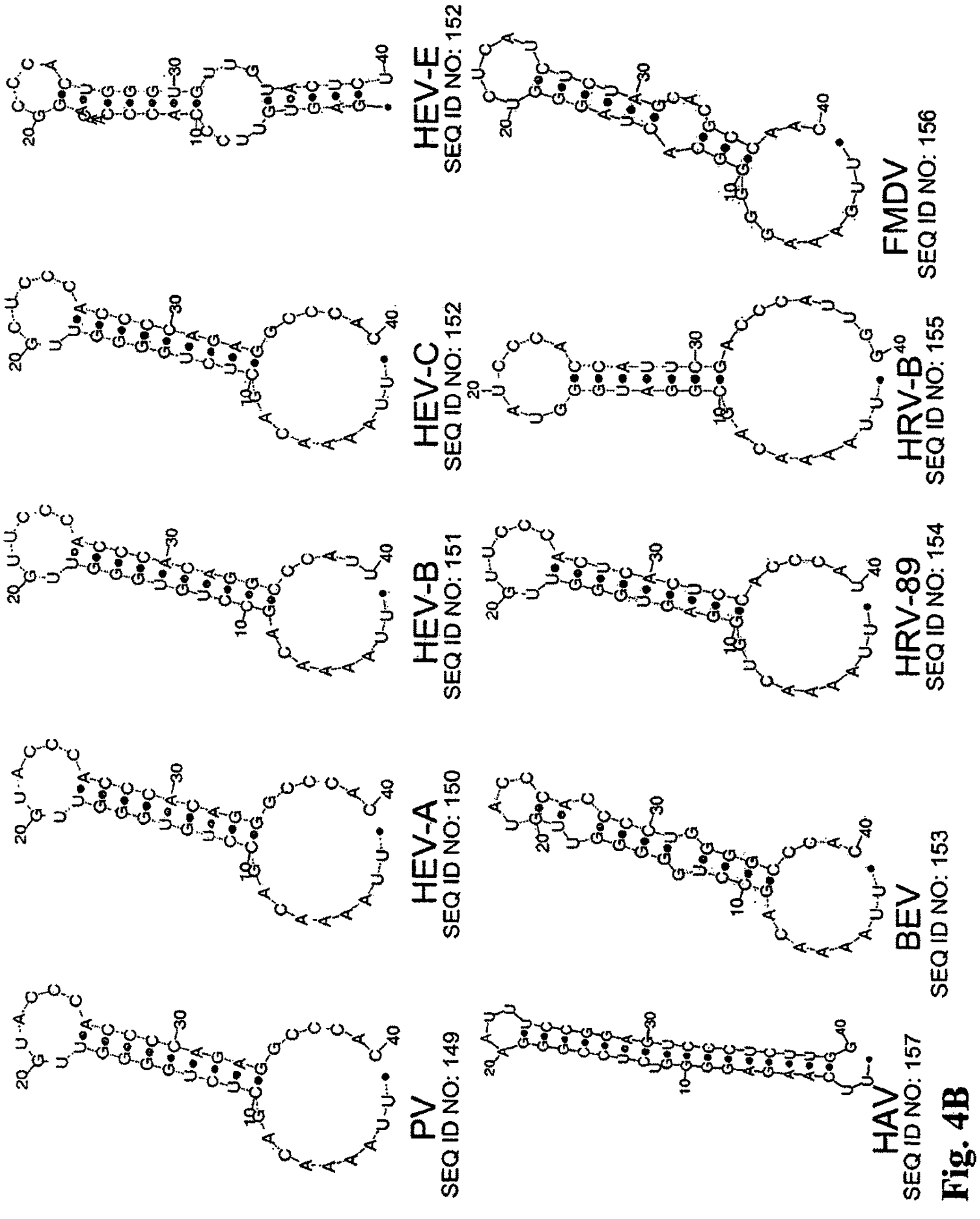
Figure 4C:
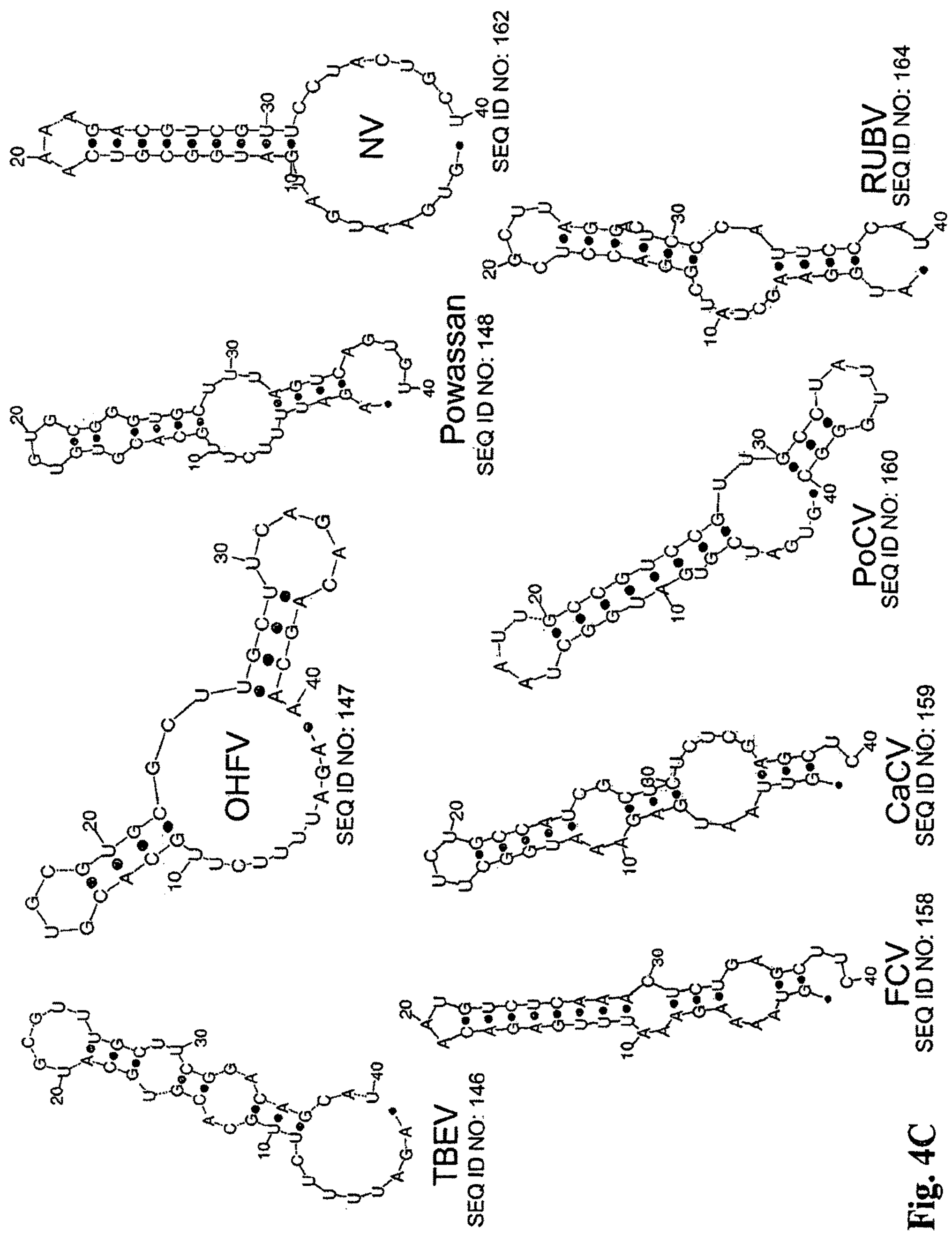
Figure 4D:
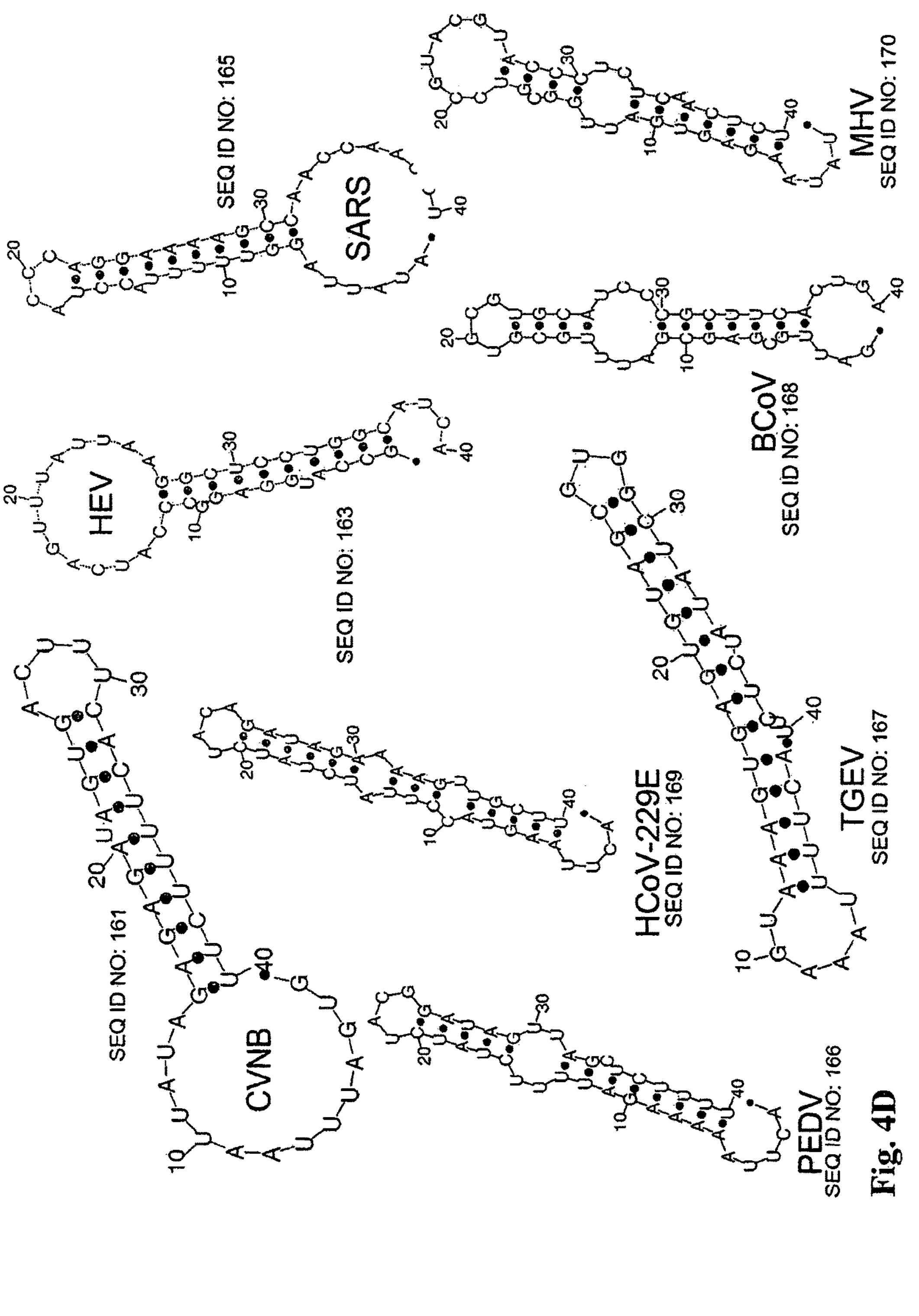
Figure 4E:
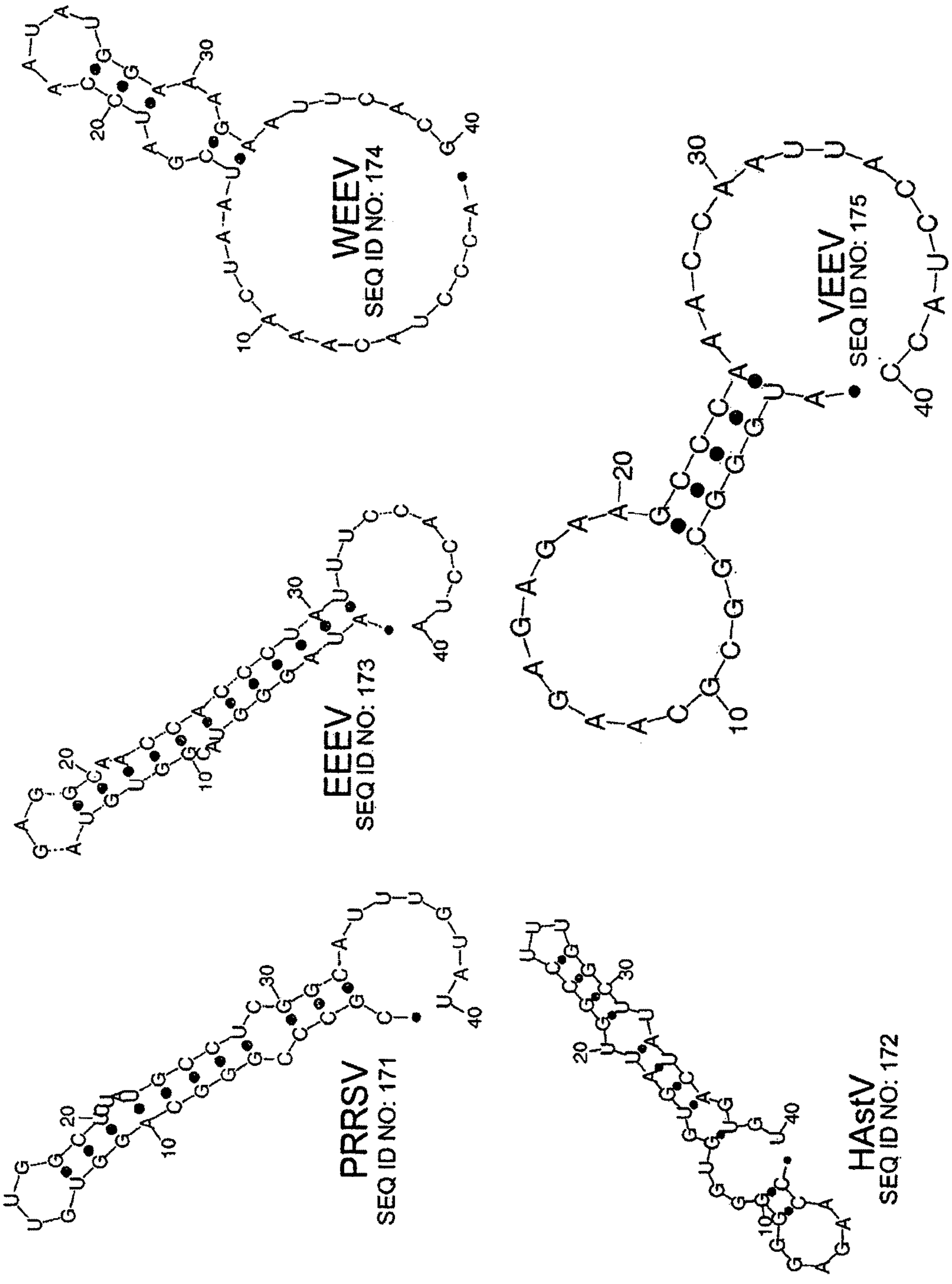

Therefore, as a first step in identifying an effective target region (the sequence in the positive strand 5'-UTR to which the antisense compound will bind), one identifies those regions within the 5'-UTR which are involved in stem-loop secondary structure. This may be done, for example, by computer-assisted secondary structure predictions which are based on a search for the minimal free energy state of the input RNA sequence (Zuker 2003). When this analysis is applied to the terminal 40 bases of the 5'-UTR region of various target viruses, the secondary structures or stem loops shown in FIG. 4A-4E are obtained. As seen, regions of secondary structure (forming the cis-acting elements) are found typically in the terminal 20-25 bases, but in many cases, in bases up to position 40. Therefore, the preferred target sequences are the 5' end terminal regions of the positive-strand RNA that include the end-most 40 nucleotides, typically the 5' terminal 5-35 nucleotides. Preferred target regions include those bases involved in secondary structure in these regions, as indicated in FIGS. 4A-4D. In particular, the targeting sequence contains a sequence of at least 12 bases that are complementary to the 5'-end region of the positive-strand RNA, and are selected such that hybridization of the compound to the RNA is effective to disrupt stem-loop secondary structure in this region, preferably the 5'-end most stem-loop secondary structure. By way of example, FIG. 4A shows secondary structure of viral-genome sequences that are available from well-known sources, such as the NCBI Genbank databases. Alternatively, a person skilled in the art can find sequences for many of the subject viruses in the open literature, e.g., by searching for references that disclose sequence information on designated viruses. Once a complete or partial viral sequence is obtained, the 5' end-terminal sequences of the virus are identified.

The general genomic organization of each of the eight virus families is discussed below, followed by exemplary target sequences obtained for selected members (genera, species or strains) within each family.

A. Picornaviridae.

Typical of the picornaviruses, the human rhinovirus 89 genome (FIG. 3A) is a single molecule of single-stranded, positive-sense, polyadenylated RNA of approximately 7.2 kb. The genome includes a long 618. nucleotide UTR which is located upstream of the first polyprotein, a single ORF, and a VPg (viral genome linked) protein covalently attached to its 5' end. The ORF is subdivided into two segments, each of which encodes a polyprotein. The first segment encodes a polyprotein that is cleaved subsequently to form viral proteins VP1 to VP4, and the second segment encodes a polyprotein which is the precursor of viral proteins including a protease and a polymerase. The ORF terminates in a polyA termination sequence.

B. Caliciviridae.

FIG. 3B shows the genome of a calicivirus; in this case the Norwalk virus. The genome is a single molecule of infectious, single stranded, positive-sense RNA of approximately 7.6 kb. As shown, the genome includes a small UTR upstream of the first open reading frame which is unmodified. The 3' end of the genome is polyadenylated. The genome includes three open reading frames. The first open reading frame encodes a polyprotein, which is subsequently cleaved to form the viral nonstructural proteins including a helicase, a protease, an RNA dependent RNA polymerase, and "VPg", a protein that becomes bound to the 5' end of the viral genomic RNA (Clarke and Lambden, 2000). The second open reading frame codes for the single capsid protein, and the third open reading frame codes for what is reported to be a structural protein that is basic in nature and probably able to associate with RNA.

C. Togaviridae.

Figure 3C:
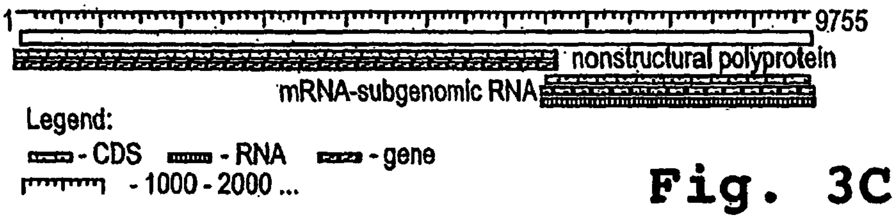

FIG. 3C shows the structure of the genome of a togavirus, in this case, a rubella virus of the *Togavirus* genus. The genome is a single linear molecule of single-stranded, positive-sense RNA of approximately 9.8 kb, which is infectious. The 5' end is capped with a 7-methylG molecule and the 3' end is polyadenylated. Full-length and subgenomic messenger RNAs have been demonstrated, and post translational cleavage of polyproteins occurs during RNA replication. The genome also includes two open reading frames. The first open reading frame encodes a polyprotein which is subsequently cleaved into four functional proteins, nsP1 to nsP4. The second open reading frame encodes the viral capsid protein and three other viral proteins, PE2, 6K and El.

D. Flaviviridae.

Figure 3D:
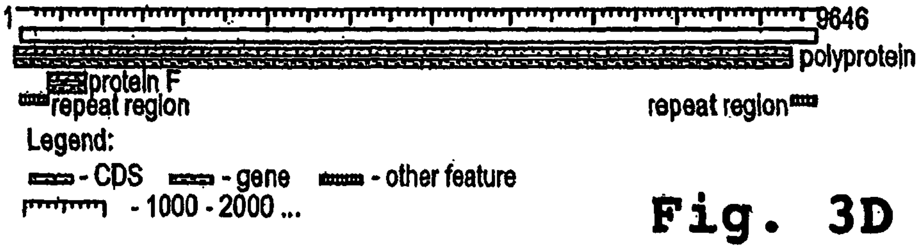

FIG. 3D shows the structure of the genome of the hepatitis C virus of the *Hepacivirus* genus. The HCV genome is a single linear molecule of single-stranded, positive-sense RNA of about 9.6 kb and contains a 341 nucleotide 5' UTR. The 5' end is capped with an $m^7$GppAmp molecule, and the 3' end is not polyadenylated. The genome includes only one open reading frame which encodes a precursor polyprotein separable into six structural and functional proteins.

E. Coronaviridae.

Figure 3E:
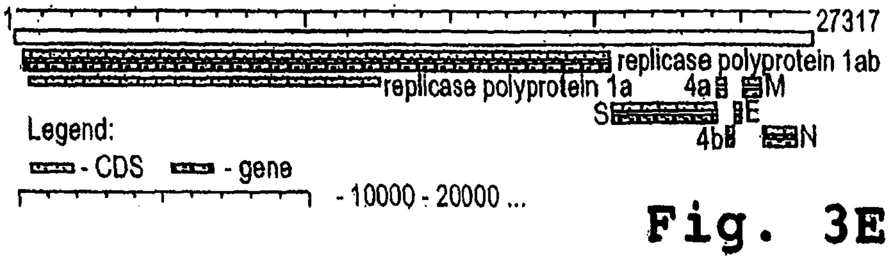

FIG. 3E shows the genome structure of human coronavirus 229E. This coronovirus has a large genome of approximately 27.4 kb that is typical for the Coronaviridae and a 292 nucleotide 5' UTR. The 5'-most ORF of the viral genome is translated into a large polyprotein that is cleaved by viral-encoded proteases to release several nonstructural proteins, including an RdRp and a helicase. These proteins, in turn, are responsible for replicating the viral genome as well as generating nested transcripts that are used in the synthesis of other viral proteins.

GenBank references for exemplary viral nucleic acid sequences representing the 5' end terminal, positive-strand sequences for the first (most 5'-end) 40 bases for corresponding viral genomes are listed in Table 2 below. The nucleotide sequence numbers in Table 2 are derived from the Genbank reference for the positive-strand RNA. It will be appreciated that these sequences are only illustrative of other sequences in the five virus families, as may be available from available gene-sequence databases of literature or patent resources. The sequences below, identified as SEQ ID NOS:1-40, are also listed in Sequence Listing, Table 4, at the end of the specification.

The target sequences in Table 2 are the first 40 bases at the 5' terminal ends of the positive-strands sequences of the indicated viral RNAs. The sequences shown are in the 5' to 3' orientation so the 3' terminal nucleotide is at the end of the listed sequence. The base designation "N" indicates the nucleotides at these positions are presently unknown.

The region within each sequence that is associated with stem-loop secondary structure can be seen from the predicted secondary structures in these sequences, shown in FIGS. 4A-4D.

TABLE 2

Exemplary 5' End Terminal Viral Nucleic Acid Target Sequences

| Virus | Gen-Bank No. | Target Sequence (5' to 3') | SEQ ID NO. |
|---|---|---|---|
| St. Louis encephalitis (SLEV) | M18929 | GNNGATGTTCGCGTC GGTGAGCGGAGAGGA AACAGATTTC | 1 |
| Japanese encephalitis (JEV) | NC 001437 | AGAAGTTTATCTGTG TGAACTTCTTGGCTT AGTATCGTTTG | 2 |
| Murray Valley encephalitis (MVEV) | NC 000943 | AGACGTTCATCTGCG TGAGCTTCCGATCTC AGTATTGTTT | 3 |
| West Nile (WNV) | NC 001563 | AGTAGTTCGCCTGTG TGAGCTGACAAACTT AGTAGTGTTT | 4 |
| Yellow Fever (YFV) | NC 002031 | AGTAAATCCTGTGTG CTAATTGAGGTGCAT TGGTCTGCAA | 5 |
| Dengue- Type 2 (DEN2) | M20558 | AGTTGTTAGTCTACG TGGACCGACAAAGAC AGATTCTTTG | 6 |
| Hepatitis C (HCV) | NC 004102 | GCCAGCCCCCTGATG GGGGCGACACTCCAC CATGAATCAC | 7 |
| Tick-borne encephalitis virus (TBEV) | NC 001672 | AGATTTTCTTGCACG TGCATGCGTTTGCTT CGGACAGCAT | 8 |
| Omsk hemorrhagic fever (OHFV) | NC 005062 | AGATTTTCTTGCACG TGCGTGCGCTTGCTT CAGACAGCAA | 9 |
| Powassan | NC 003687 | AGATTTTCTTGCACG TGTGTGCGGGTGCTT TAGTCAGTGT | 10 |
| Poliovirus-Mahoney strain (PV) | NC 002058 | TTAAAACAGCTCTGG GGTTGTACCCACCCC AGAGGCCCAC | 11 |
| Human Enterovirus A (HEV-A) | NC 001612 | TTAAAACAGCCTGTG GGTTGTACCCACCCA CAGGGCCCAC | 12 |
| Human enterovirus B (HEV-B) | NC 001472 | TTAAAACAGCCTGTG GGTTGTTCCCACCCA CAGGCCCATT | 13 |

TABLE 2-continued

Exemplary 5' End Terminal Viral Nucleic Acid Target Sequences

| Virus | Gen-Bank No. | Target Sequence (5' to 3') | SEQ ID NO. |
|---|---|---|---|
| Human enterovirus C (HEV-C) | NC 001428 | TTAAAACAGCTCTGG GGTTGCTCCCACCCC AGAGGCCCAC | 14 |
| Human enterovirus D (HEV-D) | NC 001430 | TTAAAACAGCTCTGG GGTTGTTCCCACCCC AGAGGCCCAC | 15 |
| Human enterovirus E (HEV-E) | NC 003988 | GAGTGTTCCCACCCA ACAGGCCCACTGGGT GTTGTACTCT | 16 |
| Bovine enterovirus (BEV) | NC 001859 | TTAAAACAGCCTGGG GGTTGTACCCACCCC TGGGGCCCAC | 17 |
| Human rhinovirus 89 (HRV-89) | NC 001617 | TTAAAACTGGGAGTG GGTTGTTCCCACTCA CTCCACCCAT | 18 |
| Human rhinovirus B (HRV-B) | NC 001490 | TTAAAACAGCGGATG GGTATCCCACCATTC GACCCATTGG | 19 |
| Foot-and-mouth disease virus (FMDV) | AY593768 | TTGAAAGGGGGCGCT AGGGTTTCACCCCTA GCATGCCAAC | 20 |
| Hepatitis A (HAV) | NC 001489 | TTCAAGAGGGGTCTC CGGGAATTTCCGGAG TCCCTCTTGG | 21 |
| Feline calicivirus (FCV) | NC 001481 | GTAAAAGAAATTTGA GACAATGTCTCAAAC TCTGAGCTTC | 22 |
| Canine calicivirus (CaCV) | NC 004542 | GTTAATGAGAAATGG CTTCTGCCATCGCTC TCTCGAGCTC | 23 |
| Porcine enteric calicivirus (PoCV) | NC 000940 | GTGATCGTGATGGCT AATTGCCGTCCGTTG CCTATTGGGC | 24 |
| Calicivirus strain NB (CVNB) | NC 004064 | GTGATTTAATTATAG AGAGATAGTGACTTT CACTTTTCTT | 25 |
| Norwalk (NV) | NC 001959 | GTGAATGATGATGGC GTCAAAAGACGTCGT TCCTACTGCT | 26 |
| Hepatitis E (HEV) | NC 001434 | GCCATGGAGGCCCAT CAGTTTATTAAGGCT CCTGGCATCA | 27 |
| Rubella (RUBV) | NC 001545 | ATGGAAGCTATCGGA CCTCGCTTAGGACTC CCATTCCCAT | 28 |
| SARS coronavirus (SARS-CoV) | NC 004718 | ATATTAGGTTTTACC TACCCAGGAAAAGCC AACCAACCT | 29 |
| Porcine epidemic diarrhea (PEDV) | NC 003436 | ACTTAAAAAGATTTT CTATCTACGGATAGT TAGCTCTTTT | 30 |
| Transmissible gastroenteritis (TGEV) | NC 002306 | ACTTTTAAAGTAAAG TGAGTGTAGCGTGGC TATATCTCTT | 31 |

TABLE 2-continued

Exemplary 5' End Terminal Viral Nucleic Acid Target Sequences

| Virus | Gen-Bank No. | Target Sequence (5' to 3') | SEQ ID NO. |
|---|---|---|---|
| Bovine coronavirus (BCoV) | NC 003045 | GATTGCGAGCGATTT GCGTGCGTGCATCCC GCTTCACTGA | 32 |
| Human coronavirus 229E (HCoV-229E) | NC 002645 | ACTTAAGTACCTTAT CTATCTACAGATAGA AAAGTTGCTT | 33 |
| Murine Hepatitis (MHV) | NC 001846 | TATAAGAGTGATTGG CGTCCGTACGTACCC TCTCAACTCT | 34 |
| Porcine reproductive and respiratory syndrome (PRRSV) | AF 176348 | ATGACGTATAGGTGT TGGCTCTATGCCTTG GCATTTGTAT | 35 |
| Equine arteritis (EAV) | NC 002532 | GCTCGAAGTGTGTAT GGTGCCATATACGGC TCACCACCAT | 36 |
| Human astrovirus (HAstV) | NC 001943 | CCAAGAGGGGGGTGG TGATTGGCCTTTGGC TTATCAGTGT | 37 |
| Eastern equine encephalitis (EEEV) | NC 003899 | ATAGGGTACGGTGTA GAGGCAACCACCCTA TTTCCACCTA | 38 |
| Western equine encephalomyelitis (WEEV) | NC 003908 | ACCCTACAAACTAAT CGATCCAATATGGAA AGAATTCACG | 39 |
| Venezuelan equine encephalitis (VEEV) | NC 001449 | ATGGGCGGCGCAAGA GAGAAGCCCAAACCA ATTACCTACC | 40 |

To select a targeting sequence, one looks for a sequence that, when hybridized to a complementary sequence in the 5'-end region of the positive-strand RNA (SEQ ID NOS:1-40), will be effective to disrupt stem-loop secondary structure in this region, and preferably, the initial stem structure in the region. By way of example, a suitable targeting sequence for the West Nile Virus (WNV in FIG. 4A) is a sequence that will disrupt the stem loop structure shown in the figure. Three general classes of sequences would be suitable (exemplary 12-14 base targeting sequences are shown for illustrative purposes):

(1) a sequence such as 5'-ACAGGCGAACTACT-3' (SEQ ID NO: 134) that targets the most 5' bases (1-14) of the stem and surrounding bases;

(2) a sequence such as 5'-GTCAGCTCACAC-3' (SEQ ID NO: 135) that targets the complementary bases of the stem and surrounding bases (13-24);

(3) a sequence such as 5'-GCTCACACAGGCGA-3' (SEQ ID NO: 136), that targets a portion of one or both "sides" of a stem loop and surrounding bases (7-20); typically, the sequence should disrupt all but at least 2-4 of the paired bases forming the stem structure;

It will be appreciated how this selection procedure can be applied to the other sequences shown in Table 2. For example, for the yellow fever virus (YFV) shown in FIG. 4A, exemplary 14-18 base sequences patterned after the three general classes above, might include:

(1) a sequence such as 5'-GCACACAGGATTTACT-3' (SEQ ID NO: 137) that targets the most 5' bases (1-16) of the initial stem and surrounding bases;

(2) a sequence such as 5'-GTCCAATGCACCTC-3' (SEQ ID NO: 138) that targets the complementary bases of the initial stem and surrounding bases (22-35);

(3) a sequence such as 5'-CAATGCACCTCAATTAGC-3' (SEQ ID NO: 139) that targets a portion of both sides of a stem and surrounding bases (15-32);

It will be understood that targeting sequences so selected can be made shorter, e.g., 12 bases, or longer, e.g., 20 bases, and include a small number of mismatches, as long as the sequence is sufficiently complementary to disrupt the stem structure(s) upon hybridization with the target, and forms with the virus positive-strand, a heteroduplex having a $T_m$ of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between the oligomer and the target sequence is a function of the binding $T_m$, and the susceptibility of the duplex to cellular enzymatic cleavage. The $T_m$, of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

The antisense activity of the oligomer may be enhanced by using a mixture of uncharged and cationic phosphorodiamidate linkages as shown in FIGS. 2E and 2F. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g., firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Table 3 below shows exemplary targeting sequences, in a 5'-to-3' orientation, that are complementary to upstream and downstream portions of the 5' terminal 40 base regions of the positive strand of the viruses indicated. The sequences here provide a collection of targeting sequence or sequences from which targeting sequences may be selected, according to the general class rules discussed above. Thus, for example, in selecting a target against St. Louis encephalitis virus, one might select either SEQ ID NOS: 40 or 41, or a portion of either sequence effective to block secondary structure formation in the virus' 5' terminal UTR.

TABLE 3

Exemplary Antisense Sequences Targeting the 5' End Terminal Positive-Strand Regions

| Virus | GenBank Acc. No. | Ncts. | Sequences (5' to 3') | SEQ ID NO. |
|---|---|---|---|---|
| St. Louis encephalitis | M16614 | 1-18 | ACCGACGCGAACATCNNC | 41 |
| | | 11-30 | TCCTCTCCGCTCACCGACGC | 42 |
| Japanese encephalitis | NC 001437 | 1-18 | TCACACAGATAAACTTCT | 43 |
| | | 11-30 | AAGCCAAGAAGTTCACACAG | 44 |
| Murray Valley encephalitis | NC 000943 | 1-18 | TCACGCAGATGAACGTCT | 45 |
| | | 11-30 | GAGATCGGAAGCTCACGCAG | 46 |

TABLE 3-continued

Exemplary Antisense Sequences Targeting the 5' End Terminal Positive-Strand Regions

| Virus | GenBank Acc. No. | Ncts. | Sequences (5' to 3') | SEQ ID NO. |
|---|---|---|---|---|
| West Nile | NC 001563 | 1-20 | GCTCACACAGGCGAACTACT | 47 |
| | | 11-31 | TAAGTTTGTCAGCTCACACAG | 48 |
| Yellow Fever | NC 002031 | 1-22 | CAATTAGCACACAGGATTTACT | 49 |
| | | 21-40 | TTGCAGACCAATGCACCTCA | 50 |
| Dengue- Type 2 | M20558 | 1-20 | GTCCACGTAGACTAACAACT | 51 |
| | | 11-30 | GTCTTTGTCGGTCCACGTAG | 52 |
| Hepatitis C | NC 004102 | 1-17 | CCCATCAGGGGGCTGGC | 53 |
| | | 10-29 | TGGAGTGTCGCCCCCATCAG | 54 |
| Tick-borne encephalitis | NC 001672 | 1-20 | ATGCACGTGCAAGAAAATCT | 55 |
| | | 21-40 | ATGCTGTCCGAAGCAAACGC | 56 |
| Omsk hemorrhagic fever | NC 005062 | 1-21 | CACGCACGTGCAAGAAAATCT | 57 |
| | | 13-32 | TGAAGCAAGCGCACGCACGT | 58 |
| Powassan | NC 003687 | 1-20 | ACACACGTGCAAGAAAATCT | 59 |
| | | 21-40 | ACACTGACTAAAGCACCCGC | 60 |
| Poliovirus- Mahoney strain | NC 002058 | 1-24 | GGTACAACCCCAGAGCTGTTTTAA | 61 |
| | | 21-40 | GTGGGCCTCTGGGGTGGGTA | 62 |
| Human enterovirus A | NC 001612 | 1-20 | CAACCCACAGGCTGTTTTAA | 63 |
| | | 21-40 | GTGGGCCCTGTGGGTGGGTA | 64 |
| Human enterovirus B | NC 001472 | 1-20 | CAACCCACAGGCTGTTTTAA | 65 |
| | | 21-40 | AATGGGCCTGTGGGTGGGAA | 66 |
| Human enterovirus C | NC 001428 | 1-20 | CAACCCCAGAGCTGTTTTAA | 67 |
| | | 21-40 | GTGGGCCTCTGGGGTGGGAG | 68 |
| Human enterovirus D | NC 001430 | 1-20 | CAACCCCAGAGCTGTTTTAA | 69 |
| | | 21-40 | GTGGGCCTCTGGGGTGGGTA | 70 |
| Human enterovirus E | NC 003988 | 1-20 | CCTGTTGGGTGGGAACACTC | 71 |
| | | 21-40 | AGAGTACAACACCCAGTGGG | 72 |
| Bovine enterovirus | NC 001859 | 1-20 | CAACCCCCAGGCTGTTTTAA | 73 |
| | | 21-40 | GTGGGCCCCAGGGGTGGGTA | 74 |
| Human rhinovirus 89 | NC 001617 | 1-20 | CAACCCACTCCCAGTTTTAA | 75 |
| | | 21-40 | ATGGGTGGAGTGAGTGGGAA | 76 |
| Human rhinovirus B | NC 001490 | 1-20 | ATACCCATCCGCTGTTTTAA | 77 |
| | | 21-40 | CCAATGGGTCGAATGGTGGG | 78 |
| Foot-and-mouth disease | AY593768 | 1-21 | AACCCTAGCGCCCCCTTTCAA | 79 |
| | | 21-40 | GTTGGCATGCTAGGGGTGAA | 80 |
| Hepatitis A | NC 001489 | 1-20 | TCCCGGAGACCCCTCTTGAA | 81 |
| | | 21-40 | CCAAGAGGGACTCCGGAAAT | 82 |
| Feline calicivirus | NC 001481 | 1-20 | TTGTCTCAAATTTCTTTTAC | 83 |
| | | 21-40 | GAAGCTCAGAGTTTGAGACA | 84 |
| Canine calicivirus | NC 004542 | 1-20 | AGAAGCCATTTCTCATTAAC | 85 |
| | | 21-40 | GAGCTCGAGAGAGCGATGGC | 86 |
| Porcine enteric calicivirus | NC 000940 | 1-20 | CAATTAGCCATCACGATCAC | 87 |
| | | 13-32 | GGCAACGGACGGCAATTAGC | 88 |
| Calicivirus strain NB | NC 004064 | 1-20 | TCTCTCTATAATTAAATCAC | 89 |
| | | 11-30 | AAAGTCACTATCTCTCTATA | 90 |
| Norwalk | NC 001959 | 1-20 | TTGACGCCATCATCATTCAC | 91 |
| | | 21-40 | AGCAGTAGGAACGACGTCTT | 92 |
| Hepatitis E | NC 001434 | 1-20 | AACTGATGGGCCTCCATGGC | 93 |
| | | 21-40 | TGATGCCAGGAGCCTTAATA | 94 |

TABLE 3-continued

Exemplary Antisense Sequences Targeting the 5' End Terminal Positive-Strand Regions

| Virus | GenBank Acc. No. | Ncts. | Sequences (5' to 3') | SEQ ID NO. |
|---|---|---|---|---|
| Rubella | NC 001545 | 1-20 | CGAGGTCCGATAGCTTCCAT | 95 |
| | | 21-40 | ATGGGAATGGGAGTCCTAAG | 96 |
| SARS coronavirus TOR2 | NC 004718 | 1-20 | GGTAGGTAAAAACCTAATAT | 97 |
| | | 21-40 | AGGTTGGTTGGCTTTTCCTG | 98 |
| Porcine epidemic diarrhea | NC 003436 | 1-20 | GATAGAAAATCTTTTTAAGT | 99 |
| | | 21-40 | AAAAGAGCTAACTATCCGTA | 100 |
| Transmissible gastroenteritis | NC 002306 | 1-20 | ACTCACTTTACTTTAAAAGT | 101 |
| | | 11-30 | GCCACGCTACACTCACTTTA | 102 |
| Bovine coronavirus | NC 003045 | 1-20 | CACGCAAATCGCTCGCAATC | 103 |
| | | 21-40 | TCAGTGAAGCGGGATGCACG | 104 |
| Human coronavirus 229E | NC 002645 | 1-20 | GATAGATAAGGTACTTAAGT | 105 |
| | | 21-40 | AAGCAACTTTTCTATCTGTA | 106 |
| Murine Hepatitis | NC 001846 | 1-21 | CGGACGCCAATCACTCTTATA | 107 |
| | | 18-39 | GAGTTGAGAGGGTACGTACGGA | 108 |
| Porcine reproductive & respiratory syndrome | AF176348 | 5-25 | CATAGAGCCAACACCTATACG | 109 |
| | | 21-40 | ATACAAATGCCAAGGCATAG | 110 |
| Equine arteritis | NC 002532 | 1-20 | GCACCATACACACTTCGAGC | 111 |
| | | 21-40 | ATGGTGGTGAGCCGTATATG | 112 |
| Human astrovirus | NC 001943 | 1-20 | AATCACCACCCCCCTCTTGG | 113 |
| | | 11-30 | GCCAAAGGCCAATCACCACC | 114 |
| Eastern equine encephalitis | NC 003899 | 1-20 | GCCTCTACACCGTACCCTAT | 115 |
| | | 21-40 | TAGGTGGAAATAGGGTGGTT | 116 |
| Western equine encephalomyelitis | NC 003908 | 1-20 | GATCGATTAGTTTGTAGGGT | 117 |
| | | 21-40 | CGTGAATTCTTTCCATATTG | 118 |
| Venezuelan equine encephalitis | NC 001449 | 1-20 | TTCTCTCTTGCGCCGCCCAT | 119 |
| | | 21-40 | GGTAGGTAATTGGTTTGGGC | 120 |

IV. Antisense Oligonucleotide Analog Compounds

A. Properties

As detailed above, the antisense oligonucleotide analog compound (the term "antisense" indicates that the compound is targeted against the virus' sense or positive-sense strand RNA) has a base sequence targeting a region of the 5' end 40 bases that are associated with secondary structure in the negative-strand RNA. In addition, the oligomer is able to effectively target infecting viruses, when administered to a host cell, e.g., in an infected mammalian subject. This requirement is met when the oligomer compound (a) has the ability to be actively taken up by mammalian cells, and (b) once taken up, form a duplex with the target ssRNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

A1. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g., phosphorothioate or N3'→4P5' phosphoramidate linkages, and a comparable number of cationic linkages, such as N,N-diethylenediamine phosphoramidates (Dagle, 2000). The net charge is preferably neutral or at most 1-2 net charges per oligomer.

In addition to being substantially or fully uncharged, the antisense agent is preferably a substrate for a membrane transporter system (i.e., a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition LIPOFECTIN® (Feigner et al., 1987), containing the cationic lipid DOTMA (N-[1-(2,3-dioleyloxyl)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenylalanine and cysteine. The use of arginine-rich peptide-PMO conjugates can be used to enhance cellular uptake of the antisense oligomer (See, e.g. (Moulton, Nelson et al. 2004).

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., ANTISENSE OLIGONUCLEOTIDES: A NEW THERAPEUTIC PRINCIPLE, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

A2. Substantial Resistance to RNaseH

Two general mechanisms have been proposed to account for inhibition of expression by antisense oligonucleotides. (See e.g., Agrawal et al., 1990; Bonham et al., 1995; and Boudvillain et al., 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme et al., 1996), morpholino oligonucleotides, peptide nucleic acids (PNA's), certain 2'-O-allyl or 2'-O-alkyl modified oligonucleotides (Bonham, 1995), and N3'→P5' phosphoramidates (Gee, 1998; Ding, 1996).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

A3. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g., by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as 5' end terminal region of the viral RNA, as described above, the method can be used to detect the presence of a given ssRNA virus, or reduction in the amount of virus during a treatment method.

B. Exemplary oligomer backbones

Examples of nonionic linkages that may be used in oligonucleotide analogs are shown in FIGS. 1A-1F. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (FIG. 1A, R═O) and carbamate (FIG. 1A, R═$NH_2$) linkages (Mertes and Coats 1969; Gait, Jones et al. 1974); alkyl phosphonate and phosphotriester linkages (FIG. 1B, R=alkyl or —O-alkyl) (Lesnikowski, Jaworska et al. 1990); amide linkages (FIG. 1C) (Blommers, Pieles et al. 1994); sulfone and sulfonamide linkages (FIG. 1D, $R_1$, $R_2$═$CH_2$) (Roughten, 1995; McElroy, 1994); and a thioformacetyl linkage (FIG. 1E) (Matteucci, 1990; Cross, 1997). The latter is reported to have enhanced duplex and triplex stability with respect to phosphorothioate antisense compounds (Cross, 1997). Also reported are the 3'-methylene-N-methylhydroxyamino compounds of the structure in FIG. 1F (Mohan, 1995). Also shown is a cationic linkage in FIG. 2F wherein the nitrogen pendant to the phosphate atom in the linkage of FIG. 2E is replaced with a 1-piperazino structure. The method for synthesizing the 1-piperazino group linkages is described below with respect to FIG. 9.

Peptide nucleic acids (PNAs) (FIG. 2E) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 2A-2D. Morpholino oligonucleotides, including antisense oligomers, are detailed, for example, in co-owned U.S. Pat. Nos. 5,698,685, 5,217,866, 5,142,047, 5,034,506, 5,166, 315, 5,185, 444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 2A-2D, each linked by an uncharged, phosphorus-containing subunit linkage. FIG. 2A shows a phosphorus-containing linkage which forms the five atom repeating-unit backbone, where the morpholino rings are linked by a 1-atom phosphoamide linkage. FIG. 2B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 2C:
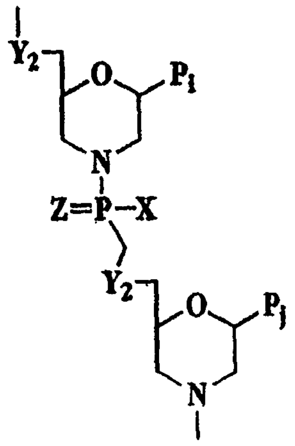
Figure 2D:
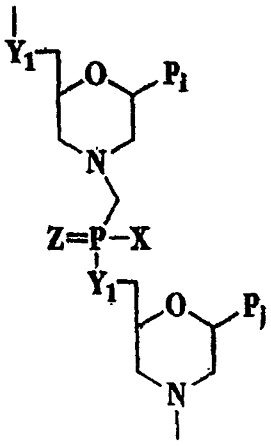
Figure 2E:
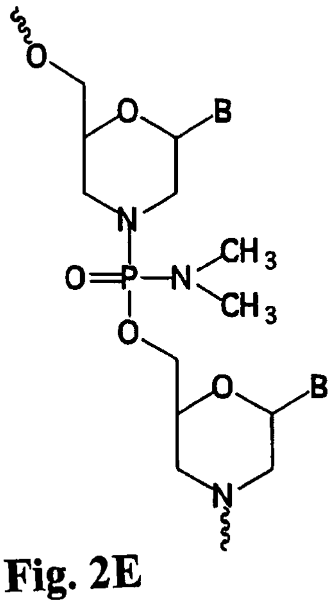
FIGS. 2E-2F show the repeating subunit segment of exemplary morpholino oligonucleotides, where
Figure 2F:
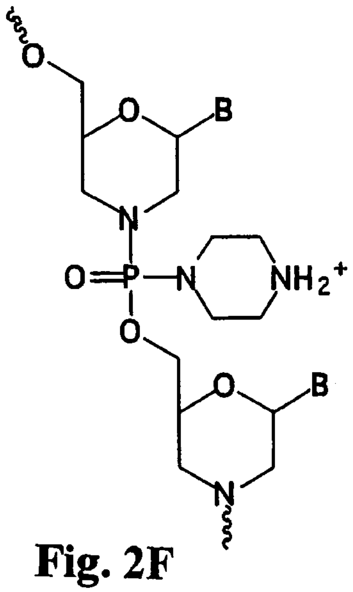

The linkages shown in FIGS. 2C and 2D are designed for 7-atom unit-length backbones. In Structure 3C, the X moiety is as in Structure 3B, and the moiety Y may be methylene, sulfur, or, preferably, oxygen. In Structure 2D, the X and Y moieties are as in Structure 2B. Particularly preferred morpholino oligonucleotides include those composed of morpholino subunit structures of the form shown in FIG. 2B, where X═$NH_2$ or $N(CH_3)_2$, Y═O, and Z═O.

As noted above, the substantially uncharged oligomer may advantageously include a limited number of charged backbone linkages. One example of a cationic charged phophordiamidate linkage is shown in FIG. 2F. This linkage, in which the dimethylamino group shown in FIG. 2E is replaced by a 1-piperazino group as shown in FIG. 2F, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

The antisense compounds can be prepared by stepwise solid-phase synthesis, employing methods detailed in the references cited above. In some cases, it may be desirable to add additional chemical moieties to the antisense compound, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

V. Inhibition of Viral Replication

The antisense compounds detailed above are useful in inhibiting replication of ssRNA viruses of the Flaviviridae, Picornaviridae, Caliciviridae, Togaviridae, Arteriviridae, Coronaviridae, Astroviridae and Hepeviridae virus families. In one embodiment, such inhibition is effective in treating infection of a host animal by these viruses. Accordingly, the method comprises, in one embodiment, contacting a cell infected with the virus with an antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific virus causing the infection can be determined by methods known in the art, e.g., serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting broad families and/or genera of viruses, e.g., Picornaviridae, Caliciviridae, Togaviridae and Flaviviridae. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e., one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of an antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., ANTISENSE OLIGONUCLEOTIDES: A NEW THERAPEUTIC PRINCIPLE, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.

Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g., in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc., and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g., by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed.) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml or less.

The sample may be treated to remove unwanted components and/or to treat the heteroduplex species in the sample to remove unwanted ssRNA overhang regions, e.g., by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

VI. Heteroduplex Complex

In another aspect, the invention includes a heteroduplex complex formed between:

(a) a region within the 5'-terminal 40 bases of the positive strand RNA of an RNA virus having a single-stranded, positive-sense RNA genome and selected from one of the Flaviviridae, Picornaviridae, Caliciviridae, Togaviridae, Arteriviridae, Coronaviridae, Astroviridae or Hepeviridae families, which region is capable of forming internal stem-loop secondary structure, and (b) an oligonucleotide analog compound characterized by:

(i) a nuclease-resistant backbone, (ii) capable of uptake by mammalian host cells, (iii) containing between 12-40 nucleotide bases, (iv) having a targeting sequence of at least 12 subunits that is complementary to a region associated with such stem-loop secondary structure within the 5'-terminal end 40 bases of the positive-sense RNA strand of the virus, where said heteroduplex complex has a $T_m$ of dissociation of at least 45° C. and disruption of such stem-loop secondary structure.

An exemplary compound is composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

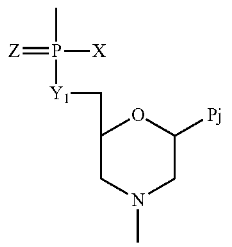

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X=$NR_2$, where each R is independently hydrogen or methyl. The compound may be the oligonucleotide analog alone or a conjugate of the analog and an arginine-rich polypeptide capable of enhancing the uptake of the compound into host cells.

In one embodiment, the compound is effective, when administered to the host cells, to form a heteroduplex structure (i) composed of the positive sense strand of the virus and the oligonucleotide compound, and (ii) characterized by a $T_m$ of dissociation of at least 45° C. and disruption of such stem-loop secondary structure.

EXAMPLES

The following examples illustrate but are not intended in any way to limit the invention.

Materials and Methods

Standard recombinant DNA techniques were employed in all constructions, as described in Ausubel, F M et al., in Current Protocols In Molecular Biology, John Wiley and Sons, Inc., Media, Pa., 1992 and Sambrook, J. et al., in Molecular Cloning: A Laboratory Manual, Cold Spring Harbor Laboratory Press, Cold Spring Harbor, N.Y., Vol. 2, 1989).

All peptides were custom synthesized by Global Peptide Services (Ft. Collins, Colo.) or at AVI BioPharma (Corvallis, Oreg.) and purified to >90% purity (see Example 2 below). PMOs were synthesized at AVI BioPharma in accordance with known methods, as described, for example, in (Summerton and Weller 1997) and U.S. Pat. No. 5,185,444.

PMO oligomers were conjugated at the 5' end with an arginine-rich peptide ($R_9F_2C$-5'-PMO) to enhance cellular uptake as described (U.S. Patent Application 60/466,703 and (Moulton, Nelson et al. 2004).

Figure 9:
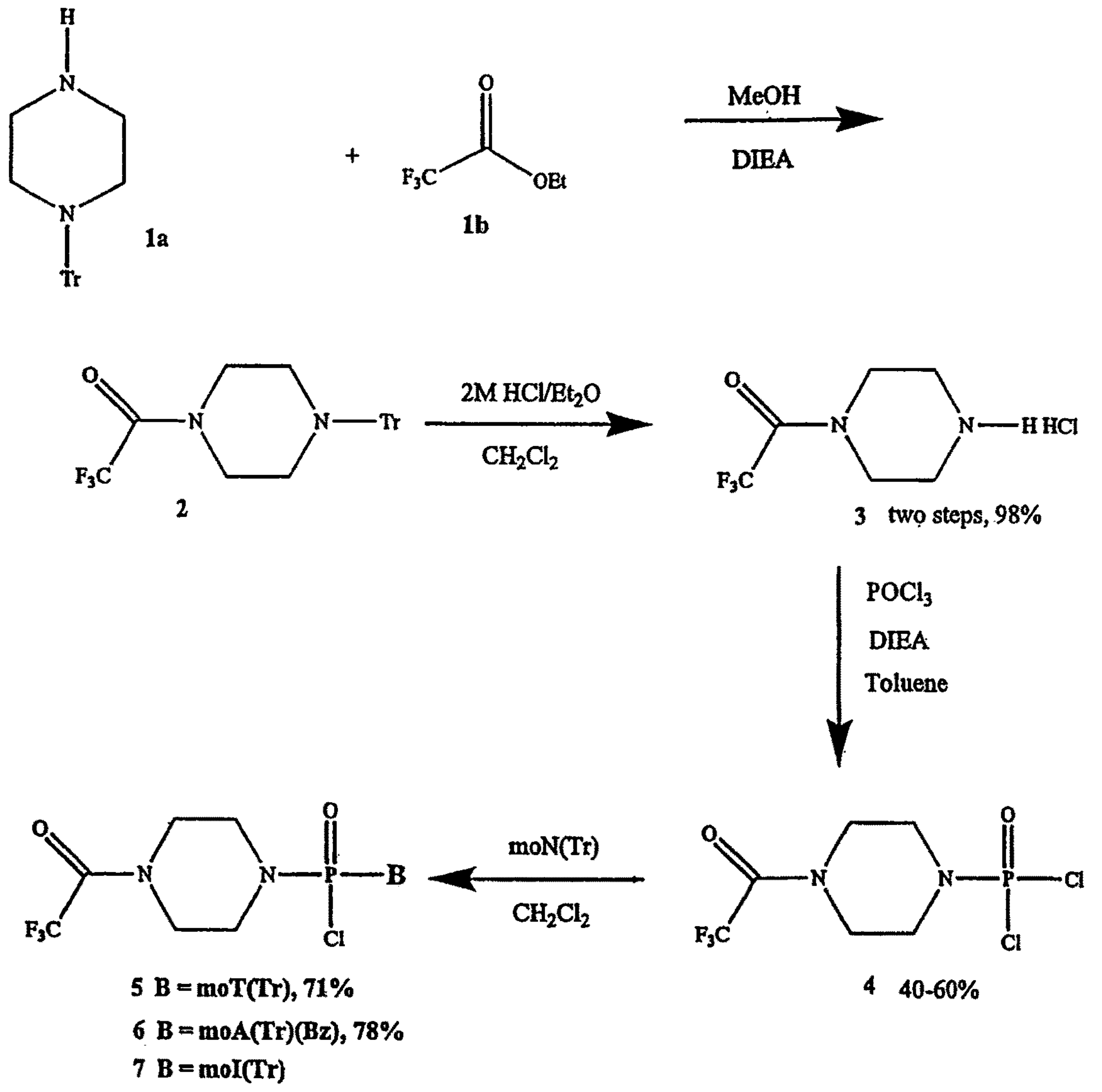
FIG. 9 shows the synthetic steps to produce subunits used to produce +PMO containing the (1-piperazino)phosphinylideneoxy cationic linkage as shown in FIG. 2F.

A schematic of a synthetic pathway that can be used to make morpholino subunits containing a (1 piperazino)phosphinylideneoxy linkage is shown in FIG. 9; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino)phosphinylideneoxy linkage can be incorporated into the existing PMO synthesis protocol, as described, for example in Summerton and Weller (1997), without modification.

Example 1

Antisense Inhibition of Flaviviridae (Yellow Fever Virus) In Vitro

Although an effective vaccine for yellow fever virus (YFV) has been available for many years, this virus continues to be a leading cause of hemorrhagic fever with mortality rates as high as 50%. Worldwide, there are 200,000 estimated cases of yellow fever (with 30,000 deaths) annually. Small numbers of imported cases also occur in countries free of yellow fever (WHO, Fact Sheet 100, 2001).

A PMO antisense oligomer targeted to the 5' positive strand terminus of YFV (SEQ ID NO:49) was evaluated in a 4-concentration test. The standard CPE test used an 18 h monolayer (80-100% confluent) of Vero cells, medium was drained and each of the concentrations of PMO or scramble control sequence was added, followed within 15 min by virus or virus diluent. Two wells are used for each concentration of compound for both antiviral and cytotoxicity testing. The plate was sealed and incubated the standard time period required to induce near-maximal viral CPE. The plate was then stained with neutral red by the method described below and the percentage of uptake indicating viable cells read on a microplate autoreader at dual wavelengths of 405 and 540 nm, with the difference taken to eliminate background. An approximated virus-inhibitory concentration, 50% endpoint (EC50) and cell-inhibitory concentration, 50% endpoint (IC50) was determined from which a general selectivity index (S.I.) was calculated: S.I.=(IC50)/(EC50). An SI of 3 or greater indicates significant antiviral activity. The PMO targeting the 5' positive-strand terminal region (SEQ ID NO:49) produced an SI of 21 in this assay.

Example 2

Antisense Inhibition of Flaviviridae (Dengue Virus Serotypes 1-4) In Vitro

Dengue Fever/Dengue Hemorrhagic Fever (DF/DHF) has become a major global health problem over the past 20 years. Geographic distribution of the dengue virus (DEN), its mosquito vectors and the disease burden it causes continue to increase. The World Health Organization estimates that there are 50-100 million new infections yearly. DF/DHF is now a leading cause of hospitalization and death among children in southern Asia, and its incidence is sharply rising in the Americas. There is currently no vaccine or effective therapeutic. One requirement of a successful vaccine or therapeutic is that it be effective against all 4 human serotypes of DEN. The purpose of this study was to evaluate the efficacy and specificity of PMO that target the 5' positive-strand terminal stem loop at inhibiting the replication of four serotypes of DEN in Vero cells in culture. The PMO was designed to target the sequence element in the positive-strand DEN2 RNA that may be important in viral transcription and/or translation (Markoff 2003). The PMO in this study were conjugated to an arginine-rich peptide in order to facilitate entry into Vero E6 cells (Moulton, Nelson et al. 2004; Neuman, Stein et al. 2004).

Figure 5A:
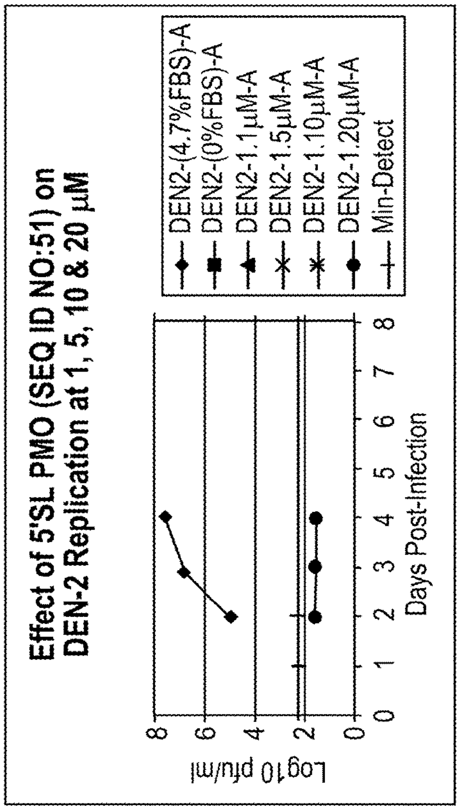
FIGS. 5A-5D show the inhibition of Dengue virus replication in infected Vero cells in the presence of an antisense oligomer that targets the 5' positive-strand terminal region of Dengue virus types 1-4.
Figure 5B:
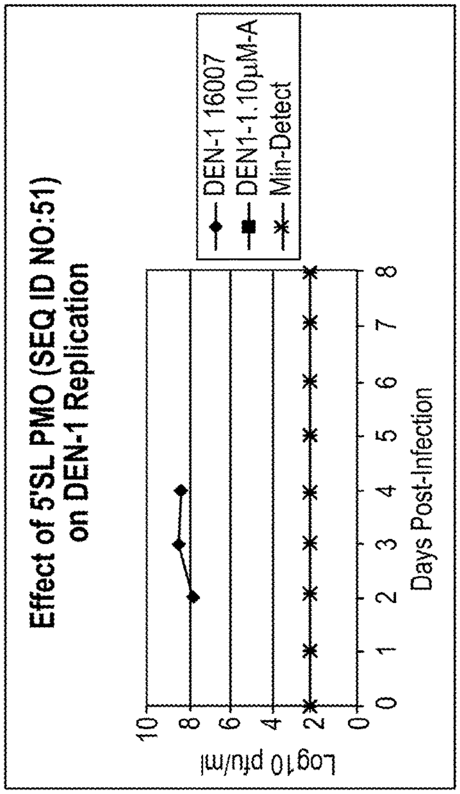
Figure 5C:
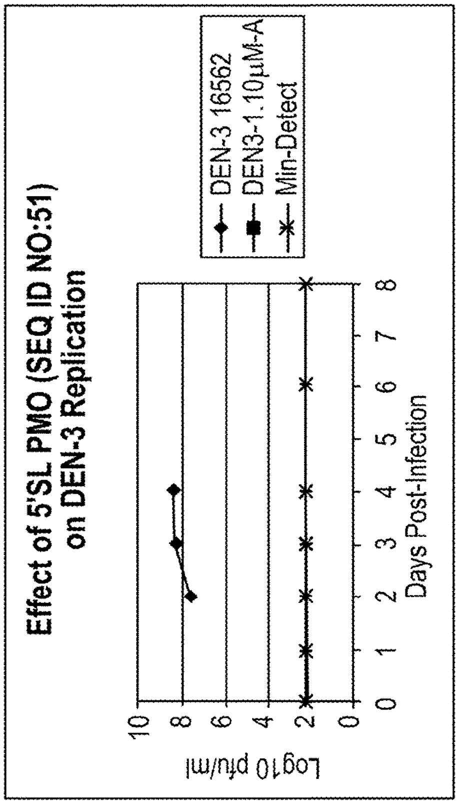
Figure 5D:
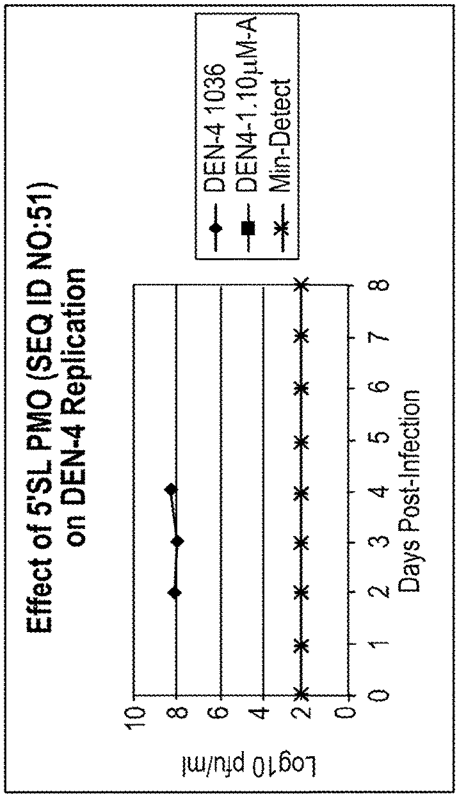

A PMO, 5'SL, (SEQ ID NO:51) designed to hybridize to the 5' positive strand terminal region of Dengue 2 virus (DEN2), were evaluated for their ability to inhibit Dengue virus replication in mammalian cell culture. The PMOs were conjugated to a short arginine-rich peptide ($R_9F_2C$-5'-PMO) to facilitate their entry into cells in culture. Vero E6 cells were incubated with the PMO agents, inoculated with DEN serotypes 1-4 (DEN1, DEN2, DEN3, DEN4, respectively), and viral titer determined by plaque-assay 5-8 days later. The compound targeting the 5' positive strand terminus (5'SL) reduced the titer of DEN2 by over 4 orders of magnitude, compared to controls, in a dose-dependent and sequence-specific manner over a 4 day period as shown in FIG. 5A. Ten μM solutions of the 5'SL PMO reduced the titer of all four Dengue serotypes by over two to four orders of magnitude, in some cases below detectable limits as shown in FIGS. 5A-5B. The 5'SL PMO was less effective against DEN4 (two log reduction) than it was against DEN1, DEN2 and DEN3 (four log reductions) due to a two base pair mismatch between the 5'SL PMO and its target sequence in DEN4. The effective anti-DEN compounds did not alter the titer of West Nile Virus (WNV) grown in Vero E6 cells. This data indicates that the 5'SL PMO compound is a potential DEN 1-4 therapeutic.

Example 3

Antisense Inhibition of Coronaviridae (Porcine Reproductive and Respiratory Syndrome Virus, PRRSV) In Vitro Porcine reproductive and respiratory syndrome (PRRS) is a contagious viral disease that is characterized by reproductive failure in sows and respiratory disease in young pigs. The causative agent, PRRSV, is a single-stranded RNA virus with genome organization similar to that of other members of the Coronaviridae. PRRS causes heavy economic losses to the swine industry though a vaccine has been widely used for years. Specific anti-PRRSV drugs are urgently needed as one of the integrated strategies to prevent and control PRRSV infection. A PMO (PRRSV-la, SEQ ID NO:109) that targets the 5' positive strand terminal region of PRRSV was tested for its ability to inhibit viral replication as described below.

The first test was designed to determine whether the PRRSV-la PMO could inhibit the development of virus-induced, cell pathogenic effect (CPE). ATCC CRL11171 cells were used for this experiment as previously reported. The CRL11171 monolayer cells were treated with the PRRSV-la PMO (SEQ ID NO:109) in DMEM for 4 h at 37° C. The PMOs were removed from the cells and inoculated with PRRSV strain VR2385 at a multiplicity of infection (MOI) of one. The cells were cultured and observed daily for CPE development. A blank control and the control PMO (DSscr, a scramble sequence PMO) were included as negative controls. The cell culture medium was also collected and titrated in CRL11171 cells to determine PRRSV titer.

Figure 6:
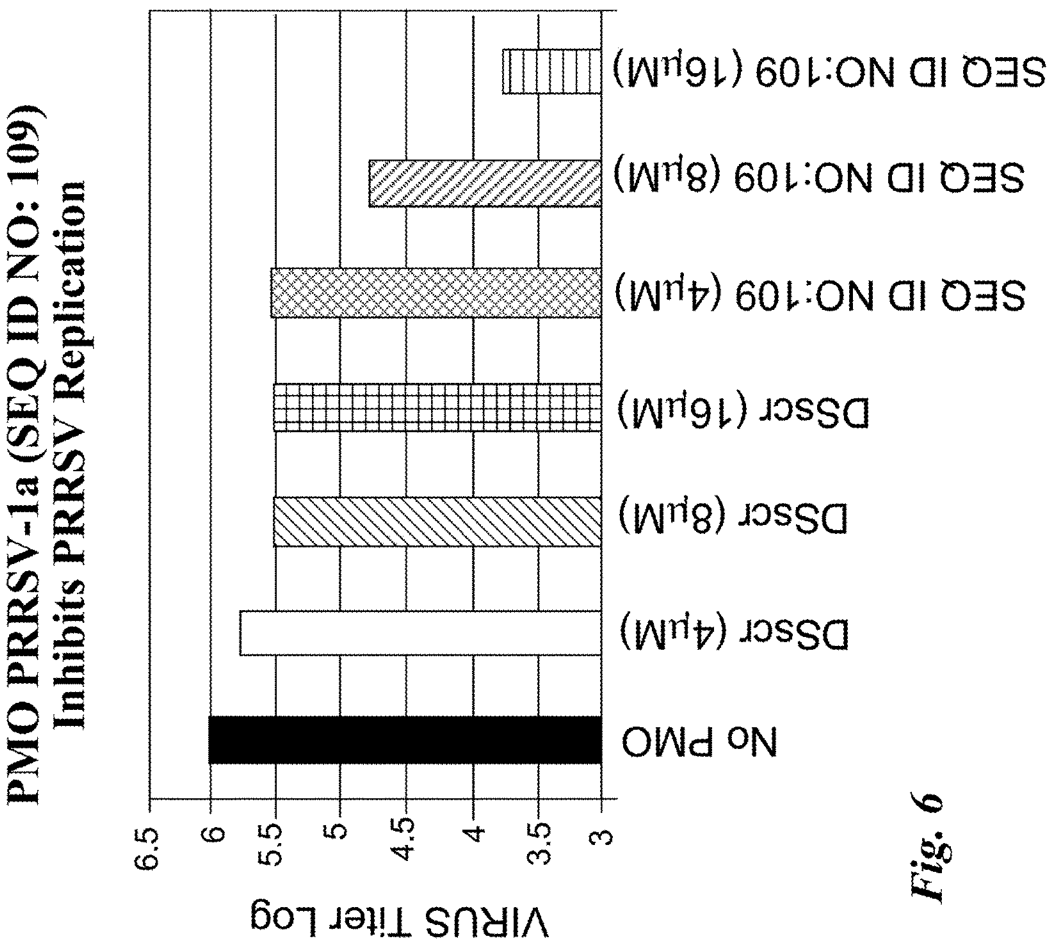
FIG. 6 shows that PMO can reduce PRRSV replication as measured by viral titer.
Figure 7:
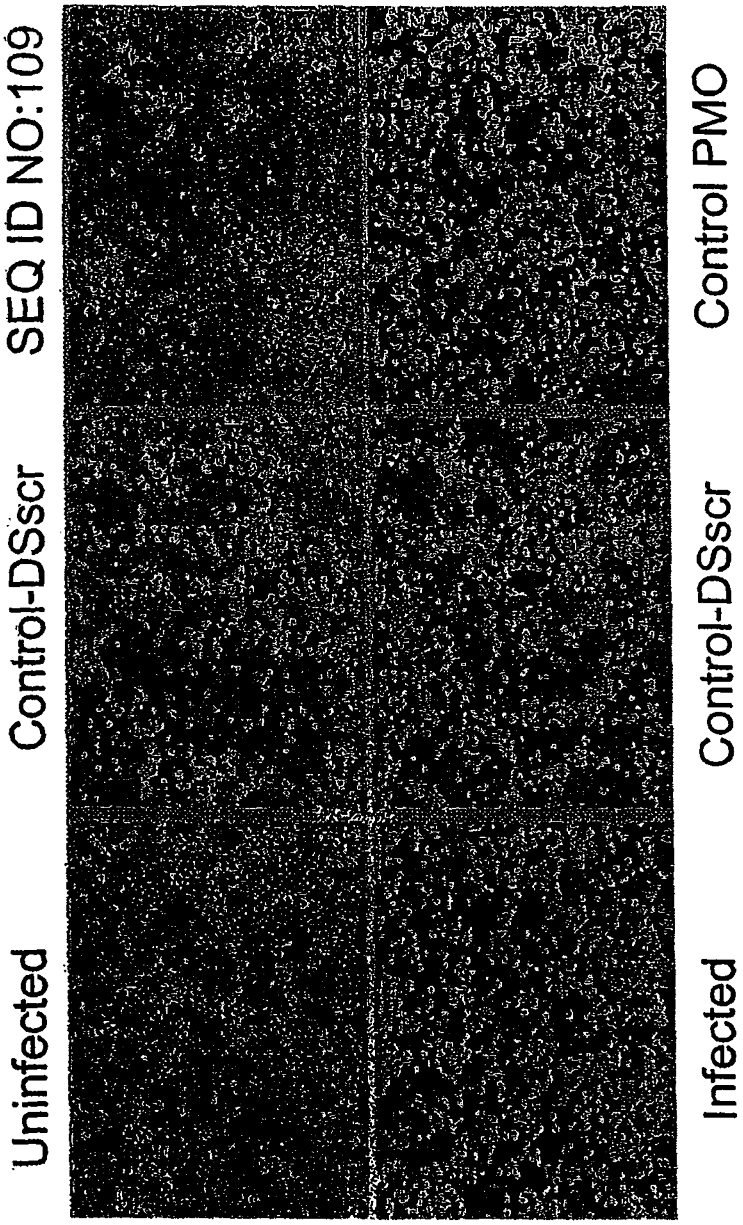
FIG. 7 shows in vitro PMO treatment of CRL11171 cells inoculated with PRRSV have reduced cell pathogenic effects.

The PRRSV-la PMO targeting the 5' positive-strand end-terminus of the untranslated region (UTR), was found to be effective in inhibiting PRRSV replication (FIG. 6). The cells treated with PRRSV-la PMO at 16 μM had much less cell pathogenic effect (CPE) development than controls (FIG. 7). CPE is clearly visible after PRRSV infection (positive), while uninfected control cells remain an intact monolayer (blank). PMO PRRSV-la reduced CPE development, while other PMOs including control PMO did not have much effect in blocking CPE. The cells and medium were harvested for titration of PRRSV yield. Tissue culture infectious dose (TCID50) was calculated based on CPE development of different dilutions. PRRSV-la reduced virus yield by more than 90% (not shown).

The inhibition of PRRSV replication by the PRRSV-la PMO was also shown to be dose-dependent. Using the PMO-treatment and virus culture conditions described above, three different concentrations of PRRSV-la and DSscr control PMO (4, 8 and 16 mM) were tested on PRRSV-infected CRRL11171 cells for the ability to inhibit viral replication as measured by viral titer. As shown in FIG. 6, the PRRSV-la PMO inhibits PRRSV replication in a dose-dependent manner.

Example 4

Antisense Inhibition of Tick Borne Encephalitis Virus

This example describes a study that was devised to test the antiviral activity of antisense PMO compounds of the present invention against two flaviviruses; Tick Borne Encephalitis virus (TBE) and West Nile virus (WNV). Two PMO oligomers were evaluated for antiviral activity; TBE 5'SL, SEQ ID NO:57 and; a scramble control sequence DSscr (5'-AGTCTCGACTTGCTACCTCA-3' SEQ ID NO:133). Both PMO oligomers were conjugated at the 5' end with an arginine-rich peptide ($R_9F_2C$-5'-PMO) (SEQ ID NO: 121) to enhance cellular uptake as described (U.S. Patent Application 60/466,703 and (Moulton, Nelson et al. 2004). The WNV infection provided a negative control infection as there is no homology between WNV and the TBE 5'SL targeting PMO. This control indicates the level of non-specific viral suppression of each of the PMOs. The PMO compounds were prepared to provide a 2 mM stock solution, which were then titrated against a standard dose of virus on tissue culture cells. Cells were infected with a multiplicity of infection (MOI) of 1 and the virus yield was assessed in samples of supernatant medium taken at 18 hours post infection.

The two virus strains used in this example:

1) TC 401 West Nile 99-34940-31A (New York strain) Passage 2
2) TC 339 Tick Borne Encephalitis virus (Hypr strain) Passage 49

Four T175 tissue culture flasks (NUNC) of SW 13 cells (human caucasian adrenal cortex adenocarcinoma cell line ECAAC 87031801 grown in RPMI 1640 medium plus 5% FBS) at passage 130 were washed twice with trypsin-EDTA (1×) and incubated for 2-3 minutes at 37° C. The cells were resuspended in 11.5 ml growth medium per flask and pooled.

A cell count was performed on the pooled cell suspension and the result was $1.74\times10^6$ cells/ml with 99% viability. Six mls of the cell suspension was used to seed four T175 flasks and 40 ml of the cell suspension was diluted to 270 ml. This was dispensed in 3 ml aliquots per well in 15 six-well plates. The plates were incubated overnight to form confluent cell monolayers.

Each of the PMO compounds was diluted to 25, 20, 15, 10 and 5 μM in 4 ml serum-free RPMI 1640 medium. The medium was removed from the wells of two six-well plates. 2 ml of the appropriate compound dilution was dispensed in all wells of a plate and this was repeated on separate plates for both PMO compounds. The plates were incubated at 37° C. for 5 hours. The two viruses were removed from the −70° C. freezer and thawed rapidly. Each virus was diluted to $2\times10^6$ pfu/ml to produce 42 ml serum-free medium. The six-well plates were removed from the incubator and the pre-treatment medium aspirated from all the wells. 1 ml of medium was added to each well of the control plate (no compound). Each set of plates received 1 ml/well of either TBE or WN diluted to $2\times10^6$ pfu/ml. The plates were incubated at room temperature for 1 hour and the medium was then removed and replaced with 2 ml RPMI 1640 plus 1% FBS plus the same concentration of test compound as used to pre-treat the cells. The plates were incubated at 37° C. for 18 hours.

To prepare 24 well plates for determining virus titers, eight T175 tissue culture flasks (NUNC) of SW 13 cells at passage 131 were washed twice with trypsin-EDTA (1×) and incubated for 2-3 minutes at 37° C. The cells were resuspended in 11.5 ml growth medium per flask and pooled. A cell count was performed on the pooled cell suspension and the result was $1.7\times10^6$ cells/ml with 99% viability. 80 ml of the cell suspension was diluted to 680 ml. These cells were dispensed as 1 ml per well aliquots in eight 24-well plates. The plates were incubated overnight to form confluent monolayers.

At 18 hours post-infection the supernatant media from the PMO-treated, virus-infected six-well plates were harvested from each individual wells. Thirty microliters of each harvest was placed in a single cup of a 96-well plate with 270 microliters serum-free medium. The remainder of the sample was placed in cryotube and stored at −70° C. The medium was removed from the 24-well plates and 250 μl of the titration dilutions were transferred from the 96-well plates to the 24 well plates which were incubated at 37° C. for one hour. One ml agarose overlay medium was added to each well and after allowing the agarose to set at room temperature the plates were incubated at 37° C. for 5 days. After 5 days the plates were removed from the incubator, 1 ml 10% Formol saline was added to each well and the plates were left at room temperature for 3 hours. The plates were washed under running water to remove the agarose medium and left to drain inverted while the remaining plates were washed. Each well then received 1 ml of 0.1% Naphthalene black stain and the plates were left for 30 minutes before the stain was removed and the plates washed under running water. They were then left to dry (inverted) for 3 hours. Viral plaques were counted to determine the titer.

Figure 8:
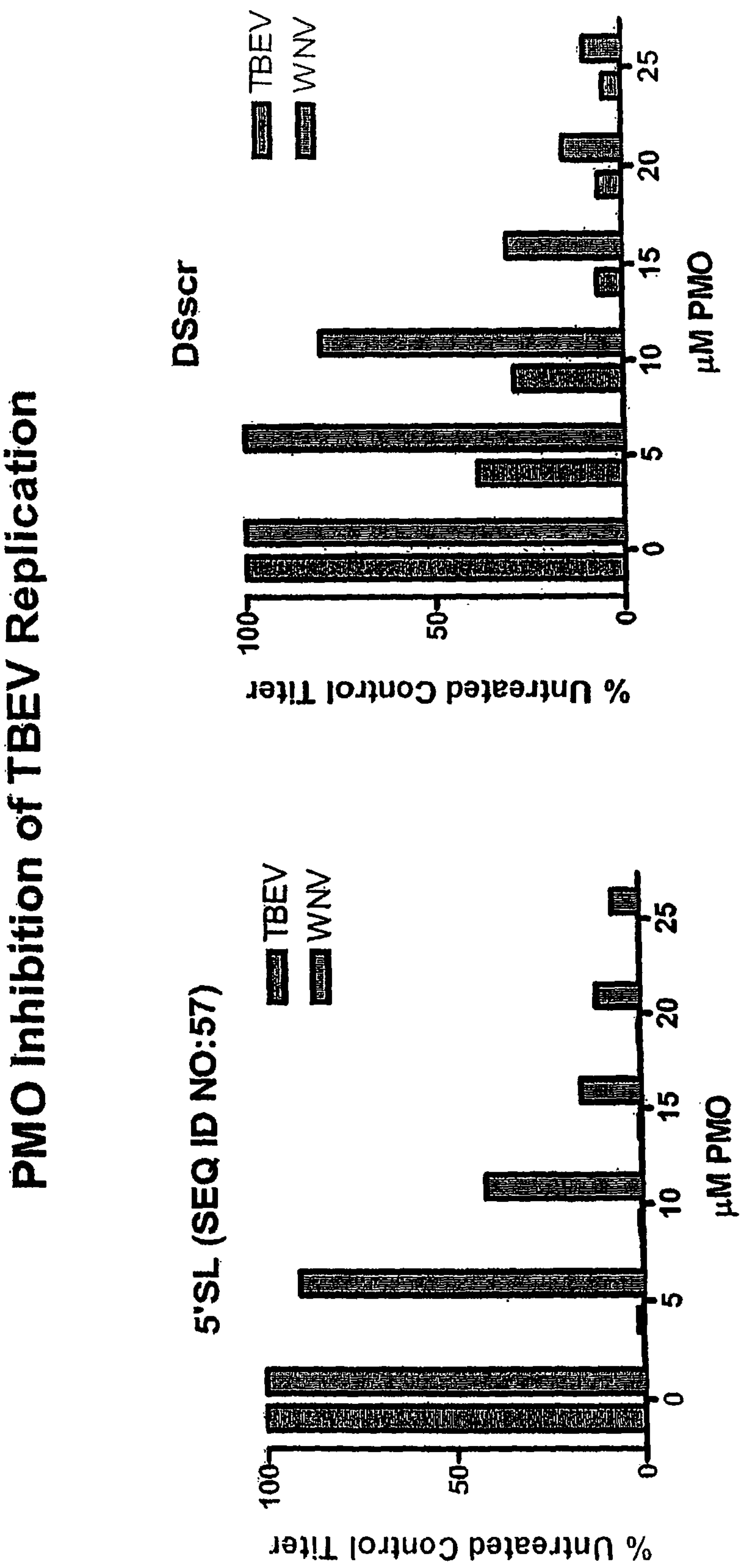
FIG. 8 shows the reduction of TBEV replication in vitro in the presence of PMO targeting the 5' terminal region of TBEV.

FIG. 8 shows the viral titer obtained from the PMO-treated infections as a percentage of untreated control, with virus-infected cells infected with either TBEV or WNV and treated with either the TBEV antisense compound where the PMO compound is either 5'SL (SEQ ID NO:57) or control PMO (DSscr, a scrambled base sequence). As seen from a comparison of the viral titers in FIG. 8, significant there is a reduction in viral titre in all cells (treated and control) with increasing concentrations of compound, thought to be due to a cell-toxicity effect of the attached arginine-rich peptide present in both antisense and control compounds. However, at compound concentrations of 5 μM and above, there is seen a sequence-specific increase in TBEV inhibition, both relative to WNV (FIG. 8), and relative to the DSscr scrambled control sequence.

Example 5

Effect of PMO on West Nile Virus (WNV) Infection in Mice

PMOs are uncharged, water-soluble, nuclease-resistant antisense agents that are typically synthesized to a length of about 20 subunits and contain purine and pyrimidine bases attached to a backbone composed of morpholine rings joined by phosphorodiamidate intersubunit linkages. In experiments in support of the invention, it was shown that conjugation of an Arg-rich peptide (designated as P007; SEQ 1D NO:122) to the 5'-end of the PMOs greatly facilitates the delivery of the PMO into cultured cells. P007-PMOs targeting different regions of the viral genome have inhibited WNV virus infection to various degrees. Among them, PMOs targeting the 5'-terminal 20 nucleotides (5' End; SEQ ID NO:47) showed potent antiviral activity.

Experiments were conducted in mice to extend the observations to in vivo conditions. Female BALB/c mice were used. The mice were obtained from Simonsen Laboratories (Gilroy, Calif.). At the time that the experiment was started, the animals had been in the animal facility for one week and they were greater than 6 weeks of age. The mice weighed 12.3 to 19.8 g with an average of 16.1 g. Experiments were conducted in the BSL-3 animal suite at Utah State University Laboratory Animal Research Center (LARC). Two PMO compounds were used: 1) a PMO targeting the 5' terminus (NG040006; SEQ ID NO:47) and; 2) the same PMO conjugated at its 5' end with the P007 arginine-rich peptide (SEQ ID NO:122) and named NG040005. NG040007 is an unconjugated, scramble control PMO. AMPLIGEN™ was used as a positive control, antiviral compound and was obtained from William M. Mitchell (School of Medical Pathology, Vanderbilt University, Nashville, Tenn. 37240). Since ampligen is an RNA-like molecule, care was used to prevent contamination with RNase by using RNase-free materials and DEPC-treated water.

Ten animals were randomly assigned to each treatment group, except for the placebo group 11, which had 20 animals. Intraperitoneal treatments were initiated 24 hours before subcutaneous WNV challenge. PMO treatments continued qd, −4 hours before viral challenge, 1, 2, 3, 4, 5 and 5 days post-viral injection (dpi). Ampligen was treated i.p., qd, −1, 1, 3, and 5 dpi. Dosages and treatment groups are indicated in the table below along with Survival and mean day to death (MDD). NG040005 and ampligen increased the MDD of WNV-infected mice as compared to the placebo control (Table 4).

TABLE 4

| Effect of PMOs on West Nile virus infection in mice |
|---|
| Animals: Female BALB/c mice, >6 wk old<br>Virus: West Nile virus, NY crow brain homogenate, $10^{6.3}$ infectious units, s.c. injection<br>Drug diluent: saline<br>Treatment schedule: qd, −1 d, −4 h, 1, 2, 3, 4, 5, 6 d |

TABLE 4-continued

Effect of PMOs on West Nile virus infection in mice

Treatment Route: i.p.
Duration of experiment: 21 days

| Drug | Dose | Schedule | % survival (alive/ total) | MDD[a] ± SD | Survival analysis[b] |
|---|---|---|---|---|---|
| NG040005 | 250 µg/inj | qd, −1 d, −4 h, 1, 2, 3, 4, 5, 6 d | 50% (5/10) | 14.0 ± 3.8*** | P = 0.20 |
| NG040006 | 750 µg/inj | qd, −1 d, −4 h, 1, 2, 3, 4, 5, 6 d | 40% (4/10) | 8.2 ± 1.0 | P = 0.95 |
| ampligen | 14 mg/kg | qd, −1 d, 1, 3, 5 d | 80% (8/10) | 13.5f ± 4.9 | P > 0.01** |
| placebo | — | qd, −1 d, −4 h, 1, 2, 3, 4, 5, 6 d | 35% (7/20) | 8.6 ± 1.3 | — |

[a]Mean day to death of mice dying prior to day 21. Student's t-test was used for analysis.

[b]Log-rank survival analysis.

Toxicity controls were not run in this first experiment because of limited amounts of compounds.

*P ≤ 0.05,

**P ≤ 0.01,

***P ≤ 0.001 compared to placebo.

TABLE 5

Sequence Listing Table

| SEQ ID NO | Sequence, 5' to 3' |
|---|---|
| 1 | GNNGATGTTCGCGTCGGTGAGCGGAGAGGAAACAGATTTC |
| 2 | AGAAGTTTATCTGTGTGAACTTCTTGGCTTAGTATCGTTG |
| 3 | AGACGTTCATCTGCGTGAGCTTCCGATCTCAGTATTGTTT |
| 4 | AGTAGTTCGCCTGTGTGAGCTGACAAACTTAGTAGTGTTT |
| 5 | AGTAAATCCTGTGTGCTAATTGAGGTGCATTGGTCTGCAA |
| 6 | AGTTGTTAGTCTACGTGGACCGACAAAGACAGATTCTTTG |
| 7 | GCCAGCCCCCTGATGGGGGCGACACTCCACCATGAATCAC |
| 8 | AGATTTTCTTGCACGTGCATGCGTTTGCTTCGGACAGCAT |
| 9 | AGATTTTCTTGCACGTGCGTGCGCTTGCTTCAGACAGCAA |
| 10 | AGATTTTCTTGCACGTGTGTGCGGGTGCTTTAGTCAGTGT |
| 11 | TTAAAACAGCTCTGGGGTTGTACCCACCCCAGAGGCCCAC |
| 12 | TTAAAACAGCCTGTGGGTTGTACCCACCCACAGGGCCCAC |
| 13 | TTAAAACAGCCTGTGGGTTGTTCCCACCCACAGGCCCATT |
| 14 | TTAAAACAGCTCTGGGGTTGCTCCCACCCCAGAGGCCCAC |
| 15 | TTAAAACAGCTCTGGGGTTGTTCCCACCCCAGAGGCCCAC |
| 16 | GAGTGTTCCCACCCAACAGGCCCACTGGGTGTTGTACTCT |
| 17 | TTAAAACAGCCTGGGGGTTGTACCCACCCCTGGGGCCCAC |
| 18 | TTAAAACTGGGAGTGGGTTGTTCCCACTCACTCCACCCAT |
| 19 | TTAAAACAGCGGATGGGTATCCCACCATTCGACCCATTGG |
| 20 | TTGAAAGGGGGCGCTAGGGTTTCACCCCTAGCATGCCAAC |
| 21 | TTCAAGAGGGGTCTCCGGGAATTTCCGGAGTCCCTCTTGG |

TABLE 5-continued

Sequence Listing Table

| | |
|---|---|
| 22 | GTAAAAGAAATTTGAGACAATGTCTCAAACTCTGAGCTTC |
| 23 | GTTAATGAGAAATGGCTTCTGCCATCGCTCTCTCGAGCTC |
| 24 | GTGATCGTGATGGCTAATTGCCGTCCGTTGCCTATTGGGC |
| 25 | GTGATTTAATTATAGAGAGATAGTGACTTTCACTTTTCTT |
| 26 | GTGAATGATGATGGCGTCAAAAGACGTCGTTCCTACTGCT |
| 27 | GCCATGGAGGCCCATCAGTTTATTAAGGCTCCTGGCATCA |
| 28 | ATGGAAGCTATCGGACCTCGCTTAGGACTCCCATTCCCAT |
| 29 | ATATTAGGTTTTTACCTACCCAGGAAAAGCCAACCAACCT |
| 30 | ACTTAAAAAGATTTTCTATCTACGGATAGTTAGCTCTTTT |
| 31 | ACTTTTAAAGTAAAGTGAGTGTAGCGTGGCTATATCTCTT |
| 32 | GATTGCGAGCGATTTGCGTGCGTGCATCCCGCTTCACTGA |
| 33 | ACTTAAGTACCTTATCTATCTACAGATAGAAAAGTTGCTT |
| 34 | TATAAGAGTGATTGGCGTCCGTACGTACCCTCTCAACTCT |
| 35 | ATGACGTATAGGTGTTGGCTCTATGCCTTGGCATTTGTAT |
| 36 | GCTCGAAGTGTGTATGGTGCCATATACGGCTCACCACCAT |
| 37 | CCAAGAGGGGGGTGGTGATTGGCCTTTGGCTTATCAGTGT |
| 38 | ATAGGGTACGGTGTAGAGGCAACCACCCTATTTCCACCTA |
| 39 | ACCCTACAAACTAATCGATCCAATATGGAAAGAATTCACG |
| 40 | ATGGGCGGCGCAAGAGAGAAGCCCAAACCAATTACCTACC |
| 41 | ACCGACGCGAACATCNNC |
| 42 | TCCTCTCCGCTCACCGACGC |
| 43 | TCACACAGATAAACTTCT |
| 44 | AAGCCAAGAAGTTCACACAG |
| 45 | TCACGCAGATGAACGTCT |
| 46 | GAGATCGGAAGCTCACGCAG |
| 47 | GCTCACACAGGCGAACTACT |
| 48 | TAAGTTTGTCAGCTCACACAG |
| 49 | CAATTAGCACACAGGATTTACT |
| 50 | TTGCAGACCAATGCACCTCA |
| 51 | GTCCACGTAGACTAACAACT |
| 52 | GTCTTTGTCGGTCCACGTAG |
| 53 | CCCATCAGGGGGCTGGC |
| 54 | TGGAGTGTCGCCCCCATCAG |
| 55 | ATGCACGTGCAAGAAAATCT |
| 56 | ATGCTGTCCGAAGCAAACGC |
| 57 | CACGCACGTGCAAGAAAATCT |
| 58 | TGAAGCAAGCGCACGCACGT |
| 59 | ACACACGTGCAAGAAAATCT |
| 60 | ACACTGACTAAAGCACCCGC |

TABLE 5-continued

| Sequence Listing Table | |
|---|---|
| 61 | GGTACAACCCCAGAGCTGTTTTAA |
| 62 | GTGGGCCTCTGGGGTGGGTA |
| 63 | CAACCCACAGGCTGTTTTAA |
| 64 | GTGGGCCCTGTGGGTGGGTA |
| 65 | CAACCCACAGGCTGTTTTAA |
| 66 | AATGGGCCTGTGGGTGGGAA |
| 67 | CAACCCCAGAGCTGTTTTAA |
| 68 | GTGGGCCTCTGGGGTGGGAG |
| 69 | CAACCCCAGAGCTGTTTTAA |
| 70 | GTGGGCCTCTGGGGTGGGAA |
| 71 | CCTGTTGGGTGGGAACACTC |
| 72 | AGAGTACAACACCCAGTGGG |
| 73 | CAACCCCCAGGCTGTTTTAA |
| 74 | GTGGGCCCCAGGGGTGGGTA |
| 75 | CAACCCACTCCCAGTTTTAA |
| 76 | ATGGGTGGAGTGAGTGGGAA |
| 77 | ATACCCATCCGCTGTTTTAA |
| 78 | CCAATGGGTCGAATGGTGGG |
| 79 | AACCCTAGCGCCCCCTTTCAA |
| 80 | GTTGGCATGCTAGGGGTGAA |
| 81 | TCCCGGAGACCCCTCTTGAA |
| 82 | CCAAGAGGGACTCCGGAAAT |
| 83 | TTGTCTCAAATTTCTTTTAC |
| 84 | GAAGCTCAGAGTTTGAGACA |
| 85 | AGAAGCCATTTCTCATTAAC |
| 86 | GAGCTCGAGAGAGCGATGGC |
| 87 | CAATTAGCCATCACGATCAC |
| 88 | GGCAACGGACGGCAATTAGC |
| 89 | TCTCTCTATAATTAAATCAC |
| 90 | AAAGTCACTATCTCTCTATA |
| 91 | TTGACGCCATCATCATTCAC |
| 92 | AGCAGTAGGAACGACGTCTT |
| 93 | AACTGATGGGCCTCCATGGC |
| 94 | TGATGCCAGGAGCCTTAATA |
| 95 | CGAGGTCCGATAGCTTCCAT |
| 96 | ATGGGAATGGGAGTCCTAAG |
| 97 | GGTAGGTAAAAACCTAATAT |
| 98 | AGGTTGGTTGGCTTTTCCTG |
| 99 | GATAGAAAATCTTTTTAAGT |
| 100 | AAAAGAGCTAACTATCCGTA |
| 101 | ACTCACTTTACTTTAAAAGT |
| 102 | GCCACGCTACACTCACTTTA |
| 103 | CACGCAAATCGCTCGCAATC |
| 104 | TCAGTGAAGCGGGATGCACG |
| 105 | GATAGATAAGGTACTTAAGT |
| 106 | AAGCAACTTTTCTATCTGTA |
| 107 | CGGACGCCAATCACTCTTATA |
| 108 | GAGTTGAGAGGGTACGTACGGA |
| 109 | CATAGAGCCAACACCTATACG |
| 110 | ATACAAATGCCAAGGCATAG |
| 111 | GCACCATACACACTTCGAGC |
| 112 | ATGGTGGTGAGCCGTATATG |
| 113 | AATCACCACCCCCCTCTTGG |
| 114 | GCCAAAGGCCAATCACCACC |
| 115 | GCCTCTACACCGTACCCTAT |
| 116 | TAGGTGGAAATAGGGTGGTT |
| 117 | GATCGATTAGTTTGTAGGGT |
| 118 | CGTGAATTCTTTCCATATTG |
| 119 | TTCTCTCTTGCGCCGCCCAT |
| 120 | GGTAGGTAATTGGTTTGGGC |

| Name | Petide Sequences ($NH_2$ to COOH) | SEQ ID NO |
|---|---|---|
| P003 | RRRRRRRRRFFC | 121 |
| P007 | $(RAhxR)_4Ahx\beta Ala$ | 122 |
| P008 | $(RAhx)_8\beta Ala$ | 123 |
| RX4 | $(RAhx)_4\beta Ala$ | 124 |
| RXR2 | $(RAhxR)_2Ahx\beta Ala$ | 125 |
| RXR3 | $(RAhxR)_3Ahx\beta Ala$ | 126 |

| SEQ ID NO | Sequence, 5' to 3' |
|---|---|
| 127 | ACAGGCGAACTACT |
| 128 | GTCAGCTCACAC |
| 129 | GCTCACACAGGCGA |
| 130 | GCACACAGGATTTACT |
| 131 | GTCCAATGCACCTC |
| 132 | CAATGCACCTCAATTAGC |
| 133 | AGTCTCGACTTGCTACCTCA |

It is claimed:

1. A morpholino subunit of formula:

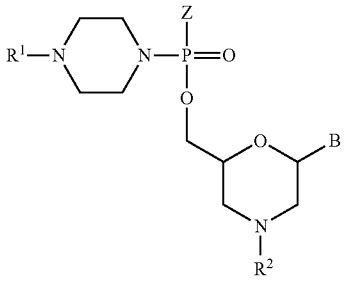

or a salt or isomer thereof, wherein:

B is a base-pairing moiety;

$R^i$ is $C_1$-$C_{12}$ alkylcarbonyl;

$R^2$ is $C_7$-$C_{30}$ aralkyl; and

Z is halo.

2. The morpholino subunit of claim 1, wherein $R^i$ is trifluoroacetyl.

3. The morpholino subunit of claim 1, wherein $R^2$ is trityl.

4. The morpholino subunit of claim 1, wherein $R^2$ is 4-methoxytrityl.

5. The morpholino subunit of claim 1, wherein Z is chloro.

6. The morpholino subunit of claim 1, wherein B is adenine, cytosine, guanine, uracil, thymine, or hypoxanthine.

7. The morpholino subunit of claim 1, wherein B comprises one or more protecting groups.

8. The morpholino subunit of claim 1, wherein B is adenine, cytosine, guanine, uracil, thymine or hypoxanthine, each of which comprise at least one protecting group.

9. The morpholino subunit of claim 1, wherein the morpholino subunit is of formula:

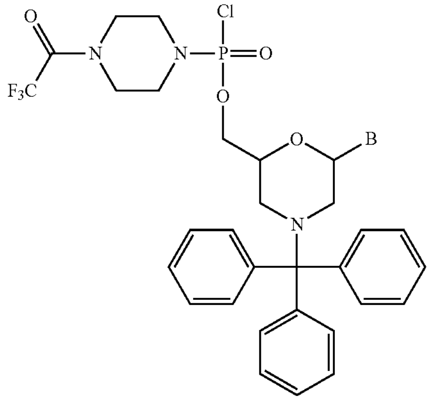

or a salt or isomer thereof, wherein B is a base-pairing moiety.

* * * * *

SEQUENCE LISTING

<160> NUMBER OF SEQ ID NOS: 175

<210> SEQ ID NO 1
<211> LENGTH: 40
<212> TYPE: DNA
<213> ORGANISM: St. Louis encephalitis virus
<220> FEATURE:
<221> NAME/KEY: misc_feature
<222> LOCATION: (2)..(3)
<223> OTHER INFORMATION: n is a, c, g, or t

<400> SEQUENCE: 1
gnngatgttc gcgtcggtga gcggagagga aacagatttc 40

<210> SEQ ID NO 2
<211> LENGTH: 40
<212> TYPE: DNA
<213> ORGANISM: Japanese encephalitis virus

<400> SEQUENCE: 2
agaagtttat ctgtgtgaac ttcttggctt agtatcgttg 40

<210> SEQ ID NO 3
<211> LENGTH: 40
<212> TYPE: DNA
<213> ORGANISM: Murray Valley encephalitis virus

<400> SEQUENCE: 3
agacgttcat ctgcgtgagc ttccgatctc agtattgttt 40

<210> SEQ ID NO 4
<211> LENGTH: 40
<212> TYPE: DNA
<213> ORGANISM: West Nile virus

<400> SEQUENCE: 4
agtagttcgc ctgtgtgagc tgacaaactt agtagtgttt 40

<210> SEQ ID NO 5
<211> LENGTH: 40
<212> TYPE: DNA
<213> ORGANISM: Yellow Fever virus

<400> SEQUENCE: 5
agtaaatcct gtgtgctaat tgaggtgcat tggtctgcaa 40

<210> SEQ ID NO 6
<211> LENGTH: 40
<212> TYPE: DNA
<213> ORGANISM: Dengue Type 2 virus

<400> SEQUENCE: 6
agttgttagt ctacgtggac cgacaaagac agattctttg 40

<210> SEQ ID NO 7
<211> LENGTH: 40
<212> TYPE: DNA
<213> ORGANISM: Hepatitis C virus

<400> SEQUENCE: 7
gccagccccc tgatgggggc gacactccac catgaatcac 40

<210> SEQ ID NO 8
<211> LENGTH: 40

<212> TYPE: DNA
<213> ORGANISM: Tick-borne encephalitis virus

<400> SEQUENCE: 8
agattttctt gcacgtgcat gcgtttgctt cggacagcat 40

<210> SEQ ID NO 9
<211> LENGTH: 40
<212> TYPE: DNA
<213> ORGANISM: Omsk hemorrhagic fever virus

<400> SEQUENCE: 9
agattttctt gcacgtgcgt gcgcttgctt cagacagcaa 40

<210> SEQ ID NO 10
<211> LENGTH: 40
<212> TYPE: DNA
<213> ORGANISM: Powassan virus

<400> SEQUENCE: 10
agattttctt gcacgtgtgt gcgggtgctt tagtcagtgt 40

<210> SEQ ID NO 11
<211> LENGTH: 40
<212> TYPE: DNA
<213> ORGANISM: Poliovirus Mahoney strain

<400> SEQUENCE: 11
ttaaaacagc tctggggttg tacccacccc agaggcccac 40

<210> SEQ ID NO 12
<211> LENGTH: 40
<212> TYPE: DNA
<213> ORGANISM: Human enterovirus A

<400> SEQUENCE: 12
ttaaaacagc ctgtgggttg tacccaccca cagggcccac 40

<210> SEQ ID NO 13
<211> LENGTH: 40
<212> TYPE: DNA
<213> ORGANISM: Human enterovirus B

<400> SEQUENCE: 13
ttaaaacagc ctgtgggttg ttcccaccca caggcccatt 40

<210> SEQ ID NO 14
<211> LENGTH: 40
<212> TYPE: DNA
<213> ORGANISM: Human enterovirus C

<400> SEQUENCE: 14
ttaaaacagc tctggggttg ctcccacccc agaggcccac 40

<210> SEQ ID NO 15
<211> LENGTH: 40
<212> TYPE: DNA
<213> ORGANISM: Human enterovirus D

<400> SEQUENCE: 15
ttaaaacagc tctggggttg ttcccacccc agaggcccac 40

<210> SEQ ID NO 16

```
<211> LENGTH: 40
<212> TYPE: DNA
<213> ORGANISM: Human enterovirus E

<400> SEQUENCE: 16

gagtgttccc acccaacagg cccactgggt gttgtactct                              40

<210> SEQ ID NO 17
<211> LENGTH: 40
<212> TYPE: DNA
<213> ORGANISM: Bovine enterovirus

<400> SEQUENCE: 17

ttaaaacagc ctgggggttg tacccacccc tggggcccac                              40

<210> SEQ ID NO 18
<211> LENGTH: 40
<212> TYPE: DNA
<213> ORGANISM: Human rhinovirus 89

<400> SEQUENCE: 18

ttaaaactgg gagtgggttg ttcccactca ctccacccat                              40

<210> SEQ ID NO 19
<211> LENGTH: 40
<212> TYPE: DNA
<213> ORGANISM: Human rhinovirus B

<400> SEQUENCE: 19

ttaaaacagc ggatgggtat cccaccattc gacccattgg                              40

<210> SEQ ID NO 20
<211> LENGTH: 40
<212> TYPE: DNA
<213> ORGANISM: Foot-and-mouth disease virus

<400> SEQUENCE: 20

ttgaaagggg gcgctagggt ttcaccccta gcatgccaac                              40

<210> SEQ ID NO 21
<211> LENGTH: 40
<212> TYPE: DNA
<213> ORGANISM: Hepatitis A virus

<400> SEQUENCE: 21

ttcaagaggg gtctccggga atttccggag tccctcttgg                              40

<210> SEQ ID NO 22
<211> LENGTH: 40
<212> TYPE: DNA
<213> ORGANISM: Feline calicivirus

<400> SEQUENCE: 22

gtaaaagaaa tttgagacaa tgtctcaaac tctgagcttc                              40

<210> SEQ ID NO 23
<211> LENGTH: 40
<212> TYPE: DNA
<213> ORGANISM: Canine calicivirus

<400> SEQUENCE: 23

gttaatgaga aatggcttct gccatcgctc tctcgagctc                              40
```

-continued

<210> SEQ ID NO 24
<211> LENGTH: 40
<212> TYPE: DNA
<213> ORGANISM: Porcine enteric calicivirus

<400> SEQUENCE: 24
gtgatcgtga tggctaattg ccgtccgttg cctattgggc 40

<210> SEQ ID NO 25
<211> LENGTH: 40
<212> TYPE: DNA
<213> ORGANISM: Calcivirus strain NB

<400> SEQUENCE: 25
gtgatttaat tatagagaga tagtgacttt cacttttctt 40

<210> SEQ ID NO 26
<211> LENGTH: 40
<212> TYPE: DNA
<213> ORGANISM: Norwalk virus

<400> SEQUENCE: 26
gtgaatgatg atggcgtcaa aagacgtcgt tcctactgct 40

<210> SEQ ID NO 27
<211> LENGTH: 40
<212> TYPE: DNA
<213> ORGANISM: Hepatitis E virus

<400> SEQUENCE: 27
gccatggagg cccatcagtt tattaaggct cctggcatca 40

<210> SEQ ID NO 28
<211> LENGTH: 40
<212> TYPE: DNA
<213> ORGANISM: Rubella virus

<400> SEQUENCE: 28
atggaagcta tcggacctcg cttaggactc ccattcccat 40

<210> SEQ ID NO 29
<211> LENGTH: 40
<212> TYPE: DNA
<213> ORGANISM: SARS coronavirus

<400> SEQUENCE: 29
atattaggtt tttacctacc caggaaaagc caaccaacct 40

<210> SEQ ID NO 30
<211> LENGTH: 40
<212> TYPE: DNA
<213> ORGANISM: Porcine epidemic diarrhea virus

<400> SEQUENCE: 30
acttaaaaag attttctatc tacggatagt tagctctttt 40

<210> SEQ ID NO 31
<211> LENGTH: 40
<212> TYPE: DNA
<213> ORGANISM: Transmissible gastroenteritis virus

<400> SEQUENCE: 31
acttttaaag taaagtgagt gtagcgtggc tatatctctt 40

<210> SEQ ID NO 32
<211> LENGTH: 40
<212> TYPE: DNA
<213> ORGANISM: Bovine coronavirus

<400> SEQUENCE: 32
gattgcgagc gatttgcgtg cgtgcatccc gcttcactga 40

<210> SEQ ID NO 33
<211> LENGTH: 40
<212> TYPE: DNA
<213> ORGANISM: Human coronavirus 229E

<400> SEQUENCE: 33
acttaagtac cttatctatc tacagataga aaagttgctt 40

<210> SEQ ID NO 34
<211> LENGTH: 40
<212> TYPE: DNA
<213> ORGANISM: Murine Hepatitis virus

<400> SEQUENCE: 34
tataagagtg attggcgtcc gtacgtaccc tctcaactct 40

<210> SEQ ID NO 35
<211> LENGTH: 40
<212> TYPE: DNA
<213> ORGANISM: Porcine reproductive and respiratory syndrome virus

<400> SEQUENCE: 35
atgacgtata ggtgttggct ctatgccttg gcatttgtat 40

<210> SEQ ID NO 36
<211> LENGTH: 40
<212> TYPE: DNA
<213> ORGANISM: Equine arteritis virus

<400> SEQUENCE: 36
gctcgaagtg tgtatggtgc catatacggc tcaccaccat 40

<210> SEQ ID NO 37
<211> LENGTH: 40
<212> TYPE: DNA
<213> ORGANISM: Human astrovirus

<400> SEQUENCE: 37
ccaagagggg ggtggtgatt ggcctttggc ttatcagtgt 40

<210> SEQ ID NO 38
<211> LENGTH: 40
<212> TYPE: DNA
<213> ORGANISM: Eastern equine encephalitis virus

<400> SEQUENCE: 38
atagggtacg gtgtagaggc aaccacccta tttccaccta 40

<210> SEQ ID NO 39
<211> LENGTH: 40
<212> TYPE: DNA
<213> ORGANISM: Western equine encephalomyelitis virus

<400> SEQUENCE: 39
accctacaaa ctaatcgatc caatatggaa agaattcacg 40

-continued

<210> SEQ ID NO 40
<211> LENGTH: 40
<212> TYPE: DNA
<213> ORGANISM: Venezuelan equine encephalitis virus

<400> SEQUENCE: 40
atgggcggcg caagagagaa gcccaaacca attacctacc 40

<210> SEQ ID NO 41
<211> LENGTH: 18
<212> TYPE: DNA
<213> ORGANISM: Artificial Sequence
<220> FEATURE:
<223> OTHER INFORMATION: Synthetic antisense oligomer
<220> FEATURE:
<221> NAME/KEY: misc_feature
<222> LOCATION: (16)..(17)
<223> OTHER INFORMATION: n is a, c, g, or t

<400> SEQUENCE: 41
accgacgcga acatcnnc 18

<210> SEQ ID NO 42
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 42
tcctctccgc tcaccgacgc 20

<210> SEQ ID NO 43
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 43
tcacacagat aaacttct 18

<210> SEQ ID NO 44
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 44
aagccaagaa gttcacacag 20

<210> SEQ ID NO 45
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 45
tcacgcagat gaacgtct 18

<210> SEQ ID NO 46
<211> LENGTH: 20
<212> TYPE: DNA

-continued

<213> ORGANISM: Artificial Sequence
<220> FEATURE:
<223> OTHER INFORMATION: Synthetic antisense oligomer

<400> SEQUENCE: 46
gagatcggaa gctcacgcag 20

<210> SEQ ID NO 47
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 47
gctcacacag gcgaactact 20

<210> SEQ ID NO 48
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 48
taagtttgtc agctcacaca g 21

<210> SEQ ID NO 49
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 49
caattagcac acaggattta ct 22

<210> SEQ ID NO 50
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 50
ttgcagacca atgcacctca 20

<210> SEQ ID NO 51
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 51
gtccacgtag actaacaact 20

<210> SEQ ID NO 52
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 52
gtctttgtcg gtccacgtag 20

<210> SEQ ID NO 53
<211> LENGTH: 17
<212> TYPE: DNA
<213> ORGANISM: Artificial Sequence
<220> FEATURE:
<223> OTHER INFORMATION: Synthetic antisense oligomer

<400> SEQUENCE: 53
cccatcaggg ggctggc 17

<210> SEQ ID NO 54
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 54
tggagtgtcg cccccatcag 20

<210> SEQ ID NO 55
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 55
atgcacgtgc aagaaaatct 20

<210> SEQ ID NO 56
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 56
atgctgtccg aagcaaacgc 20

<210> SEQ ID NO 57
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 57
cacgcacgtg caagaaaatc t 21

<210> SEQ ID NO 58
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 58
tgaagcaagc gcacgcacgt 20

<210> SEQ ID NO 59
<211> LENGTH: 20
<212> TYPE: DNA
<213> ORGANISM: Artificial Sequence
<220> FEATURE:

<223> OTHER INFORMATION: Synthetic antisense oligomer

<400> SEQUENCE: 59
acacacgtgc aagaaaatct 20

<210> SEQ ID NO 60
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 60
acactgacta aagcacccgc 20

<210> SEQ ID NO 61
<211> LENGTH: 24
<212> TYPE: DNA
<213> ORGANISM: Artificial Sequence
<220> FEATURE:
<223> OTHER INFORMATION: Synthetic antisense oligomer

<400> SEQUENCE: 61
ggtacaaccc cagagctgtt ttaa 24

<210> SEQ ID NO 62
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 62
gtgggcctct ggggtgggta 20

<210> SEQ ID NO 63
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 63
caacccacag gctgttttaa 20

<210> SEQ ID NO 64
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 64
gtgggccctg tgggtgggta 20

<210> SEQ ID NO 65
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 65
caacccacag gctgttttaa 20

-continued

<210> SEQ ID NO 66
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 66
aatgggcctg tgggtgggaa 20

<210> SEQ ID NO 67
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 67
caaccccaga gctgttttaa 20

<210> SEQ ID NO 68
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 68
gtgggcctct ggggtgggag 20

<210> SEQ ID NO 69
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 69
caaccccaga gctgttttaa 20

<210> SEQ ID NO 70
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 70
gtgggcctct ggggtgggaa 20

<210> SEQ ID NO 71
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 71
cctgttgggt gggaacactc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 72
agagtacaac acccagtggg 20

<210> SEQ ID NO 73
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 73
caacccccag gctgttttaa 20

<210> SEQ ID NO 74
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 74
gtgggcccca ggggtgggta 20

<210> SEQ ID NO 75
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 75
caacccactc ccagttttaa 20

<210> SEQ ID NO 76
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 76
atgggtggag tgagtgggaa 20

<210> SEQ ID NO 77
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 77
atacccatcc gctgttttaa 20

<210> SEQ ID NO 78
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 78
ccaatgggtc gaatggtggg 20

<210> SEQ ID NO 79
<211> LENGTH: 21

-continued

<212> TYPE: DNA
<213> ORGANISM: Artificial Sequence
<220> FEATURE:
<223> OTHER INFORMATION: Synthetic antisense oligomer

<400> SEQUENCE: 79
aaccctagcg cccccttca a 21

<210> SEQ ID NO 80
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 80
gttggcatgc taggggtgaa 20

<210> SEQ ID NO 81
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 81
tcccggagac ccctcttgaa 20

<210> SEQ ID NO 82
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 82
ccaagaggga ctccggaaat 20

<210> SEQ ID NO 83
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 83
ttgtctcaaa tttcttttac 20

<210> SEQ ID NO 84
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 84
gaagctcaga gtttgagaca 20

<210> SEQ ID NO 85
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 85
agaagccatt tctcattaac 20

<210> SEQ ID NO 86
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 86
gagctcgaga gagcgatggc 20

<210> SEQ ID NO 87
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 87
caattagcca tcacgatcac 20

<210> SEQ ID NO 88
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 88
ggcaacggac ggcaattagc 20

<210> SEQ ID NO 89
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 89
tctctctata attaaatcac 20

<210> SEQ ID NO 90
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 90
aaagtcacta tctctctata 20

<210> SEQ ID NO 91
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 91
ttgacgccat catcattcac 20

<210> SEQ ID NO 92
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 92
agcagtagga acgacgtctt 20

<210> SEQ ID NO 93
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 93
aactgatggg cctccatggc 20

<210> SEQ ID NO 94
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 94
tgatgccagg agccttaata 20

<210> SEQ ID NO 95
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 95
cgaggtccga tagcttccat 20

<210> SEQ ID NO 96
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 96
atgggaatgg gagtcctaag 20

<210> SEQ ID NO 97
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 97
ggtaggtaaa aacctaatat 20

<210> SEQ ID NO 98
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 98
aggttggttg gcttttcctg 20

<210> SEQ ID NO 99
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 99
gatagaaaat ctttttaagt 20

<210> SEQ ID NO 100
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 100
aaaagagcta actatccgta 20

<210> SEQ ID NO 101
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 101
actcacttta ctttaaaagt 20

<210> SEQ ID NO 102
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 102
gccacgctac actcacttta 20

<210> SEQ ID NO 103
<211> LENGTH: 20
<212> TYPE: DNA
<213> ORGANISM: Artificial Sequence
<220> FEATURE:
<223> OTHER INFORMATION: synthetic antisense oligomer

<400> SEQUENCE: 103
cacgcaaatc gctcgcaatc 20

<210> SEQ ID NO 104
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 104
tcagtgaagc gggatgcacg 20

<210> SEQ ID NO 105
<211> LENGTH: 20
<212> TYPE: DNA
<213> ORGANISM: Artificial Sequence
<220> FEATURE:
<223> OTHER INFORMATION: Synthetic antisense oligomer -continued

<400> SEQUENCE: 105
gatagataag gtacttaagt 20

<210> SEQ ID NO 106
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 106
aagcaacttt tctatctgta 20

<210> SEQ ID NO 107
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 107
cggacgccaa tcactcttat a 21

<210> SEQ ID NO 108
<211> LENGTH: 22
<212> TYPE: DNA
<213> ORGANISM: Artificial Sequence
<220> FEATURE:
<223> OTHER INFORMATION: Synthetic antisense oligomer

<400> SEQUENCE: 108
gagttgagag ggtacgtacg ga 22

<210> SEQ ID NO 109
<211> LENGTH: 21
<212> TYPE: DNA
<213> ORGANISM: Artificial Sequence
<220> FEATURE:
<223> OTHER INFORMATION: Synthetic antisense oligomer

<400> SEQUENCE: 109
catagagcca acacctatac g 21

<210> SEQ ID NO 110
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 110
atacaaatgc caaggcatag 20

<210> SEQ ID NO 111
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 111
gcaccataca cacttcgagc 20

<210> SEQ ID NO 112

<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 112
atggtggtga gccgtatatg 20

<210> SEQ ID NO 113
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 113
aatcaccacc cccctcttgg 20

<210> SEQ ID NO 114
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 114
gccaaaggcc aatcaccacc 20

<210> SEQ ID NO 115
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 115
gcctctacac cgtaccctat 20

<210> SEQ ID NO 116
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 116
taggtggaaa tagggtggtt 20

<210> SEQ ID NO 117
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 117
gatcgattag tttgtagggt 20

<210> SEQ ID NO 118
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 118

```
cgtgaattct ttccatattg                                              20


<210> SEQ ID NO 119
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 119

ttctctcttg cgccgcccat                                              20


<210> SEQ ID NO 120
<211> LENGTH: 20
<212> TYPE: DNA
<213> ORGANISM: Artificial Sequence
<220> FEATURE:
<223> OTHER INFORMATION: Synthetic antisense oligomer

<400> SEQUENCE: 120

ggtaggtaat tggtttgggc                                              20


<210> SEQ ID NO 121
<211> LENGTH: 12
<212> TYPE: PRT
<213> ORGANISM: Artificial Sequence
<220> FEATURE:
<223> OTHER INFORMATION: Synthetic Arginine-rich peptide

<400> SEQUENCE: 121

Arg Arg Arg Arg Arg Arg Arg Arg Arg Phe Phe Cys
1               5                   10


<210> SEQ ID NO 122
<211> LENGTH: 14
<212> TYPE: PRT
<213> ORGANISM: Artificial Sequence
<220> FEATURE:
<223> OTHER INFORMATION: Synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (5)..(5)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (11)..(11)
<223> OTHER INFORMATION: Xaa = 6-aminohexanoic acid
<220> FEATURE:
<221> NAME/KEY: misc_feature
<222> LOCATION: (13)..(13)
<223> OTHER INFORMATION: Xaa = 6-aminohexanoic acid
<220> FEATURE:
<221> NAME/KEY: misc_feature
<222> LOCATION: (14)..(14)
<223> OTHER INFORMATION: Xaa = beta-Alanine

<400> SEQUENCE: 122

Arg Xaa Arg Arg Xaa Arg Arg Xaa Arg Arg Xaa Arg Xaa Xaa
1               5                   10


<210> SEQ ID NO 123
```

<211> LENGTH: 17
<212> TYPE: PRT
<213> ORGANISM: Artificial Sequence
<220> FEATURE:
<223> OTHER INFORMATION: Synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (4)..(4)
<223> OTHER INFORMATION: Xaa = 6-aminohexanoic acid
<220> FEATURE:
<221> NAME/KEY: misc_feature
<222> LOCATION: (6)..(6)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (10)..(10)
<223> OTHER INFORMATION: Xaa = 6-aminohexanoic acid
<220> FEATURE:
<221> NAME/KEY: misc_feature
<222> LOCATION: (12)..(12)
<223> OTHER INFORMATION: Xaa = 6-aminohexanoic acid
<220> FEATURE:
<221> NAME/KEY: misc_feature
<222> LOCATION: (14)..(14)
<223> OTHER INFORMATION: Xaa = 6-aminohexanoic acid
<220> FEATURE:
<221> NAME/KEY: misc_feature
<222> LOCATION: (16)..(16)
<223> OTHER INFORMATION: Xaa = 6-aminohexanoic acid
<220> FEATURE:
<221> NAME/KEY: misc_feature
<222> LOCATION: (17)..(17)
<223> OTHER INFORMATION: Xaa = beta-Alanine

<400> SEQUENCE: 123

```
Arg Xaa Arg Xaa Arg Xaa Arg Xaa Arg Xaa Arg Xaa Arg Xaa Arg Xaa
1               5                   10                  15

Xaa
```

<210> SEQ ID NO 124
<211> LENGTH: 9
<212> TYPE: PRT
<213> ORGANISM: Artificial Sequence
<220> FEATURE:
<223> OTHER INFORMATION: Synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (4)..(4)
<223> OTHER INFORMATION: Xaa = 6-aminohexanoic acid
<220> FEATURE:
<221> NAME/KEY: misc_feature
<222> LOCATION: (6)..(6)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (9)..(9)
<223> OTHER INFORMATION: Xaa = beta-Alanine

<400> SEQUENCE: 124

Arg Xaa Arg Xaa Arg Xaa Arg Xaa Xaa
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (5)..(5)
<223> OTHER INFORMATION: Xaa = 6-aminohexanoic acid
<220> FEATURE:
<221> NAME/KEY: misc_feature
<222> LOCATION: (7)..(7)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = beta-Alanine

<400> SEQUENCE: 125

Arg Xaa Arg Arg Xaa Arg Xaa Xaa
1               5

<210> SEQ ID NO 126
<211> LENGTH: 11
<212> TYPE: PRT
<213> ORGANISM: Artificial Sequence
<220> FEATURE:
<223> OTHER INFORMATION: Synthetic Arginine-rich peptide
<220> FEATURE:
<221> NAME/KEY: misc_feature
<222> LOCATION: (2)..(2)
<223> OTHER INFORMATION: Xaa = 6-aminohexanoic acid
<220> FEATURE:
<221> NAME/KEY: misc_feature
<222> LOCATION: (5)..(5)
<223> OTHER INFORMATION: Xaa = 6-aminohexanoic acid
<220> FEATURE:
<221> NAME/KEY: misc_feature
<222> LOCATION: (8)..(8)
<223> OTHER INFORMATION: Xaa = 6-aminohexanoic acid
<220> FEATURE:
<221> NAME/KEY: misc_feature
<222> LOCATION: (10)..(10)
<223> OTHER INFORMATION: Xaa = 6-aminohexanoic acid
<220> FEATURE:
<221> NAME/KEY: misc_feature
<222> LOCATION: (11)..(11)
<223> OTHER INFORMATION: Xaa = beta-Alanine

<400> SEQUENCE: 126

Arg Xaa Arg Arg Xaa Arg Arg Xaa Arg Xaa Xaa
1               5                   10

<210> SEQ ID NO 127
<211> LENGTH: 14
<212> TYPE: DNA
<213> ORGANISM: Artificial Sequence
<220> FEATURE:
<223> OTHER INFORMATION: Synthetic antisense oligomer

<400> SEQUENCE: 127
acaggcgaac tact                                                    14

<210> SEQ ID NO 128

-continued

<211> LENGTH: 12
<212> TYPE: DNA
<213> ORGANISM: Artificial Sequence
<220> FEATURE:
<223> OTHER INFORMATION: Synthetic antisense oligomer

<400> SEQUENCE: 128
gtcagctcac ac 12

<210> SEQ ID NO 129
<211> LENGTH: 14
<212> TYPE: DNA
<213> ORGANISM: Artificial Sequence
<220> FEATURE:
<223> OTHER INFORMATION: synthetic antisense oligomer

<400> SEQUENCE: 129
gctcacacag gcga 14

<210> SEQ ID NO 130
<211> LENGTH: 16
<212> TYPE: DNA
<213> ORGANISM: Artificial Sequence
<220> FEATURE:
<223> OTHER INFORMATION: Synthetic antisense oligomer

<400> SEQUENCE: 130
gcacacagga tttact 16

<210> SEQ ID NO 131
<211> LENGTH: 14
<212> TYPE: DNA
<213> ORGANISM: Artificial Sequence
<220> FEATURE:
<223> OTHER INFORMATION: Synthetic antisense oligomer

<400> SEQUENCE: 131
gtccaatgca cctc 14

<210> SEQ ID NO 132
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 132
caatgcacct caattagc 18

<210> SEQ ID NO 133
<211> LENGTH: 20
<212> TYPE: DNA
<213> ORGANISM: Artificial Sequence
<220> FEATURE:
<223> OTHER INFORMATION: Synthetic scramble control

<400> SEQUENCE: 133
agtctcgact tgctacctca 20

<210> SEQ ID NO 134
<211> LENGTH: 14
<212> TYPE: DNA
<213> ORGANISM: Artificial Sequence
<220> FEATURE:
<223> OTHER INFORMATION: Synthetic antisense oligomer

<400> SEQUENCE: 134
acaggcgaac tact 14

<210> SEQ ID NO 135
<211> LENGTH: 12
<212> TYPE: DNA
<213> ORGANISM: Artificial Sequence
<220> FEATURE:
<223> OTHER INFORMATION: Synthetic antisense oligomer

<400> SEQUENCE: 135
gtcagctcac ac 12

<210> SEQ ID NO 136
<211> LENGTH: 14
<212> TYPE: DNA
<213> ORGANISM: Artificial Sequence
<220> FEATURE:
<223> OTHER INFORMATION: synthetic antisense oligomer

<400> SEQUENCE: 136
gctcacacag gcga 14

<210> SEQ ID NO 137
<211> LENGTH: 16
<212> TYPE: DNA
<213> ORGANISM: Artificial Sequence
<220> FEATURE:
<223> OTHER INFORMATION: Synthetic antisense oligomer

<400> SEQUENCE: 137
gcacacagga tttact 16

<210> SEQ ID NO 138
<211> LENGTH: 14
<212> TYPE: DNA
<213> ORGANISM: Artificial Sequence
<220> FEATURE:
<223> OTHER INFORMATION: Synthetic antisense oligomer

<400> SEQUENCE: 138
gtccaatgca cctc 14

<210> SEQ ID NO 139
<211> LENGTH: 18
<212> TYPE: DNA
<213> ORGANISM: Artificial Sequence
<220> FEATURE:
<223> OTHER INFORMATION: Synthetic antisense oligomer

<400> SEQUENCE: 139
caatgcacct caattagc 18

<210> SEQ ID NO 140
<211> LENGTH: 40
<212> TYPE: RNA
<213> ORGANISM: Japanese encephalitis virus

<400> SEQUENCE: 140
agaaguuuau cugugugaac uucuuggcuu aguaucguug 40

<210> SEQ ID NO 141
<211> LENGTH: 40
<212> TYPE: RNA
<213> ORGANISM: Murray Valley encephalitis virus

<400> SEQUENCE: 141
agacguucau cugcgugagc uuccgaucuc aguauuguuu 40

<210> SEQ ID NO 142
<211> LENGTH: 40
<212> TYPE: RNA
<213> ORGANISM: West Nile virus

<400> SEQUENCE: 142
aguaguucgc cugugugagc ugacaaacuu aguaguguuu 40

<210> SEQ ID NO 143
<211> LENGTH: 40
<212> TYPE: RNA
<213> ORGANISM: Yellow Fever virus

<400> SEQUENCE: 143
aguaaauccu gugugcuaau ugaggugcau uggucugcaa 40

<210> SEQ ID NO 144
<211> LENGTH: 40
<212> TYPE: RNA
<213> ORGANISM: Dengue Type 2 virus

<400> SEQUENCE: 144
aguuguuagu cuacguggac cgacaaagac agauucuuug 40

<210> SEQ ID NO 145
<211> LENGTH: 40
<212> TYPE: RNA
<213> ORGANISM: Hepatitis C virus

<400> SEQUENCE: 145
gccagccccc ugaugggggc gacacuccac caugaaucac 40

<210> SEQ ID NO 146
<211> LENGTH: 40
<212> TYPE: RNA
<213> ORGANISM: Tick-borne encephalitis virus

<400> SEQUENCE: 146
agauuuucuu gcacgugcau gcguuugcuu cggacagcau 40

<210> SEQ ID NO 147
<211> LENGTH: 40
<212> TYPE: RNA
<213> ORGANISM: Omsk hemorrhagic fever virus

<400> SEQUENCE: 147
agauuuucuu gcacgugcgu gcgcuugcuu cagacagcaa 40

<210> SEQ ID NO 148
<211> LENGTH: 40
<212> TYPE: RNA
<213> ORGANISM: Powassan virus

<400> SEQUENCE: 148
agauuuucuu gcacgugugu gcgggugcuu uagucagugu 40

<210> SEQ ID NO 149
<211> LENGTH: 40
<212> TYPE: RNA
<213> ORGANISM: Poliovirus Mahoney strain

<400> SEQUENCE: 149
uuaaaacagc ucugggguug uacccacccc agaggcccac 40

<210> SEQ ID NO 150
<211> LENGTH: 40
<212> TYPE: RNA
<213> ORGANISM: Human enterovirus A

<400> SEQUENCE: 150
uuaaaacagc cugugggguug uacccaccca cagggcccac 40

<210> SEQ ID NO 151
<211> LENGTH: 40
<212> TYPE: RNA
<213> ORGANISM: Human enterovirus B

<400> SEQUENCE: 151
uuaaaacagc cuguggguug uucccaccca caggcccauu 40

<210> SEQ ID NO 152
<211> LENGTH: 40
<212> TYPE: RNA
<213> ORGANISM: Human enterovirus C

<400> SEQUENCE: 152
uuaaaacagc ucugggguug cucccacccc agaggcccac 40

<210> SEQ ID NO 153
<211> LENGTH: 40
<212> TYPE: RNA
<213> ORGANISM: Bovine enterovirus

<400> SEQUENCE: 153
uuaaaacagc cugggguug uacccacccc uggggcccac 40

<210> SEQ ID NO 154
<211> LENGTH: 40
<212> TYPE: RNA
<213> ORGANISM: Human rhinovirus 89

<400> SEQUENCE: 154
uuaaaacugg gaguggguug uucccacuca cuccacccau 40

<210> SEQ ID NO 155
<211> LENGTH: 40
<212> TYPE: RNA
<213> ORGANISM: Human rhinovirus B

<400> SEQUENCE: 155
uuaaaacagc ggaugguau cccaccauuc gacccauugg 40

<210> SEQ ID NO 156
<211> LENGTH: 40
<212> TYPE: RNA
<213> ORGANISM: Foot-and-mouth disease virus

<400> SEQUENCE: 156
uugaaagggg gcacuagggu cucaucucua gcacgccaac 40

<210> SEQ ID NO 157
<211> LENGTH: 40
<212> TYPE: RNA

<213> ORGANISM: Hepatitis A virus

<400> SEQUENCE: 157
uucaagaggg gucuccggga auuuccggag ucccucuugg 40

<210> SEQ ID NO 158
<211> LENGTH: 40
<212> TYPE: RNA
<213> ORGANISM: Feline calicivirus

<400> SEQUENCE: 158
guaaaagaaa uuugagacaa ugucucaaac ucugagcuuc 40

<210> SEQ ID NO 159
<211> LENGTH: 40
<212> TYPE: RNA
<213> ORGANISM: Canine calicivirus

<400> SEQUENCE: 159
guuaaugaga aauggcuucu gccaucgcuc ucucgagcuc 40

<210> SEQ ID NO 160
<211> LENGTH: 40
<212> TYPE: RNA
<213> ORGANISM: Porcine enteric calicivirus

<400> SEQUENCE: 160
gugaucguga uggcuaauug ccguccguug ccuauugggc 40

<210> SEQ ID NO 161
<211> LENGTH: 40
<212> TYPE: RNA
<213> ORGANISM: Calcivirus strain NB

<400> SEQUENCE: 161
gugauuuaau uauagagaga uagugacuuu cacuuuucuu 40

<210> SEQ ID NO 162
<211> LENGTH: 40
<212> TYPE: RNA
<213> ORGANISM: Norwalk virus

<400> SEQUENCE: 162
gugaaugaug auggcgucaa aagacgucgu uccuacugcu 40

<210> SEQ ID NO 163
<211> LENGTH: 40
<212> TYPE: RNA
<213> ORGANISM: Hepatitis E virus

<400> SEQUENCE: 163
gccauggagg cccaucaguu uauuaaggcu ccuggcauca 40

<210> SEQ ID NO 164
<211> LENGTH: 40
<212> TYPE: RNA
<213> ORGANISM: Rubella virus

<400> SEQUENCE: 164
auggaagcua ucggaccucg cuuaggacuc ccauucccau 40

<210> SEQ ID NO 165
<211> LENGTH: 40

-continued

<212> TYPE: RNA
<213> ORGANISM: SARS coronavirus

<400> SEQUENCE: 165
auauuagguu uuuaccuacc caggaaaagc caaccaaccu 40

<210> SEQ ID NO 166
<211> LENGTH: 40
<212> TYPE: RNA
<213> ORGANISM: Porcine epidemic diarrhea virus

<400> SEQUENCE: 166
acuuaaaaag auuuucuauc uacggauagu uagcucuuuu 40

<210> SEQ ID NO 167
<211> LENGTH: 40
<212> TYPE: RNA
<213> ORGANISM: Transmissible gastroenteritis virus

<400> SEQUENCE: 167
acuuuuaaag uaaagugagu guagcguggc uauaucucuu 40

<210> SEQ ID NO 168
<211> LENGTH: 40
<212> TYPE: RNA
<213> ORGANISM: Bovine coronavirus

<400> SEQUENCE: 168
gauugcgagc gauuugcgug cgugcauccc gcuucacuga 40

<210> SEQ ID NO 169
<211> LENGTH: 40
<212> TYPE: RNA
<213> ORGANISM: Human coronavirus 229E

<400> SEQUENCE: 169
acuuaaguac cuuaucuauc uacagauaga aaaguugcuu 40

<210> SEQ ID NO 170
<211> LENGTH: 40
<212> TYPE: RNA
<213> ORGANISM: Murine Hepatitis virus

<400> SEQUENCE: 170
uauaagagug auuggcgucc guacguaccc ucucaacucu 40

<210> SEQ ID NO 171
<211> LENGTH: 40
<212> TYPE: RNA
<213> ORGANISM: Porcine reproductive and respiratory syndrome virus

<400> SEQUENCE: 171
cgcccgggca gguguuggcu cuaugccucg gcauuuguau 40

<210> SEQ ID NO 172
<211> LENGTH: 40
<212> TYPE: RNA
<213> ORGANISM: Human astrovirus

<400> SEQUENCE: 172
ccaagagggg gguggugauu ggccuuuggc uuaucagugu 40

<210> SEQ ID NO 173

-continued

<211> LENGTH: 40
<212> TYPE: RNA
<213> ORGANISM: Eastern equine encephalitis virus

<400> SEQUENCE: 173
auaggguacg guguagaggc aaccacccua uuuccaccua 40

<210> SEQ ID NO 174
<211> LENGTH: 40
<212> TYPE: RNA
<213> ORGANISM: Western equine encephalomyelitis virus

<400> SEQUENCE: 174
acccuacaaa cuaaucgauc caauauggaa agaauucacg 40

<210> SEQ ID NO 175
<211> LENGTH: 40
<212> TYPE: RNA
<213> ORGANISM: Venezuelan equine encephalitis virus

<400> SEQUENCE: 175
augggcggcg caagagagaa gcccaaacca auuaccuacc 40